US009718871B2

(12) United States Patent
Gallo et al.

(10) Patent No.: US 9,718,871 B2
(45) Date of Patent: Aug. 1, 2017

(54) GENERATING TARGETED SEQUENCE DIVERSITY IN PROTEINS

(71) Applicant: Innovative Targeting Solutions Inc., Burnaby (CA)

(72) Inventors: Michael Gallo, North Vancouver (CA); Jaspal Singh Kang, Surrey (CA); Craig Robin Pigott, Vancouver (CA); Abby Lin, Burnaby (CA)

(73) Assignee: INNOVATIVE TARGETING SOLUTIONS INC., Burnaby (CA)

( * ) Notice: Subject to any disclaimer, the term of this patent is extended or adjusted under 35 U.S.C. 154(b) by 0 days.

(21) Appl. No.: 14/384,772

(22) PCT Filed: Mar. 14, 2013

(86) PCT No.: PCT/CA2013/050203
§ 371 (c)(1),
(2) Date: Sep. 12, 2014

(87) PCT Pub. No.: WO2013/134880
PCT Pub. Date: Sep. 19, 2013

(65) Prior Publication Data
US 2015/0329850 A1    Nov. 19, 2015

Related U.S. Application Data

(60) Provisional application No. 61/610,774, filed on Mar. 14, 2012.

(51) Int. Cl.
| | |
|---|---|
| *G01N 33/53* | (2006.01) |
| *C12N 15/63* | (2006.01) |
| *C12N 15/87* | (2006.01) |
| *C07H 21/04* | (2006.01) |
| *C07K 14/78* | (2006.01) |
| *C07K 16/32* | (2006.01) |
| *C07K 16/00* | (2006.01) |
| *C12N 15/10* | (2006.01) |
| *A01K 67/00* | (2006.01) |

(52) U.S. Cl.
CPC .............. *C07K 14/78* (2013.01); *C07K 16/00* (2013.01); *C07K 16/005* (2013.01); *C07K 16/32* (2013.01); *C12N 15/102* (2013.01); *C07K 2317/14* (2013.01); *C07K 2317/565* (2013.01); *C07K 2318/00* (2013.01); *C07K 2318/20* (2013.01); *C07K 2319/03* (2013.01); *C07K 2319/30* (2013.01)

(58) Field of Classification Search
CPC .......... C07K 2317/14; C07K 2317/565; C07K 2318/00; C07K 2318/20; C07K 2319/03; C12N 15/102
USPC ......... 435/7.1, 455, 462; 536/23.53
See application file for complete search history.

(56) References Cited

U.S. PATENT DOCUMENTS

| 5,756,323 A * | 5/1998 | Kallenbach ........ C07K 14/4705 435/465 |
| 6,242,236 B1 * | 6/2001 | Wohlstadter ......... C12N 9/0002 435/18 |

FOREIGN PATENT DOCUMENTS

| WO | 93/12228 | 6/1993 |
| WO | 2005/060642 | 7/2005 |
| WO | 2009/129247 | 10/2009 |
| WO | WO2009/129247 | * 10/2009 |
| WO | 2012-018764 | 2/2012 |

OTHER PUBLICATIONS

Maes et al., "Secondary V(D)J Rearrangements and B Cell Receptor-Mediated Down-Regulation of Recombination Activating Gene-2 Expression in a Murine B Cell Line," The Journal of Immunology, vol. 165, pp. 703-709 (2000).
Makrides et al., "Strategies for Achieving High-Level Expression of Genes in *Escherichia coli*," Microbiological Reviews, vol. 60, No. 3, pp. 512-538 (1996).
Mayer, "A New Set of Useful Cloning and Expression Vectors Derived from pBlueScript," Gene, vol. 163, pp. 41-46 (1995).
Miller, "Retrovirus Packaging Cells," Human Gene Therapy, vol. 1, pp. 5-14 (1990).
Miller et al., "Improved Retroviral Vectors for Gene Transfer and Expression," vol. 7, No. 9, pp. 980-990 (1989).
Minke et al.; "TRP Channel Proteins and Signal Transduction," Physiological Review, vol. 82, pp. 429-472 (2002).
Nadel et al., "Sequence of the Spacer in the Recombination Signal Sequence Affects V(D)J Rearrangement Frequency and Correlates with Nonrandom VK Usage In Vitro," Journal of Experimental Medicine, vol. 187, No. 9, pp. 1495-1503 (1998).
Nareoja et al., "Selective Targeting of G-Protein-Coupled Receptor Subtypes with Venom Peptides," Acta physiologica, vol. 204, pp. 186-201 (2012).
Nicaise et al., "Affinity Transfer by CDR Grafting on a Nonimmunoglobulin Scaffold," Protein Science, vol. 13, pp. 1882-1891 (2004).

(Continued)

*Primary Examiner* — Quang Nguyen
(74) *Attorney, Agent, or Firm* — Thompson Coburn LLP

(57) ABSTRACT

Methods of generating sequence diversity in a protein, such as a ligand-binding protein, are provided. The methods comprise targeted introduction of two or more recombination signal sequences (RSSs) into the protein coding sequence and introduction of the modified protein coding sequence into a recombination-competent host cell, specifically a recombination-competent host cell that is capable of expressing at least RAG-1 and RAG-2, thereby allowing for recombination of the protein coding sequence and expression of variant proteins. Also provided are polynucleotides comprising a nucleic acid sequence encoding a target protein, such as a ligand-binding protein, and comprising two or more RSSs, and compositions and host cells comprising same.

16 Claims, 35 Drawing Sheets

(56) References Cited

OTHER PUBLICATIONS

Nord et al., "Binding Proteins Selected from Combinatorial Libraries of α-Helical Bacterial Receptor Domain," Nature Biotechnology, vol. 15, pp. 772-777 (1991).
Nygren et al., "Binding Proteins from Alternative Scaffolds," Journal of Immunological methods, vol. 290, pp. 3-28 (2004).
Oettinger et al., "RAG-1 and RAG-2, Adjacent Genes That Synergistically Activate V(D)J Recombination," Science, vol. 248, No. 4962, pp. 1517-1523 (1990).
Parker et al., "Antibody Mimics Based on Human Fibronectin Type Three Domain Engineered for Thermostability and High-Affinity Binding to Vascular Endothelial Growth Factor Receptor Two," Protein Engineering, Design & Selection, vol. 18, No. 9, pp. 435-444 (2005).
Peterson et al., "Molecular Cloning of Human Terminal Deoxynucleotidyltransferase," Proceedings of the National Academy of Sciences, vol. 81, pp. 4363-4367 (1984).
Phoenix et al., "The Hydrophobic Moment and its Use in the Classification of Amphiphilic Structures (Review)," Molecular Membrane Biology, vol. 19, pp. 1-10 (2002).
Ramsden et al., "Mouse K light-Chain Recombination Signal Sequences Mediate Recombination More Frequently than do those of λ Light Chain," Proceedings of the National Academy of Sciences, vol. 88, pp. 10721-10725 (1991).
Rathbun et al., "Comparison of RAG Gene Expression in Normal and Transformed Precursor Lymphocytes," International Immunology, vol. 5, No. 8, pp. 997-1000 (1993).
Riechmann et at., "Reshaping Human Antibodies for Therapy," Nature, vol. 3 pp. 323-327 (1998).
Robinson et al., "Optimizing the Stability of Single-Chain Proteins by Linker Length and Composition Mutagenesis," Proceedings of the National Academy of Sciences, vol. 95, pp. 5929-5934 (1998).
Roch et al , "V(D)J Recombination Frequency is Affected by the Sequence Interposed Between a Pair of Recombination Signals: Sequence Comparison Reveals a Putative Recombinational Enhancer Element," Nucleic Acids Research, vol. 25, No. 12, pp. 2303-2310 (1997).
Rock et al., "CDR3 Length in Antigen-Specific Immune Receptors," Journal of Experimental Medicine, vol. 179, pp. 323-328 (1994).
Rothe et al., "In Vitro Display technologies Reveal Novel Biopharmaceutics," The FASEB Journal, vol. 20, pp. 1599-1610 (2006).
Runge et al., "Crystal Structure of the Ligand-Bound Glucagon-Like Peptide-1 Receptor Extracellular Domain," The Journal of Bilogical Chemistry, vol. 283, No. 17, pp. 11340-11347 (2008).
Sadlish et al. "Cytoplasmic Domains of the Reduced Folate Carrier are Essential for Trafficking, but not Function," Biochemical Journal, vol. 364, pp. 777-786 (2002).
Sarmiento et al., "Diverging Mechanisms of Activation of Chemokine Receptors Revealed by Novel Chernokine Agonists," PLoS ONE, vol. 6, No. 12 e27967 (2011).
Sauer, "Inducible Gene Targeting in Mice Using the Cre/lox System," Methods: A Companion to Methods in Enzymology, vol. 14, pp. 381-392 (1998).
Sauer, "Cre/lox: One More Step in the Taming of the Genome," Endocrine, vol. 19, No. 3, pp. 221-227 (2002).
Schatz et al., "The V(D)J Recombination Activating Gene, RAG-1," Cell, vol. 59, pp. 1035-1048 (1989).
Schlessinger, "Ligand-Induced, Receptor-Mediated Dimerization and Activation of EGF Receptor," Cell, vol. 110, pp. 669-672 (2002).
Simon et al., "Display of Somatostatin-Related Peptides in the Complementarity Determining Regions of an Antibody Light Chain," Archives of Biochemistry and Biophysics, vol. 440, pp. 148-157 (2005).

Sollazzo et al., "Expression of an Exogenous Peptide Epitope Genetically Engineered in the Variable Domain of an Immunoglobulin: Implications for Antibody and Peptide Folding," Protein Engineering, vol. 4, No. 2, pp. 215-220 (1990).
Spiro, "Protein Glycosylation: Nature, Distribution, Enzymatic Formation, and Disease Implications of Glycopeptide Bonds," Glycohiology, vol. 12, No. 4, pp. 43R-56R (2002).
Ritter et al., "Fine-Tuning of GPCR Activity by Receptor-Interacting Proteins," Nature Reviews Molecular Cell Biology, vol. 10, No. 12, pp. 819-830 (2009).
Stemmer, "Rapid Evolution of a protein in Vitro by DNA Shuffling," Letters to Nature, vol. 370, pp. 389-391 (1994).
Takada et al., "The Integrins," Genome Biology, vol. 8, No. 5, pp. 215.1-215.9 (2007).
Thai et al., "Distinct and Opposite Diversifying Activities of Terminal Transferase Splice Variants," Nature Immunology, vol. 3, No. 5 (2002).
Thai et al., "Distinct and Opposite Diversifying Activities of Human Terminal Deoxynucleotidyltransferase Splice Variants," The Journal of Immunology, No. 173, pp. 4009-4019 (2004).
Thomson et al., "Mutational Analysis of LoxP Sites forEfficient Cre-Mediated Insertion Into Genomic DNA," Genesis, vol. 36, pp. 162-167 (2003).
Tomlinson et al., "The Imprint of Somatic Hypermutation on the Repertoire of Human Germline V Genes," Journal of Molecular Biology, vol. 256, pp. 813-817 (1996).
Underwood et al., "Crystal Structure of Glucagon-Like Peptide-1 in Complex with the Extracellular Domain of the Glucagon-Like Peptide-1 Receptor," Journal of Biological Chemistry, vol. 285, No. 1, pp. 723-730 (2010).
Van Craenebroeck et al., "Episomal Vectors for Gene Expression in Mammalian Cells," European Journal of Biochemistry, vol. 267, pp. 5665-5678 (2000).
Van den Beucken et al., "Building Novel Binding Ligands to B7.1 and B7.2 Based on Human Antibody Single variable Light Chain Domains," Journal of Molecular Biology vol. 310, pp. 591-601 (2001).
Verhoeyen et al., "Reshaping Human Antibodies: Grafting an Antilysozyme Activity," Science, vol. 239, pp. 1534-1536 (1988).
Wollscheid et al., "Lipid Raft Proteins and Their Identification in T. Lymphocytes," Subcellular Biochemistry, vol. 37: Membrane Dynamics and Domains, Chapter 3, pp. 121-152 (2004).
Yang et al., "CDR Walking Mutagenesis for the Affinity Maturation of a Ptent Human Anti-HIV-1 Antibody into the Picomolar Range," Journal of Molecular Biology, vol. 254. pp. 392-403 (1995).
Zanetti et al., "Epression of Conformationally Constrained Adhesion Peptide in an Antibody CDR Loop and Inhibition of Natural Killer Cell Cytotoxic Activity by an Antibody Antigenized with the RGD Motif," The EMBO Journal, vol. 12, No. 11, pp. 4375-4384 (1993).
Zeytun et al., "Fluorobodies combine GFP Fluorescence with the Binding Characteristics of Antibodies," Nature Biotechnology, vol. 21, No. 12, pp. 1473-1479 (2003).
Zheng et al., Expression and Secretion of Immunoglobulin Alpha Heavy Chain with diverse VDJ Recombinations by Human Epithelial Caner Cells, Molecular Immunology, vol. 44, pp. 2221-2227 (2007).
Akamatsu et al., "Essential Residues in V(D)J Recombination Signals," The Journal of Immunology, vol. 153, pp. 4520-4529 (1994).
Allgood et al., "Chimeric Receptors as Gene Switches," Current Opinion in Biotechnology, vol. 8, pp. 474-479 (1997).
Baubonis, et al., "Genomic Targeting with Purified Cre Recombinase," Nucleic Acids Research, vol. 21 No. 9, pp. 2025-2029 (1993).
Bernath et al., "Directed Evolution of Protein Inhibitors of DNA-Nucleases by in Vitro Compartmentalization (IVC) and Nano-Droplet Delivery," Journal of Molecular Biology, vol. 345, pp. 1015-1026 (2005).

(56) References Cited

OTHER PUBLICATIONS

Bentolila et al., "Constituitive Expression of Terminal Deoxynucleotidyl Transferase in Transgenic Mice is Sufficient for N Region Diversity to Occur at Any Ig Locus Throughout B Cell Differentiation," The Journal of Immunology, vol. 158, pp. 715-723 (1997).
Binz et al., "Engineering Novel Binding Proteins from Nonimmunoglobulin Domains," Nature Biotechnology, vol. 23, No. 10, pp. 1257-1268 (2005).
Browman et al., "The SPFH Domain-Containing Proteins: More Than Lipid Raft Markers," Trends in Cell Biology, vol. 17, No. 8, pp. 394-402 (2007).
Carra et al., "Variation of the Half-Site Organization and DNA Looping by AraC Protein," The EMBO Journal, vol. 12, No. 1, pp. 35-44 (1993).
Casillas et al., "RAG-1 and RAG-2 Gene Expression and V(D),J Recombinase Activity are Enhanced by Protein Phosphatase 1 and 2A Inhibition in Lymphocyte Cell Lines," Molecular Immunology, vol. 32, No. 3, pp. 167-175 (1995).
Certo et al., "Coupling Endonucleases with DNA End-Processing Enzymes to Drive Gene Disruption." Nature Methods, vol. 9, No. 10, pp. 973-975 (2012).
Chatterjee et al., "The GPI-Anchor and Protein Sorting," Cellular and Molecular Life Sciences, vol. 58, pp. 1969-1987 (2001).
Chen et al., "Immunoglobulin G Expression in Carcinomas and Cancer Cell lines," The FASEB Journal, vol. 21, pp. 2931-2938 (2007).
Colas et al., "Genetic Election of Peptide Aptamers that Recognize and Inhibit Cyclin-Dependent Kinase 2," Letters to Nature, vol. 380, No. 6574, pp. 548-550 (1996).
Cowell et al., "Computational Tools for Understanding Sequence Variability in Recombination Signals," Immunological Reviews, vol. 200, pp. 57-69 (2004).
Dudley et al., "Mechanism and Control of V(D)J Recombination Versus Class Switch Recombination: Similarities and Differences," Advances in Immunology, vol. 86, pp. 43-112 (2005).
Engler et al., "Influence of CpG Methylation and Target Spacing on V(D)J Recombination in a Transgenic Substrate," Molecular and Cellular Biology, vol. 13, No. 1, pp. 571-577 (1993).
Fanning et al., "Mouse RSS Spacer Sequences Affect the Rate of V(D)J Recombination," Immunogenetics, vol. 44, pp. 146-150 (1996).
Ford et al., "Fusion Tails for the Recovery and Purification of Recombinant Proteins," Protein Expression and Purification, vol. 2, pp. 95-107 (1991).
Frederickson et al., "A Rationally Designed Agonist Antibody Fragment that Functionally Mimics Thrombopoietin," Proceeding s of the National Academy of Sciences, vol. 103, No. 39, pp. 14307-14312 (2006).
Fukushige et al., "Genomic Targeting with a Positive-Selection lox Integration Vector Allows Highly Reproducible Gene Expression in Mammalian Cells," Proceedings of the National Academy of Sciences, vol. 89, pp. 7905-7909 (1992).
Gauss et al., "V(D)J Recombination Activity in Human Hematopoietic Cells: Correlation with Developmental Stage and Genome Stability," European Journal of Immunology, vol. 28, pp. 351-358 (1998).
Gebauer et al., "Engineered Protein Scaffolds as Next-Generation Antibody Therapeutics," Current opinion in Chemical Biology, vol. 13, pp. 245-255 (2009).
Griffiths et al., "Isolation of High Affinity Human Antibodies Directly from a Large Synthetic Repertoires," The EMBO Journal, vol. 13, No. 14, pp. 3245-3260 (1994).
Guzman et al., "Tight Regulation, Modulation, and High-Level Expression by Vectors Containing the Arabinose P BAD Promoter," Journal of Bacteriology, vol. 177, No. 14, pp. 4121-4130 (1995).
Hackel et al., "Picomolar Affinity Fibronectin Domains Engineered Utilizing Loop Length Diversity, Recursive Mutagenesis, and Loop Shuffling," Journal of Molecular Biology vol. 381, pp. 1238-1252 (2008).
Haldimann et al., "Use of New Methods for Construction of Tightly Regulated Arabinose and Rhamnose Promoter Fusion in Studies of the *Escherichia coli* Phosphate Regulon," Journal of Bacteriology, vol. 180, No. 5, pp. 1277-1286 (1998).
Harder, "Lipid Raft Domains and Protein Networks in T-Cell Receptor Signal Transduction," Current Opinion in Immunology, vol. 16, pp. 353-359 (2014).
Hattori et al., "Grafting of Material-Binding Function Into Antibodies Functionalization by Peptide Grafting," Biochemical and Biophysical Research Communications, vol. 365, pp. 751-757 (2008).
Hattori et al., "High Affinity Anti-inorganic Material Antibody Generation by Integrating Graft and Evolution Technologies" The Journal of Biological Chemistry, vol. 285, No. 10, pp. 7784-7793 (2010).
Hayashi et al., "The Potential Role of Sigma-1 Receptors in Lipid Transport and Lipid Raft Constitution in the Brain: Implication for Drug Abuse," Life Sciences, vol. 77, pp. 1612-1624 (2005).
Heckmamm et al., "Design and Chemical Synthesis of Integrin Ligands," Methods in Enzymology, vol. 426, pp. 463-503 (2007).
Heese et al., "V(D)J Recombination: A Functional Definition of the Joining Signals," Genes & Development, vol. 3, pp. 1053-1061 (1999).
Heuck et al., "Pore-Forming Protein Structure Analysis in Membranes Using Multiple Independent Fluorescence Techniques," Cell Biochemistry and Biophysics, vol. 36, pp. 89-101 (2002).
Hikida et al., "Reexpression of RAG-1 and RAG-2 Genes in Activated Mature Mouse B Cells," Science, vol. 274, No. 5295, pp. 2092-2094 (1996).
Hikida et al., "Rearrangement of λ Light Chain Genes in Mature B Cells In Vitro and In Vitro. Function of Reexpressed Recombination-activating Gene (RAG) Products," The Journal Experimental Medicine, vol. 187, No. 5, pp. 795-799 (1998).
Holland et al., "The T-Cell Receptor is not Hardwired to Engage MHC Ligands," Proceedings of the National Academy of Sciences, pp. E3111-E3118 (2012).
Holowka et al., "Fcε RI as a Paradigm for a Lipid Raft-Dependent Receptor in Hematopoietic Cells," Immunology, vol. 13, pp. 99-105 (2001).
Hooper, "Determination of Glycosyl-Phosphatidylinositol Membrane Protein Anchorage," Proteomics, vol. 1, pp. 748-735 (2001).
Hopp et al., "A Short Polypeptide Marker Se uen Useful for Recombinant Protein Identification and Purification," Biotechnology, vol. 6, pp. 1204-1210 (1988).
Ignatovich et al., "The Creation of Diversity in the Human Immunoglobulin V Repertoire," Journal of Molecular Biology, vol. 268, pp. 69-77 (1997).
Jones et al., "Replacing the Complementanty Determinng Regions in a Human Antibody with Those from a Mouse," Letters to Nature, vol. 321, pp. 522-525 (1986).
Kaczmarczyk et al., "A Single Vector Containing Modified cre Recombinase and LOX Recombination Sequences for Inducible Tissue-Specific Amplification of Gene Expression," Nucleic Acids Research vol. 29, No. 12 e56, pp. 1-13 (2001).
Kallenbach et al., "Three Lymphoid-Specific Factors Account for all Junctional Diversity Characteristic of Somatic Assembly of T-cell Receptor and Immunoglobulin Genes," Proceedings of the National Academy of Sciences, vol. 89, pp. 2799-2803 (1992).
Koiwai et al., "Analysis of Human Terminal Deoxynucleotidyl Transferase cDNA Expressible in Mammalian Cells," Biochemical and Biophysical Research Communications, vol. 144, No. 1 pp. 185-190 (1987).
Kondo et al., "Simultaneous on/off Regulation of Transgenes Located on a Mammalian Chromosome with Cre-Expressing Adenovirus and a Mutant loxP," Nucleic Acids Research vol. 31, No. 14 e76, pp. 1-10 (2003).
Lantelme et al., "An in vitro Model of T Cell Receptor Revision in Mature Human CD8+ T Cells," Molecular Immunology, vol. 45, pp. 328-337 (2008).
Larijani et al., "The Role of Components, of Recombination Signal Sequences in Immunoglobulin Gene Segment Usage: a V81x Model," Nucleic Acids Research, vol. 27, No. 11 (1999).

(56) References Cited

OTHER PUBLICATIONS

Lee et al., "A Functional Analysis of Spacer of V(D)J Recombination Signal Sequences," PLoS Biology, vol. 1, issue 1, pp. 56-69 (2003).

Lipovsek et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, vol. 368, pp. 1024-1041 (2007).

Lutz et al., "Independent and Tight Regulation of Transcriptional Units of *Escherichia coli* via the LacR/O, the TetR/O and AraC/I1-I2 Regulatory Elements," Nucleic Acids Research, vol. 25, No. 6, pp. 1203-1210 (1997).

* cited by examiner

E188 PARTIAL SEQUENCE gccgccaccatggagtttgggctgagctggcttttcttgtggctattttaaaaggtgtccagtgttacccatacgatgttccagattacgct
tgtgccccctcacagtggtagtactccactgtctgggtgtacaaaaacctccctgcacgcctctctaacctcacaattctgtggcggccgc
gccgccaccatgattgaacaagatggattgcacgcaggttctccggccgcttgggtggagaggctattcggctatgactgggcacaa
cagacaatcggctgctctgatgccgccgtgttccggctgtcagcgcaggggcgcccggttcttttgtcaagaccgacctgtccggtgc
cctgaatgaactgcaggacgaggcagcgcggctatcgtggctggccacgacgggcgttccttgcgcagctgtgctcgacgttgtcac
tgaagcgggaagggactggctgctattgggcgaagtgccggggcaggatctcctgtcatctcaccttgctcctgccgagaaagtatcc
atcatggctgatgcaatgcggcggctgcatacgcttgatccggctacctgcccattcgaccaccaagcgaaacatcgcatcgagcga
gcacgtactcggatggaagccggtcttgtcgatcaggtgagtacaggaggtggagagtacgcgtaacacttaagcgtctctccaagtg
caaagggacaggaggttttgttaagggctgtatcactgtgagccagttccagtgcggctccggctaccacagtgatacagcccttaac
aaaaaccccctactgcaacctggcggtaagagacgtccggaggccagcccttctcatgttcagagaacatggttaactggttaagtcatg
tcgtcccacaggatgatctggacgaagagcatcaggggctcgcgccagccgaactgttcgccaggctcaaggcgcgcatgcccga
cggcgaggatctcgtcgtgacccatggcgatgcctgcttgccgaatatcatgtggaaaatggccgcttttctggattcatcgactgtgg
ccggctgggtgtggcggaccgctatcaggacatagcgttggctacccgtgatattgctgaagagcttggcggcgaatgggctgaccg
cttcctcgtgctttacggtatcgccgctcccgattcgcagcgcatcgccttctatcgccttcttgacgagttcttctgagtcgactgcagga
gtcccactgcaccccccctcccagtcttctctgtccaggcaccaggccaggtatctgggtgtgcagccggcctgggtctggcctgagg
ccacaagcccgggggtctgtgtggctggggacagggacgccggctgcctctgctctgtgcttgggccatgtgacccattcgagtgtc
ctgcacgggcacaggttttgtacacccagacagtggagtactaccactgtgggctactgcatcagccagagatgggtgtgcgacgg
ggagaatgattgcgaggacggcagcgacgaggccaattgtgccggctctgtgcctaccgagcccaaatcttgtgacaaaactcacac
atgcccaccgtgcccagcacctgaactcctgggggaccgtcagtcttcctcttccccccaaaacccaaggacaccctcatgatctcta
gaacccctgaggtcacatgcgtggtggtggacgtgagccacgaagaccctgaggtcaagttcaactggtacgtggacggcgtggag
gtgcataatgccaagacaaagccgcgggaggagcagtacaacagcacgtaccgtgtggtcagcgtcctcaccgtcctgcaccagga
ctggctgaatggcaaggagtacaagtgcaaggtgtccaacaaagcccctcccagcccccatcgagaaaaccatctccaaagccaaag
ggcagccccgagaaccacaggtgtacaccctgcccccatcccgggatgagctgaccaagaaccaggtcagcctgacctgcctggt
caaaggcttctatcccagcgacatcgccgtggagtgggagagcaatgggcagccggagaacaactacaagaccacgcctcccgtg
ctggactccgacggctccttcttcctctacagcaagctcaccgtggacaagtctagatggcagcaggggaacgtcttctcatgctccgt
gatgcatgaggctctgcacaaccactacacgcagaagagcctctccctgtctccgggcaaactggctctcattgtcctgggcggcgtg
gctggcctgctgctgtttattgggctgggcatcttcttttgtgtccggtgtcggcataggaggcgccaaggaggtggcggatctggagg
gggaggatctggagggggctcaggatcaggggaggatctggaggcggatca

[SEQ ID NO:28]

FIG. 1

E189 PARTIAL SEQUENCE gccgccaccatggagtttgggctgagctggcttttcttgtggctattttaaaaggtgtccagtgttacccatacgatgttccagattacgct
tgcctgccccacagtggtagtactccactgtctgggtgtacaaaaacctccctgcacgcctctctaacctcacaattctgtggcggccgc
gccgccaccatgattgaacaagatggattgcacgcaggttctccggccgcttgggtggagaggctattcggctatgactgggcacaa
cagacaatcggctgctctgatgccgccgtgttccggctgtcagcgcaggggcgcccggttctttttgtcaagaccgacctgtccggtgc
cctgaatgaactgcaggacgaggcagcgcggctatcgtggctggccacgacgggcgttccttgcgcagctgtgctcgacgttgtcac
tgaagcgggaagggactggctgctattgggcgaagtgccggggcaggatctcctgtcatctcaccttgctcctgccgagaaagtatcc
atcatggctgatgcaatgcggcggctgcatacgcttgatccggctacctgcccattcgaccaccaagcgaaacatcgcatcgagcga
gcacgtactcggatggaagccggtcttgtcgatcaggtgagtacaggaggtggagagtacgcgtaacacttaagcgtctctccaagtg
caaagggacaggaggttttgttaagggctgtatcactgtggaccagttcagatgcggcaacggccagtgcatcccctggattgggt
gtgcgacggcgtgaacgactgccccgattccgatgaggaaggctgcccccctagaacctgtgccctagccagcacagtgatacag
cccttaacaaaaaccctactgcaacctggcggtaagagacgtccggaggccagcccttctcatgttcagagaacatggttaactggtt
aagtcatgtcgtcccacaggatgatctggacgaagagcatcaggggctcgcgccagccgaactgttcgccaggctcaaggcgcgca
tgcccgacggcgaggatctcgtcgtgacccatggccgatgcctgcttgccgaatatcatggtggaaaatggccgcttttctggattcatc
gactgtggccggctgggtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgacgagttcttctgagtcga
ctgcaggagtcccactgcaccccctcccagtcttctctgtccaggcaccaggccaggtatctggggtgtgcagccggcctgggtctg
gcctgaggccacaagcccgggggtctgtgtggctggggacagggacgccggctgcctctgctctgtgcttgggccatgtgacccatt
cgagtgtcctgcacggggcacaggtttttgtacacccagacagtggagtactaccactgtgttccagtgcggctccggctactgcatcag
ccagagatgggtgtgcgacggggagaatgattgcgaggacggcagcgacgaggccaattgtgccggctctgtgcctaccgagccc
aaatcttgtgacaaaactcacacatgcccaccgtgcccagcacctgaactcctgggggggaccgtcagtcttcctcttcccccaaaacc
caaggacaccctcatgatctctagaacccctgaggtcacatgcgtggtggtggacgtgagccacgaagaccctgaggtcaagttcaa
ctggtacgtggacggcgtggaggtgcataatgccaagacaaagccgcgggaggagcagtacaacagcacgtaccgtgtggtcagc
gtcctcaccgtcctgcaccaggactggctgaatggcaaggagtacaagtgcaaggtgtccaacaaagccctcccagcccccatcga
gaaaaccatctccaaagccaaagggcagccccgagaaccacaggtgtacaccctgccccatcccgggatgagctgaccaagaac
caggtcagcctgacctgcctggtcaaaggcttctatcccagcgacatcgccgtggagtgggagagcaatgggcagccggagaacaa
ctacaagaccacgcctcccgtgctggactccgacggctccttcttcctctacagcaagctcaccgtggacaagtctagatggcagcag
gggaacgtcttctcatgctccgtgatgcatgaggctctgcacaaccactacacgcagaagagcctctccctgtctccgggcaaactgg
ctctcattgtcctgggcggcgtggctggcctgctgctgtttattgggctgggcatcttcttttgtgtccggtgtcggcataggaggcgcca
aggaggtggcggatctggaggggggaggatctggaggggggctcaggatcaggggggaggatctggaggcggatca

[SEQ ID NO:29]

FIG. 2

A.
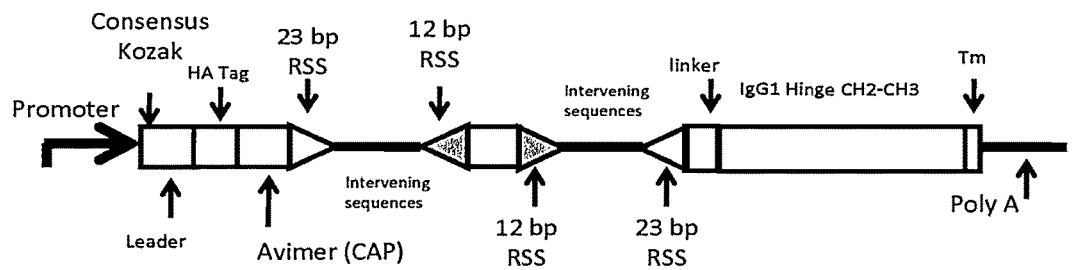
B.
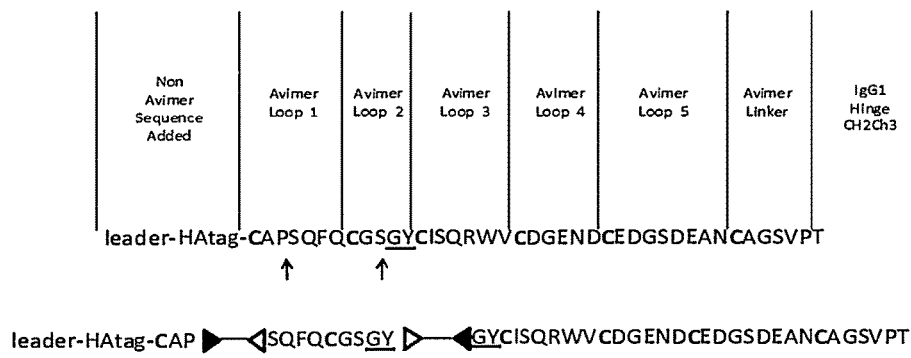
- Bold residues indicate conserved Cystiene Amino Acids
- Underlined Amino Acids indicate flanking residues which were duplicated in the mutator construct
- Arrows indicate location of inserted RSS cassette
FIG. 3A,B

C.

A.

| +1 | S | Q | F | C | G | S | G | Y |
|---|---|---|---|---|---|---|---|---|
| 1 | AGCCAGTTCC AGTGCGGCTC CGGCTAC |||||||||
|   | TCGGTCAAGG TCACGCCGAG GCCGATG |||||||||

B.

| +3 |   | Q | P | V | C | V | R | L | R | L | L |
|---|---|---|---|---|---|---|---|---|---|---|---|
| +2 |   | T | A | S | L | C | A | A | P | A | T |
| +1 | Y | S | Q | F | V | C | G | S | G | Y | Y |
| 1 | TACAGCCAGT TTGTGTGCGG CTCCGGCTAC TAC ||||||||||
|   | ATGTCGGTCA AACACACGCC GAGGCCGATG ATG ||||||||||

tccgatgtgcccagggacctggaagtggtggccgccacacctaccagcctgctgatctcttgggatgcccctgccgtgaccgtgcgg
tactacagaatcacctacggcgagacaggcggcaacagccccgtgcaggagtttacagtgcccggcagcaagagcaccgccacca
tctctggactgaagcccggcgtggactacaccatcaccgtgtacgccgtgacaggcagaggcgacagccctgccagcagcaagcc
catcagcatcaactaccggacc

[SEQ ID NO:34]

B.

SDVPRDLEVVAATPTSLLISWDAPAVTVRYYRITYGETGGNSPVQEFTVPGSKSTATI
SGLKPGVDYTITVYAVTGRGDSPASSKPISINYRT

[SEQ ID NO:39]

C.

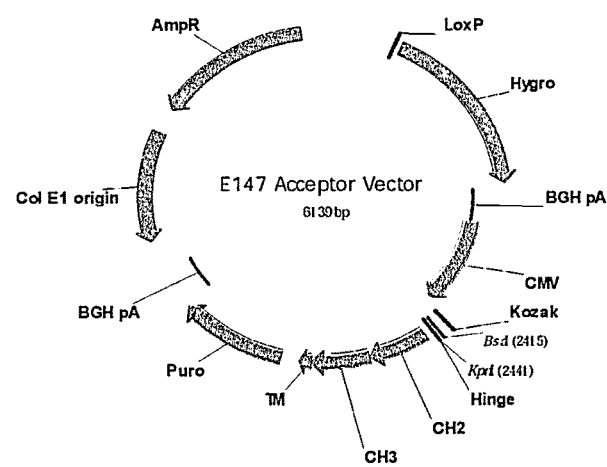

ctaaattgtaagcgttaatatttgttaaaattcgcgttaaattttgttaaatcagctcatttttaaccaataggccgaaatcggcaaaatccc
ttataaatcaaaagaatagaccgagatagggttgagtggccgctacagggcgctcccattcgccattcaggctgcgcaactgttggga
agggcgtttcggtgcgggcctcttcgctattacgccagctggcgaaaggggatgtgctgcaaggcgattaagttgggtaacgccag
ggttttcccagtcacgacgttgtaaaacgacggccagtgagcgcgacgtaatacgactcactatagggcgaattggcggaaggccgt
caaggcctaggcgcgcctgaataacttcgtatagcatacattatagcaatttatcgaaaaagcctgaactcaccgcgacatccgtggag
aaattcctcatcgaaaaattcgactccgtgtccgatctcatgcagctgtccgagggcgaggagagtagagcattctcattcgatgtggg
cgggagaggctacgtgctgagagtgaactcttgtgccgacggcttctacaaggaccgatacgtctaccggcattttgcttccgccgctc
tgcctattccagaagtcctggacattggggagtttagcgagtccctcacttactgtattagccggcgagcccagggagtgacactccag
gatctgcctgaaactgaactgcctgctgtgctccagcctgtcgctgaggcaatggatgctattgctgctgccgatctgagtcagactagc
ggattcggcccatttggaccccagggcattggccagtacacaacatggcgagacttcatctgtgctatcgccgatcctcacgtgtacca
ttggcagactgtgatggacgatactgtgtctgcttctgtggcacaggcactcgacgaactcatgctgtgggctgaggactgtcctgaagt
gagacatctggtccatgccgattttggctccaacaatgtgctcaccgataacgggagaatcactgccgtgatcgactggagcgaggca
atgtttggcgattcccagtacgaagtggccaacatcttcttttggcggccttggctggcttgtatggaacagcagacccggtactttgaac
ggcgccaccctgagctggctgggagtcctagactgagagcctacatgctccgaattggcctggatcagctctaccagtcactggtgga
tggcaatttcgacgatgctgcttgggcacaggggcgctgtgatgctattgtccgatccggcgctggaactgtggggagaacacagatc
gctaggagatccgctgctgtctggaccgatggatgtgtggaagtgctggccgatagtggaaaccggaggccttcaacccgaccccg
ggcaaaggagtaatgaccgtttaaacccgctgatcagcctcgactgtgccttctagttgccagccatctgttgtttgccccctcccccgtgc
cttccttgaccctggaaggtgccactcccactgtcctttcctaataaaatgaggaaattgcatcgcattgtctgagtaggtgtcattctattct
gggggtggggtggggcaggacagcaaggggggaggattgggaagacaatagcaggcatgctggggatgcggtgggctctatgg
ggatcccgcgttgacattgattattgactagttattaatagtaatcaattacggggtcattagttcatagcccatatatggagttccgcgttac
ataacttacggtaaatggcccgcctggctgaccgcccaacgacccccgcccattgacgtcaataatgacgtatgttcccatagtaacgc
caatagggactttccattgacgtcaatgggtggagtatttacggtaaactgcccacttggcagtacatcaagtgtatcatatgccaagtac
gccccctattgacgtcaatgacggtaaatggcccgcctggcattatgcccagtacatgaccttatgggactttcctacttggcagtacatc
tacgtattagtcatcgctattaccatggtgatgcggttttggcagtacatcaatgggcgtggatagcggtttgactcacggggatttccaa
gtctccacccccattgacgtcaatgggagtttgttttggcaccaaaatcaacgggactttccaaaatgtcgtaacaactccgccccattgac
gcaaatgggcggtaggcgtgtacggtgggaggtctatataagcagagctctctggctaactagagaacccactgcttactgctcgacg
atctgatcaagagacaggataaggagccgccaccatggagtttgggctgagctggcttttcttgtggctattttaaaaggtgtccagtgt
agagaccggaagagattggtaccgagcccaaatcttgtgacaaaactcacacatgcccaccgtgcccagcacctgaactcctgggg
ggaccgtcagtcttcctcttccccccaaaacccaaggacaccctcatgatctctagaaccccctgaggtcacatgcgtggtggtggacgt
gagccacgaagaccctgaggtcaagttcaactggtacgtggacggcgtggaggtgcataatgccaagacaaagccgcgggagga
gcagtacaacagcacgtaccgtgtggtcagcgtcctcaccgtcctgcaccaggactggctgaatggcaaggagtacaagtgcaaggt
gtccaacaaagcccctcccagcccccatcgagaaaaccatctccaaagccaaagggcagccccgagaaccacaggtgtacaccctg
cccccatcccgggatgagctgaccaagaaccaggtcagcctgacctgcctggtcaaaggcttctatcccagcgacatcgccgtggag
tgggagagcaatgggcagccggagaacaactacaagaccacgcctcccgtgctggactccgacggctccttcttcctctacagcaag
ctcaccgtggacaagtctagatggcagcaggggaacgtcttctcatgctccgtgatgcatgaggctctgcacaaccactacacgcaga
agagcctctccctgtctccgggcaaactggctctcattgtcctgggcggcgtggctggcctgctgctgtttattgggctgggcatcttcttt
tgtgtccggtgtcggcataggaggcgccaaggaggtggcggatctggagggggaggatctggagggggctcaggatcaggggga
ggatctggaggcggatcaactgagtacaaacccactgtgaggctcgctactagagatgatgtgcctagagctgtccgaactctggctg
ctgccttcgccgattaccctgccactcgccataccgtcgatcccgatcgccacattgaacgagtcaccgaactccaggagctgtttctca
ctagagtcgggctggatattggcaaagtctgggtggccgatgacggagccgctgtcgctgtgtggactacacctgagtctgtggagg
ctggcgccgtgtttgctgaaattggacctcggatggctgaactgtctggatctcgactggctgcccagcagcagatggagggactgct
ggcacccatagaccaaaggaacctgcctggtttctggcaactgtgggagtgtcacccgatcatcagggcaaaggactgggatctgc
cgtggtgctccctggcgtggaggccgctgaacgagctggcgtccccgctttctcgaaacttctgccccccgaaatctcccttctacga
acgactgggattcactgtcaccgccgatgtcgaagtgcctgaggggcctagaacatggtgtatgacccggaaacccggagcttaacc

gtttaaacccgctgatcagcctcgactgtgccttctagttgccagccatctgttgtttgcccctcccccgtgccttccttgaccctggaagg
tgccactcccactgtcctttcctaataaaatgaggaaattgcatcgcattgtctgagtaggtgtcattctattctggggggtggggtgggg
caggacagcaaggggggaggattgggaagacaatagcaggcatgctggggatgcggtgggctctatggctcgagttaattaactggc
ctcatgggccttccgctcactgcccgctttccagtcgggaaacctgtcgtgccagctgcattaacatggtcatagctgtttccttgcgtatt
gggcgctctccgcttcctcgctcactgactcgctgcgctcggtcgttcgggtaaagcctggggtgcctaatgagcaaaaggccagcaa
aaggccaggaaccgtaaaaaggccgcgttgctggcgtttttccataggctccgcccccctgacgagcatcacaaaaatcgacgctca
agtcagaggtggcgaaacccgacaggactataaagataccaggcgtttccccctggaagctccctcgtgcgctctcctgttccgaccc
tgccgcttaccggatacctgtccgcctttctcccttcgggaagcgtggcgctttctcatagctcacgctgtaggtatctcagttcggtgtag
gtcgttcgctccaagctgggctgtgtgcacgaaccccccgttcagcccgaccgctgcgccttatccggtaactatcgtcttgagtccaa
cccggtaagacacgacttatcgccactggcagcagccactggtaacaggattagcagagcgaggtatgtaggcggtgctacagagtt
cttgaagtggtggcctaactacggctacactagaagaacagtatttggtatctgcgctctgctgaagccagttaccttcggaaaaagagt
tggtagctcttgatccggcaaacaaaccaccgctggtagcggtggtttttttgtttgcaagcagcagattacgcgcagaaaaaaaggat
ctcaagaagatcctttgatcttttctacggggtctgacgctcagtggaacgaaaactcacgttaagggattttggtcatgagattatcaaaa
aggatcttcacctagatccttttaaattaaaaatgaagttttaaatcaatctaaagtatatatgagtaaacttggtctgacagttaccaatgctt
aatcagtgaggcacctatctcagcgatctgtctatttcgttcatccatagttgcctgactccccgtcgtgtagataactacgatacgggag
ggcttaccatctggccccagtgctgcaatgataccgcgagaaccacgctcaccggctccagatttatcagcaataaaccagccagcc
ggaagggccgagcgcagaagtggtcctgcaactttatccgcctccatccagtctattaattgttgccgggaagctagagtaagtagttc
gccagttaatagtttgcgcaacgttgttgccattgctacaggcatcgtggtgtcacgctcgtcgtttggtatggcttcattcagctccggttc
ccaacgatcaaggcgagttacatgatcccccatgttgtgcaaaaaagcggttagctccttcggtcctccgatcgttgtcagaagtaagtt
ggccgcagtgttatcactcatggttatggcagcactgcataattctcttactgtcatgccatccgtaagatgcttttctgtgactggtgagta
ctcaaccaagtcattctgagaatagtgtatgcggcgaccgagttgctcttgcccggcgtcaatacgggataataccgcgccacatagca
gaactttaaaagtgctcatcattggaaaacgttcttcggggcgaaaactctcaaggatcttaccgctgttgagatccagttcgatgtaacc
cactcgtgcacccaactgatcttcagcatcttttactttcaccagcgtttctgggtgagcaaaaacaggaaggcaaaatgccgcaaaaaa
gggaataagggcgacacgaaatgttgaatactcatactcttcctttttcaatattattgaagcatttatcagggttattgtctcatgagcgg
atacatatttgaatgtatttagaaaaataaacaaataggggttccgcgcacatttccccgaaaagtgccac

[SEQ ID NO:35]

10Fn3 bipartite 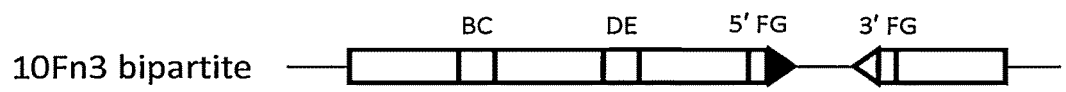

B.

```
                FG loop (Hackel 2010)
                                            23-bp RSS
ACAGGCAGA  GGCGATAGCCACAGTGGTAGTACTCCA  CTGTCTGGGTGTACAAAAACCTCCCTG
TGTCCGTCT  CCGCTATCGGTGTCACCATCATGAGGT  GACAGACCCACATGTTTTTGGAGGGAC
```

C.

```
                                          FG loop (Hackel 2010)
                                                                10Fn3
GACAGGA  GGTTTTTGTTAAGGGCTGTATCACTGT  GCCTGCCAGCAGCAAGCCCATCAGCAT
CTGTCCT  CCAAAAACAATTCCCGACATAGTGACA  CGGACGGTCGTCGTTCGGGTAGTCGTA
                  12-bp RSS
```

tccgatgtgcccagggacctggaagtggtggccgccacacctaccagcctgctgatctcttgggatgcccctgccgtgaccgtgcgg
tactacagaatcacctacggcgagacaggcggcaacagccccgtgcaggagtttacagtgcccggcagcaagagcaccgccacca
tctctggactgaagcccggcgtggactacaccatcaccgtgtacgccgtgacaggcagaggcgatag**ccacagtggtagtactcca
ctgtctgggtgtacaaaaacc**tccctgcacgcctctctaacctcacaattctgtggcggccgctttgtagccagaccctcggtcaactg
gatgtcacaactggcacctgagattggaaacataaaaacaaatattcttactattaatcatgttatcagagaacttccctgaagttccagtc
agtactgtgactagctaattagtcagttacttaagcgtctatccaagtgcaaagggacaggaggttttgttaagggctgtatcactgtg
cctgccagcagcaagcccatcagcatcaactaccggacc

[SEQ ID NO:37]

B.

tccgatgtgcccagggacctggaagtggtggccgccacacctaccagcctgctgatctcttgggatgcccctgccgtgaccgtgcgg
tactacagaatcacctacggcgagacaggcggcaacagccccgtgcaggagtttacagtgcccggcagcaagagcaccgccacca
tctctggactgaagcccggcgtggactacaccatcaccgtgtacgccgtgacagg**ccacagtggtagtactccactgtctgggtgt
acaaaaacc**tccctgcacgcctctctaacctcacaattctgtggcggccgctttgtagccagaccctcggtcaactggatgtcacaact
ggcacctgagattggaaacataaaaacaaatattcttactattaatcatgttatcagagaacttccctgaagttccagtcagtactgtgact
agctaattagtcagttacttaagcgtctatccaagtgcaaagggacaggaggttttgttaagggctgtatcactgtgggcagaggcg
acagccctgccagcagcaagcacagtgatacagcccttaacaaaaacccctactgcaacctggcggtaatagacgtccggaagc
acactggctgagtaaattcctagtgttctccatccttacctcggagccagagtagcaggagccactagccagcttgggtcttcctatcgc
gagtcgtattaatttcgataagccagcaagcagtgggttctctagttagccagctgcctcctttctctgggcccagcgtcctctgtcctgg
agctgggagataatgtccgggggctccttggtctgcgctgggcaaagggtgggcagagtcatgcttgtgctggggacaaaatgacct
tgggacacggtcgacgggctggctgccacggccggcccgggacagtcggagagtca**ggttttgtacacccagacagtggagta
ctaccactgtg**aagcccatcagcatcaactaccggacc

[SEQ ID NO:38]

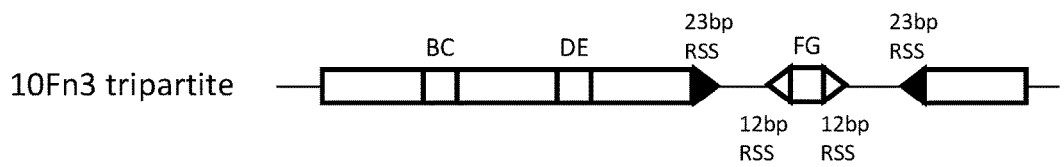

B.

```
                                                        23bp-RSS
        Repeat
GTGTACGCCGTGACAGGC  CACAGTGGTAGTACTCCACTGTCTGGGTGTACAAAAACCT CCC
CACATGCGGCACTGTCCG  GTGTCACCATCATGAGGTGACAGACCCACATGTTTTTGGA GGG
```

C.

```
                                                              12-bp RSS
                                10Fn3
                                FG loop
                    A  E  A  T  A  L  P  A  A  S
                 G  R  G  D  S  P  A  S  S  K
              Q  R  R  Q  P  C  Q  Q  Q  A
GG AGGTTTTTGTTAAGGGCTGTATCAC TGTGGGCAGAGGCGACAGCCCTGCC AGCAGCAAGCACAGTGATACAGCCC TTAACAAAAACCCC
CC TCCAAAAACAATTCCCGACATAGTG ACACCCGTCTCCGCTGTCGGGACGG TCGTCGTTCGTGTCACTATGTCGGG AATTGTTTTTGGGG
   9mer                    7mer
                    12-bp RSS
```

D.

```
                                                           Repeat
                                                       10Fn3
GGAGAGTCAGGT TTTTGTACACCCAGACAGTGGAGTA CTACCACTGTGAAGCCCATCAGCAT
CCTCTCAGTCCA AAAACATGTGGGTCTGTCACCTCAT GATGGTGACACTTCGGGTAGTCGTA
                    23-bp RSS
```

FIG. 11 A, B, C, D

A.
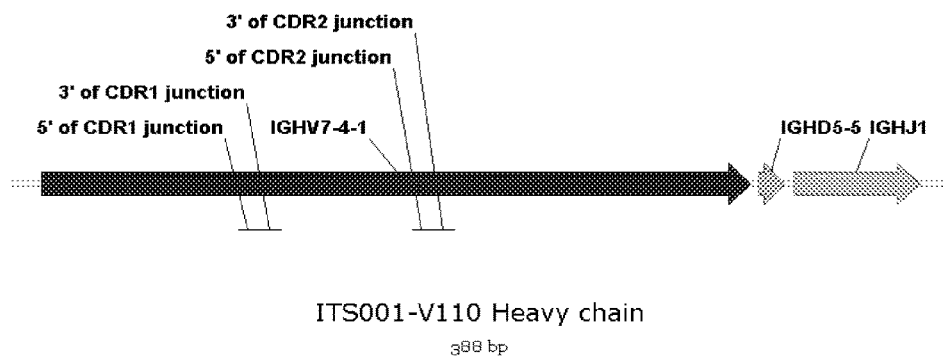
ITS001-V110 Heavy chain
388 bp
B.
```
5' of CDR1 junction
       3' of CDR1 junction
                                    IGHV7-4-1
GCTACACC TTCACCAG CTACGCCA TGAACTGG GTCCG
CGATGTGG AAGTGGTC GATGCGGT ACTTGACC CAGGC
```
C.
```
5' of CDR2 junction
       3' of CDR2 junction
                                    IGHV7-4-1
GGATCAAC ACCAACAC CGGCAACC CCACCTAC GCCCAGGG CTT
CCTAGTTG TGGTTGTG GCCGTTGG GGTGGATG CGGGTCCC GAA
```
FIG. 13 A, B, C A.
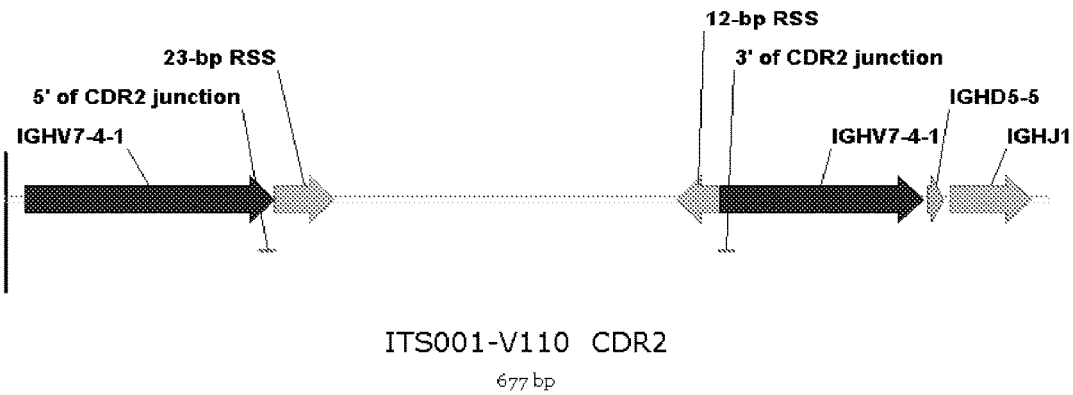
ITS001-V110 CDR2
677 bp
B.
```
                                                          23-bp RSS
IGHV7-4-1
         5' of CDR2 junction
TGGGCTGGATCAAC ACCAACCACAGTGG TAGTACTCCACTGT CTGGGTGTACAAAA ACCTC
ACCCGACCTAGTTG TGGTTGGTGTCACC ATCATGAGGTGACA GACCCACATGTTTT TGGAG
```
C.
```
                                              3' of CDR2 junction
AGGTTTTTGTTAAG GGCTGTATCACTGT GACCGGCAACCCCA CCTA
TCCAAAAACAATTC CCGACATAGTGACA CTGGCCGTTGGGGT GGAT
              12-bp RSS
```
FIG. 14 A, B, C

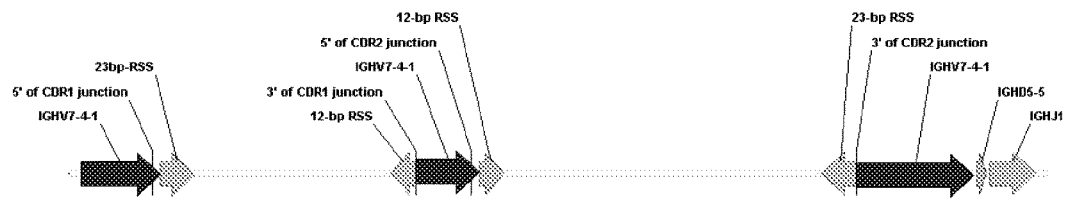
FIG. 15 A, B, C, D

E.

```
                                                          IGHV7.4.1
                                               3' of CDR2 junction
TCAGGTTTTTGTAC ACCCAGACAGTGGA GTACTACCACTGTG ACCGGCAACCCCAC CTACGCCCAGGGCT
AGTCCAAAAACATG TGGGTCTGTCACCT CATGATGGTGACAC TGGCCGTTGGGGTG GATGCGGGTCCCGA
                          23-bp RSS
```

caggtgcagctggtgcagagcggcagcgagctgaagaaacctggcgcctccgtgaaggtgtcctgcaaggccagcggctacacct
tcaccagctacgccatgaactgggtccgccaggccccaggccagggactggaatggatgggctggatcaacaccaacaccggc
aaccccacctacgcccagggcttcaccggc**agattcgtgttcagcttcgacaccagcgtgtccaccgcctacctgcagatctgtagc
ctgaaggccgaggacaccgccgtgtattactgtgcgagagggacagctatggtacgggctgaatacttccagcactggggccaggg
caccctggtcaccgtgtcctcag

[SEQ ID NO:3]

B.

caggtgcagctggtgcagagcggcagcgagctgaagaaacctggcgcctccgtgaaggtgtcctgcaaggccagcggctacacct
tcaccagctacgccatgaactgggtccgccaggccccaggccagggactggaatggatgggctggatcaacaccaac**cacagtgg
tagtactccactgtctgggtgtacaaaaacct**ccctgcacgcctctctaacctcacaattctgtggcggccgctttgtagccagaccct
cggtcaactggatgtcacaactggcacctgagattggaaacataaaaacaaatattcttactattaatcatgttatcagagaacttccctga
agttccagtcagtactgtgactagctaattagtcagttacttaagcgtctatccaagtgcaaagggacagga**ggttttgttaagggctg
tatcactgt**accggcaaccccacctacgcccagggcttcaccggcagattcgtgttcagcttcgacaccagcgtgtccaccgccta
cctgcaaatctgtagcctgaaggccgaggacaccgccgtgtattactgtgcgagagggacagctatggtccgggctgaatacttccag
cactggggccagggcaccctggtcaccgtgtcctcag

[SEQ ID NO:4]

C.

caggtgcagctggtgcagagcggcagcgagctgaagaaacctggcgcctccgtgaaggtgtcctgcaaggccagcggctacacct
tcaccagccacagtggtagtactccactgtctgggtgtacaaaaacctccctgcacgcctctctaacctcacaattctgtggcggcc
gctttgtagccagaccctcggtcaactggatgtcacaactggcacctgagattggaaacataaaaacaaatattcttactattaatcatgtt
atcagagaacttccctgaagttccagtcagtactgtgactagctaattagtcagttacttaagcgtctatccaagtgcaaagggacagga
ggttttgttaagggctgtatcactgtgagctacgccatgaactgggtccgccaggccccaggccagggacttgaatggatgggct
ggatcaacaccaacacccacagtgatacagcccttaacaaaaacccctactgcaacctggcggtaatagacgtccggaagcaca
ctggctgagtaaattcctagtgttctccatcctacctcggagccagagtagcaggagccactagccagcttgggtcttcctatcgcgag
tcgtattaatttcgataagccagcaagcagtgggttctctagttagccagctgcctcctttctctgggcccagcgtcctctgtcctggagct
gggagataatgtccggggggctccttggtctgcgctgggcaaagggtgggcagagtcatgcttgtgctggggacaaaatgaccttggg
acacggtcgacgggctggctgccacggccggcccgggacagtcggagagtca**ggttttgtacacccagacagtggagtactac
cactgt**accggcaaccccacctacgcccagggcttcaccggcagattcgtgttcagcttcgacaccagcgtgtccaccgcctacct
gcaaatctgtagcctgaaggccgaggacaccgccgtgtattactgtgcgagagggacagctatggtccgggctgaatacttccagca
ctggggccagggcaccctggtcaccgtgtcctcag

[SEQ ID NO:5]

ctaaattgtaagcgttaatatttgttaaaattcgcgttaaattttgttaaatcagctcatttttaaccaataggccgaaatcggcaaaatccc
ttataaatcaaaagaatagaccgagatagggttgagtggccgctacagggcgctcccattcgccattcaggctgcgcaactgttggga
agggcgtttcggtgcgggcctcttcgctattacgccagctggcgaaaggggggatgtgctgcaaggcgattaagttgggtaacgccag
ggttttcccagtcacgacgttgtaaaacgacggccagtgagcgcgacgtaatacgactcactatagggcgaattggcggaaggccgt
caaggcctaggcgcgcctgaataacttcgtatagcatacattatagcaatttatcgaaaaagcctgaactcaccgcgacatccgtggag
aaattcctcatcgaaaaattcgactccgtgtccgatctcatgcagctgtccgagggcgaggagagtagagcattctcattcgatgtggg
cgggagaggctacgtgctgagagtgaactcttgtgccgacggcttctacaaggaccgatacgtctaccggcattttgcttccgccgctc
tgcctattccagaagtcctggacattggggagtttagcgagtccctcacttactgtattagccggcgagcccagggagtgacactccag
gatctgcctgaaactgaactgcctgctgtgctccagcctgtcgctgaggcaatggatgctattgctgctgccgatctgagtcagactagc
ggattcggcccatttggaccccagggcattggccagtacacaacatggcgagacttcatctgtgctatcgccgatcctcacgtgtacca
ttggcagactgtgatggacgatactgtgtctgcttctgtggcacaggcactcgacgaactcatgctgtgggctgaggactgtcctgaagt
gagacatctggtccatgccgattttggctccaacaatgtgctcaccgataacgggagaatcactgccgtgatcgactggagcgaggca
atgttggcgattcccagtacgaagtggccaacatcttcttttggcggccttggctggcttgtatggaacagcagacccggtactttgaac
ggcgccaccctgagctggctgggagtcctagactgagagcctacatgctccgaattggcctggatcagctctaccagtcactggtgga
tggcaatttcgacgatgctgcttgggcacaggggcgctgtgatgctattgtccgatccggcgctggaactgtggggagaacacagatc
gctaggagatccgctgctgtctggaccgatggatgtgtggaagtgctggccgatagtggaaaccggaggccttcaacccgaccccg
ggcaaaggagtaatgaccgtttaaacccgctgatcagcctcgactgtgccttctagttgccagccatctgttgtttgccccctcccccgtgc
cttccttgaccctggaaggtgccactcccactgtcctttcctaataaaatgaggaaattgcatcgcattgtctgagtaggtgtcattctattct
gggggtggggtggggcaggacagcaaggggggaggattgggaagacaatagcaggcatgctggggatgcggtgggctctatgg
ggatcccgcgttgacattgattattgactagttattaatagtaatcaattacggggtcattagttcatagcccatatatggagttccgcgttac
ataacttacggtaaatggcccgcctggctgaccgcccaacgaccccgcccattgacgtcaataatgacgtatgttcccatagtaacgc
caatagggactttccattgacgtcaatgggtggagtatttacggtaaactgcccacttggcagtacatcaagtgtatcatatgccaagtac
gccccctattgacgtcaatgacggtaaatggcccgcctggcattatgcccagtacatgaccttatgggactttcctacttggcagtacatc
tacgtattagtcatcgctattaccatggtgatgcggttttggcagtacatcaatgggcgtggatagcggtttgactcacggggatttccaa
gtctccacccattgacgtcaatgggagtttgttttggcaccaaaatcaacgggactttccaaaatgtcgtaacaactccgccccattgac
gcaaatgggcggtaggcgtgtacggtgggaggtctatataagcagagctctctggctaactagagaacccactgcttactgctcgacg
atctgatcaagagacaggataaggagccgccaccatggagtttgggctgagctggcttttcttgtggctatttaaaaggtgtccagtgt
tacccatacgatgttccagattacgcttgtgccctcacagtggtagtactccactgtctgggtgtacaaaaacctccctgcacgcctctc
taacctcacaattctgtggcggccgcgccgccaccatgattgaacaagatggattgcacgcaggttctccggccgcttgggtggagag
gctattcggctatgactgggcacaacagacaatcggctgctctgatgccgccgtgttccggctgtcagcgcagggggcgcccggttcttt
ttgtcaagaccgacctgtccggtgccctgaatgaactgcaggacgaggcagcgcggctatcgtggctggccacgacgggcgttcctt
gcgcagctgtgctcgacgttgtcactgaagcgggaagggactggctgctattgggcgaagtgccggggcaggatctcctgtcatctc
accttgctcctgccgagaaagtatccatcatggctgatgcaatgcggcggctgcatacgcttgatccggctacctgcccattcgaccac
caagcgaaacatcgcatcgagcgagcacgtactcggatggaagccggtcttgtcgatcaggtgagtacaggaggtggagagtacgc
gtaacacttaagcgtctctccaagtgcaaagggacaggaggttttgttaagggctgtatcactgtgagccagttccagtgcggctccg
gctaccacagtgatacagcccttaacaaaaaccccctactgcaacctggcggtaagagacgtccggaggccagcccttctcatgttcag
agaacatggttaactggttaagtcatgtcgtcccacaggatgatctggacgaagagcatcaggggctcgcgccagccgaactgttcgc
caggctcaaggcgcgcatgcccgacggcgaggatctcgtcgtgacccatggcgatgcctgcttgccgaatatcatggtggaaaatgg
ccgcttttctggattcatcgactgtggccggctgggtgtggcggaccgctatcaggacatagcgttggctacccgtgatattgctgaaga
gcttggcggcgaatgggctgaccgcttcctcgtgctttacggtatcgccgctcccgattcgcagcgcatcgccttctatcgccttcttgac
gagttcttctgagtcgactgcaggagtcccactgcacccccctcccagtcttctctgtccaggcaccaggccaggtatctgggtgtgc
agccggcctgggtctggcctgaggccacaagcccggggggtctgtgtggctggggacagggacgccggctgcctctgctctgtgctt
gggccatgtgacccattcgagtgtcctgcacgggcacaggtttttgtacacccagacagtggagtactaccactgtgggctactgcatc
agccagagatgggtgtgcgacggggagaatgattgcgaggacggcagcgacgaggccaattgtgccggctctgtgcctaccgagc
ccaaatcttgtgacaaaactcacacatgcccaccgtgcccagcacctgaactcctggggggaccgtcagtcttcctcttccccccaaaa

cccaaggacaccctcatgatctctagaacccctgaggtcacatgcgtggtggtggacgtgagccacgaagaccctgaggtcaagttc
aactggtacgtggacggcgtggaggtgcataatgccaagacaaagccgcgggaggagcagtacaacagcacgtaccgtgtggtca
gcgtcctcaccgtcctgcaccaggactggctgaatggcaaggagtacaagtgcaaggtgtccaacaaagccctcccagcccccatc
gagaaaaccatctccaaagccaaagggcagccccgagaaccacaggtgtacaccctgcccccatcccgggatgagctgaccaaga
accaggtcagcctgacctgcctggtcaaaggcttctatcccagcgacatcgccgtggagtgggagagcaatgggcagccggagaac
aactacaagaccacgcctcccgtgctggactccgacggctccttcttcctctacagcaagctcaccgtggacaagtctagatggcagc
aggggaacgtcttctcatgctccgtgatgcatgaggctctgcacaaccactacacgcagaagagcctctccctgtctccgggcaaact
ggctctcattgtcctgggcggcgtggctggcctgctgctgtttattgggctgggcatcttcttttgtgtccggtgtcggcataggaggcgc
caaggaggtggcggatctggaggggaggatctggagggggctcaggatcaggggaggatctggaggcggatcaactgagtac
aaacccactgtgaggctcgctactagagatgatgtgcctagagctgtccgaactctggctgctgccttcgccgattaccctgccactcg
ccataccgtcgatcccgatcgccacattgaacgagtcaccgaactccaggagctgtttctcactagagtcgggctggatattggcaaag
tctgggtggccgatgacggagccgctgtcgctgtgtggactacacctgagtctgtggaggctggcgccgtgtttgctgaaattggacct
cggatggctgaactgtctggatctcgactggctgccagcagcagatggagggactgctggcaccccatagaccaaaggaacctgc
ctggtttctggcaactgtgggagtgtcacccgatcatcagggcaaaggactgggatctgccgtggtgctccctggcgtggaggccgct
gaacgagctggcgtccccgcttttctcgaaacttctgcccccccgaaatctcccttttctacgaacgactgggattcactgtcaccgccgat
gtcgaagtgcctgaggggcctagaacatggtgtatgacccggaaacccggagcttaaccgtttaaacccgctgatcagcctcgactgt
gccttctagttgccagccatctgttgtttgcccctcccccgtgccttccttgaccctggaaggtgccactcccactgtcctttcctaataaaa
tgaggaaattgcatcgcattgtctgagtaggtgtcattctattctgggggtggggtgggcaggacagcaaggggaggattggga
agacaatagcaggcatgctggggatgcggtgggctctatggctcgagttaattaactggcctcatgggccttccgctcactgcccgctt
tccagtcgggaaacctgtcgtgccagctgcattaacatggtcatagctgtttccttgcgtattgggcgctctccgcttcctcgctcactgac
tcgctgcgctcggtcgttcgggtaaagcctggggtgccataatgagcaaaaggccagcaaaaggccaggaaccgtaaaaaggccgc
gttgctggcgtttttccataggctccgcccccctgacgagcatcacaaaaatcgacgctcaagtcagaggtggcgaaacccgacagg
actataaagataccaggcgtttccccctggaagctccctcgtgcgctctcctgttccgaccctgccgcttaccggataccgtccgccttt
ctcccttcgggaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgacttatcgccactg
gcagcagccactggtaacaggattagcagagcgaggtatgtaggcggtgctacagagttcttgaagtggtggcctaactacggctac
actagaagaacagtatttggtatctgcgctctgctgaagccagttaccttcggaaaaagagttggtagctcttgatccggcaaacaaacc
accgctggtagcggtggtttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatcctttaaattaa
aaatgaagttttaaatcaatctaaagtatatatgagtaaacttggtctgacagttaccaatgcttaatcagtgaggcacctatctcagcgatc
tgtctatttcgttcatccatagttgcctgactccccgtcgtgtagataactacgatacgggagggcttaccatctggccccagtgctgcaat
gataccgcgagaaccacgctcaccggctccagatttatcagcaataaaccagccagccggaagggccgagcgcagaagtggtcct
gcaactttatccgcctccatccagtctattaattgttgccgggaagctagagtaagtagttcgccagttaatagtttgcgcaacgttgttgc
cattgctacaggcatcgtggtgtcacgctcgtcgtttggtatggcttcattcagctccggttcccaacgatcaaggcgagttacatgatcc
cccatgttgtgcaaaaaagcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaagtcattctgagaatagtgtat
gcggcgaccgagttgctcttgcccggcgtcaatacgggataataccgcgccacatagcagaactttaaaagtgctcatcattggaaaa
cgttcttcggggcgaaaactctcaaggatcttaccgctgttgagatccagttcgatgtaacccactcgtgcacccaactgatcttcagcat
cttttactttcaccagcgtttctgggtgagcaaaaacaggaaggcaaaatgccgcaaaaaagggaataagggcgacacggaaatgttg
aatactcatactcttcctttttcaatattattgaagcatttatcagggttattgtctcatgagcggatacatatttgaatgtatttagaaaaataaa
caaatagggggttccgcgcacatttccccgaaaagtgccac

[SEQ ID NO:1]

ctaaattgtaagcgttaatattttgttaaaattcgcgttaaattttgttaaatcagctcattttttaaccaataggccgaaatcggcaaaatccc
ttataaatcaaaagaatagaccgagatagggttgagtggccgctacagggcgctcccattcgccattcaggctgcgcaactgttggga
agggcgtttcggtgcgggcctcttcgctattacgccagctggcgaaaggggatgtgctgcaaggcgattaagttgggtaacgccag
ggttttcccagtcacgacgttgtaaaacgacggccagtgagcgcgacgtaatacgactcactatagggcgaattggcggaaggccgt
caaggcctaggcgcgcctgaataacttcgtatagcatacattatagcaatttatcgaaaaagcctgaactcaccgcgacatccgtggag
aaattcctcatcgaaaaattcgactccgtgtccgatctcatgcagctgtccgagggcgaggagagtagagcattctcattcgatgtggg
cgggagaggctacgtgctgagagtgaactcttgtgccgacggcttctacaaggaccgatacgtctaccggcattttgcttccgccgctc
tgcctattccagaagtcctggacattggggagtttagcgagtccctcacttactgtattagccggcgagcccagggagtgacactccag
gatctgcctgaaactgaactgcctgctgtgctccagcctgtcgctgaggcaatggatgctattgctgctgccgatctgagtcagactagc
ggattcggcccatttggaccccagggcattggccagtacacaacatggcgagacttcatctgtgctatcgccgatcctcacgtgtacca
ttggcagactgtgatggacgatactgtgtctgcttctgtggcacaggcactcgacgaactcatgctgtgggctgaggactgtcctgaagt
gagacatctggtccatgccgattttggctccaacaatgtgctcaccgataacgggagaatcactgccgtgatcgactggagcgaggca
atgtttggcgattcccagtacgaagtggccaacatcttcttttggcggccttggctggcttgtatggaacagcagacccggtactttgaac
ggcgccaccctgagctggctgggagtcctagactgagagcctacatgctccgaattggcctggatcagctctaccagtcactggtgga
tggcaatttcgacgatgctgcttgggcacaggggcgctgtgatgctattgtccgatccggcgctggaactgtggggagaacacagatc
gctaggagatccgctgctgtctggaccgatggatgtgtggaagtgctggccgatagtggaaaccggaggccttcaacccgaccccg
ggcaaaggagtaatgaccgtttaaacccgctgatcagcctcgactgtgccttctagttgccagccatctgttgtttgcccctcccccgtgc
cttccttgaccctggaaggtgccactcccactgtcctttcctaataaaatgaggaaattgcatcgcattgtctgagtaggtgtcattctattct
gggggtgggtggggcaggacagcaaggggaggattgggaagacaatagcaggcatgctggggatgcggtgggctctatgg
ggatcccgcgttgacattgattattgactagttattaatagtaatcaattacggggtcattagttcatagcccatatatggagttccgcgttac
ataacttacggtaaatggcccgcctggctgaccgcccaacgaccccgcccattgacgtcaataatgacgtatgttcccatagtaacgc
caataggggactttccattgacgtcaatgggtggagtatttacggtaaactgcccacttggcagtacatcaagtgtatcatatgccaagtac
gccccctattgacgtcaatgacggtaaatggcccgcctggcattatgcccagtacatgaccttatgggactttcctacttggcagtacatc
tacgtattagtcatcgctattaccatggtgatgcggttttggcagtacatcaatgggcgtggatagcggtttgactcacggggatttccaa
gtctccacccccattgacgtcaatgggagtttgttttggcaccaaaatcaacgggactttccaaaatgtcgtaacaactccgccccattgac
gcaaatgggcggtaggcgtgtacggtgggaggtctatataagcagagctctctggctaactagagaacccactgcttactgctcgacg
atctgatcaagagacaggataaggagccgccaccatggagtttgggctgagctggcttttcttgtggctatttaaaaggtgtccagtgt
tacccatacgatgttccagattacgcttgcctgccccacagtggtagtactccactgtctgggtgtacaaaaacctccctgcacgcctctc
taacctcacaattctgtggcggccgcgccgccaccatgattgaacaagatggattgcacgcaggttctccggccgcttgggtggagag
gctattcggctatgactgggcacaacagacaatcggctgctctgatgccgccgtgttccggctgtcagcgcaggggcgcccggttcttt
ttgtcaagaccgacctgtccggtgccctgaatgaactgcaggacgaggcagcgcggctatcgtggctggccacgacgggcgttcctt
gcgcagctgtgctcgacgttgtcactgaagcgggaagggactggctgctattgggcgaagtgccggggcaggatctcctgtcatctc
accttgctcctgccgagaaagtatccatcatggctgatgcaatgcggcggctgcatacgcttgatccggctacctgcccattcgaccac
caagcgaaacatcgcatcgagcgagcacgtactcggatggaagccggtcttgtcgatcaggtgagtacaggaggtggagagtacgc
gtaacacttaagcgtctctccaagtgcaaagggacaggaggttttgttaagggctgtatcactgtggaccagttcagatgcggcaacg
gccagtgcatcccctggattgggtgtgcgacggcgtgaacgactgccccgattccgatgaggaaggctgcccccctagaacctgtg
cccctagccagcacagtgatacagcccttaacaaaaacccctactgcaacctggcggtaagagacgtccggaggccagcccttctca
tgttcagagaacatggttaactggttaagtcatgtcgtcccacaggatgatctggacgaagagcatcaggggctcgcgccagccgaac
tgttcgccaggctcaaggcgcgcatgcccgacggcgaggatctcgtcgtgacccatggcgatgcctgcttgccgaatatcatggtgg
aaaatggccgcttttctggattcatcgactgtggccggctgggtgtggcggaccgctatcaggacatagcgttggctacccgtgatattg
ctgaagagcttggcggcgaatgggctgaccgcttcctcgtgctttacggtatcgccgctcccgattcgcagcgcatcgccttctatcgc
cttcttgacgagttcttctgagtcgactgcaggagtcccactgcaccccctcccagtcttctctgtccaggcaccaggccaggtatctg
gggtgtgcagccggcctgggtctggcctgaggccacaagcccggggtctgtgtggctggggacagggacgccggctgcctctgc
tctgtgcttgggccatgtgacccattcgagtgtcctgcacgggcacaggttttgtacacccagacagtggagtactaccactgtgttcca
gtgcggctccggctactgcatcagccagagatgggtgtgcgacggggagaatgattgcgaggacggcagcgacgaggccaattgt
gccggctctgtgcctaccgagcccaaatcttgtgacaaaactcacacatgcccaccgtgcccagcacctgaactcctgggggaccg

tcagtcttcctcttcccccaaaacccaaggacaccctcatgatctctagaaccccctgaggtcacatgcgtggtggtggacgtgagcca
cgaagaccctgaggtcaagttcaactggtacgtggacggcgtggaggtgcataatgccaagacaaagccgcgggaggagcagtac
aacagcacgtaccgtgtggtcagcgtcctcaccgtcctgcaccaggactggctgaatggcaaggagtacaagtgcaaggtgtccaac
aaagccctcccagcccccatcgagaaaaccatctccaaagccaaagggcagccccgagaaccacaggtgtacaccctgccccat
cccgggatgagctgaccaagaaccaggtcagcctgacctgcctggtcaaaggcttctatcccagcgacatcgccgtggagtgggag
agcaatgggcagccggagaacaactacaagaccacgcctcccgtgctggactccgacggctccttcttcctctacagcaagctcacc
gtggacaagtctagatggcagcaggggaacgtcttctcatgctccgtgatgcatgaggctctgcacaaccactacacgcagaagagc
ctctccctgtctccgggcaaactggctctcattgtcctgggcggcgtggctggcctgctgctgtttattgggctgggcatcttcttttgtgtc
cggtgtcggcataggaggcgccaaggaggtggcggatctggagggggaggatctggaggggggctcaggatcaggggaggatc
tggaggcggatcaactgagtacaaacccactgtgaggctcgctactagagatgatgtgcctagagctgtccgaactctggctgctgcc
ttcgccgattaccctgccactcgccataccgtcgatcccgatcgccacattgaacgagtcaccgaactccaggagctgtttctcactaga
gtcgggctggatattggcaaagtctgggtggccgatgacggagccgctgtcgctgtgtggactacacctgagtctgtggaggctggc
gccgtgtttgctgaaattggacctcggatggctgaactgtctggatctcgactggctgcccagcagcagatggagggactgctggcac
cccatagaccaaaggaacctgcctggtttctggcaactgtgggagtgtcacccgatcatcagggcaaaggactgggatctgccgtggt
gctccctggcgtggaggccgctgaacgagctggcgtccccgcttttctcgaaacttctgccccccgaaatctcctttctacgaacgac
tgggattcactgtcaccgccgatgtcgaagtgcctgaggggcctagaacatggtgtatgacccggaaacccggagcttaaccgtttaa
acccgctgatcagcctcgactgtgccttctagttgccagccatctgttgtttgccctcccccgtgccttccttgaccctggaaggtgcca
ctcccactgtcctttcctaataaaatgaggaaattgcatcgcattgtctgagtaggtgtcattctattctgggggtggggtggggcagga
cagcaaggggaggattgggaagacaatagcaggcatgctggggatgcggtgggctctatggctcgagttaattaactggcctcatg
ggccttccgctcactgcccgctttccagtcgggaaacctgtcgtgccagctgcattaacatggtcatagctgtttccttgcgtattgggcg
ctctccgcttcctcgctcactgactcgctgcgctcggtcgttcgggtaaagcctgggggtgcctaatgagcaaaaggccagcaaaaggc
caggaaccgtaaaaaggccgcgttgctggcgtttttccataggctccgcccccctgacgagcatcacaaaaatcgacgctcaagtcag
aggtggcgaaacccgacaggactataaagataccaggcgtttccccctggaagctccctcgtgcgctctcctgttccgaccctgccgc
ttaccggatacctgtccgcctttctcccttcgggaagcgtggcgctttctcatagctcacgctgtaggtatctcagttcggtgtaggtcgtt
cgctccaagctgggctgtgtgcacgaaccccccgttcagcccgaccgctgcgccttatccggtaactatcgtcttgagtccaacccggt
aagacacgacttatcgccactggcagcagccactggtaacaggattagcagagcgaggtatgtaggcggtgctacagagttcttgaa
gtggtggcctaactacggctacactagaagaacagtatttggtatctgcgctctgctgaagccagttaccttcggaaaaagagttggtag
ctccttgatccggcaaacaaaccaccgctggtagcggtggtttttttgttgcaagcagcagattacgcgcagaaaaaaggatctcaag
aagatcctttgatcttttctacggggtctgacgctcagtggaacgaaaactcacgttaagggattttggtcatgagattatcaaaaaggatc
ttcacctagatccttttaaattaaaaatgaagttttaaatcaatctaaagtatatatgagtaaacttggtctgacagttaccaatgcttaatcag
tgaggcacctatctcagcgatctgtctatttcgttcatccatagttgcctgactccccgtcgtgtagataactacgatacggaggcttac
catctggccccagtgctgcaatgataccgcgagaaccacgctcaccggctccagatttatcagcaataaaccagccagccggaagg
gccgagcgcagaagtggtcctgcaacttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagctccggttcccaacg
atcaaggcgagttacatgatccccatgttgtgcaaaaaagcggttagctccttcggtcctccgatcgttgtcagaagtaagttggccgc
agtgttatcactcatggttatggcagcactgcataattctcttactgtcatgccatccgtaagatgcttttctgtgactggtgagtactcaacc
aagtcattctgagaatagtgtatgcggcgaccgagttgctcttgcccggcgtcaatacgggataataccgcgccacatagcagaacttt
aaaagtgctcatcattggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgcaaaaaagggaat
aagggcgacacggaaatgttgaatactcatactcttcctttttcaatattattgaagcatttatcagggttattgtctcatgagcggatacata
tttgaatgtatttagaaaaataaacaaataggggttccgcgcacatttccccgaaaagtgccac

[SEQ ID NO:40]

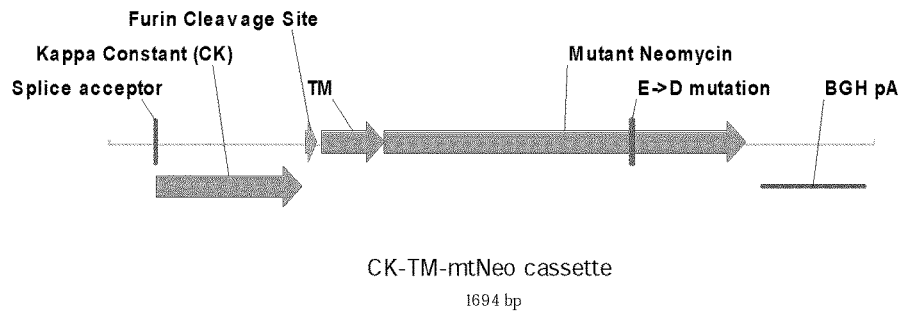

CK-TM-mtNeo cassette
1694 bp

B.

aattcttctgtctgtccctaacatgccctgtgattatccgcaaacaacacacccaagggcagaactttgttacttaaacaccatcctgtttgc
ttctttcctcaggaactgtggctgcaccatctgtcttcatcttcccgccatctgatgagcagttgaaaagcggaacagccagcgttgtgtg
cctgctgaataacttctatcccagagaggccaaagtacagtggaaggtggataacgccctccaatcgggtaactcccaggagagtgtc
acagagcaggacagcaaggacagcacctacagcctcagcagcaccctgacgctgagcaaagcagactacgagaaacacaaagtc
tacgcctgcgaagtcacccatcagggcctgagcagccccgtcacaaagagcttcaacaggggagagtgtggcggcgg**agctccc
ggcaccgccgagccct**gggcggcggcagcgacgtcccgtcaaatattgcaaaaattatcatcggccccctcatctttgtctttctcttct
ccgttgtgattggaagtatttatctattcctgagaaagaggcagccagatgggccgctgggaccgctttacgcttctggaagcgctattg
aacaagatggattgcacgcaggttctccggccgcttgggtggagaggctattcggctatgactgggcacaacagacaatcggctgct
ctgatgccgccgtgttccggctgtcagcgcaggggcgcccggttctttttgtcaagaccgacctgtccggtgccctgaatgaactgcag
gacgaggcagcgcggctatcgtggctggccacgacgggcgttccttgcgcagctgtgctcgacgttgtcactgaagcgggaaggga
ctggctgctattgggcgaagtgccggggcaggatctcctgtcatctccacttgctcctgccgagaaagtatccatcatggctgatgcaat
gcggcggctgcatacgcttgatccggctacctgcccattcgaccaccaagcgaaacatcgcatcgagcgagcacgtactcggatgg
aagccggtcttgtcgatcaggatgatctggacgaagagcatcaggggctcgcgccagccgaactgttcgccaggctcaaggcgcgc
atgcccgacggcgatgatctcgtcgtgacccatggcgatgcctgcttgccgaatatcatggtggaaaatggccgcttttctggattcatc
gactgtggccggctgggtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgacgagttcttctgatctaga
gggcccgtttaaacccgctgatcagcctcgactgtgccttctagttgccagccatctgttgtttgcccctcccccgtgccttccttgaccct
ggaaggtgccactcccactgtcctttcctaataaaatgaggaaattgcatcgcattgtctgagtaggtgtcattctattctggggggtggg
gtggggcaggacagcaaggggaggattgggaagacaatagcaggcatgctggggatgcggtgggctctatggcttctgaggcg
gctgcagttatg

[SEQ ID NO:41]

CTAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGA
ATAGACCGAGATAGGGTTGAGTGGCCGCTACAGGGCGCTCCCATTCGCCATTCA
GGCTGCGCAACTGTTGGGAAGGGCGTTTCGGTGCGGGCCTCTTCGCTATTACGCC
AGCTGGCGAAAGGGGGATGTGCTGCAAGGCGATTAAGTTGGGTAACGCCAGGGT
TTTCCCAGTCACGACGTTGTAAAACGACGGCCAGTGAGCGCGACGTAATACGAC
TCACTATAGGGCGAATTGGCGGAAGGCCGTCAAGGCCTACGCGCCGACCGAGTC
CACTAGTTAACTAGCTGAGGGCCGAGGCCGCCCTGCTGCAGTGCACCGCCGATA
CCCTGGCCGACGCCGTGCTGATCACCACCGCCCACGCTTGGCAGCACCAGGGCA
AGACACTGTTCATCTCCAGAAAGACCTACCGGATCGACGGCAGCGGCCAGATGG
CCATCACAGTGGACGTGGAGGTGGCCTCCGACACCCCTCACCCCGCCAGAATCG
GCCTGAACTGTCAGCTGGCCCAGGTGGCCGAGAGAGTGAACTGGCTGGGCCTGG
GCCCCAGGAGAACTACCCCGACCGGCTGACCGCCGCCTGCTTCGACAGATGGG
ACCTGCCTCTGAGCGACATGTACACCCCCTACGTGTTCCCCAGCGAGAATGGCCT
GAGATGCGGCACCCGGGAGCTGAACTACGGCCCCACCAGTGGAGGGCGACTT
CCAGTTCAACATCAGCCGGTACTCGGATCTGAAGTTCCTATTCCGAAGTTCCTAT
TCTCTAGAAAGTATAGGAACTTCGGGCCACATGGACAGAGGCCGGCTCGGCCCA
CCCTCTGCCCTGAGAGTGACCGCTGTACCAACCTCTGTCCCTACAGGGCAGCCCC
GAGAACCACAGGTGTACACCCTGCCTCCAAGCAGGGACGAACTGACAAAGAATC
AGGTGTCCCTCACCTGCCTCGTGAAGGGCTTTTACCCCTCCGATATCGCAGTGGA
ATGGGAGTCCAACGGCCAGCCCGAGAATAATTACAAAACAACCCCCCCTGTGCT
GGACAGCGACGGCAGCTTCTTTCTGTACTCCAAGCTGACAGTGGATAAGTCCCGC
TGGCAGCAGGGCAATGTGTTCAGCTGCTCTGTGATGCACGAAGCCCTCCACAATC
ATTATACCCAGAAGTCCCTGAGCCTGAGCCCCGGCAAGTGACAATTCCAACGCC
GCCCCTCTCCCTCCCCCCCCCCTAACGTTACTGGCCGAAGCCGCTTGGAATAAGG
CCGGTGTGCGTTTGTCTATATGTTATTTTCCACCATATTGCCGTCTTTTGGCAATG
TGAGGGCCCGGAAACCTGGCCCTGTCTTCTTGACGAGCATTCCTAGGGGTCTTTC
CCCTCTCGCCAAAGGAATGCAAGGTCTGTTGAATGTCGTGAAGGAAGCAGTTCCT
CTGGAAGCTTCTTGAAGACAAACAACGTCTGTAGCGACCCTTTGCAGGCAGCGG
AACCCCCCACCTGGCGACAGGTGCCTCTGCGGCCAAAAGCCACGTGTATAAGAT
ACACCTGCAAAGGCGGCACAACCCAGTGCCACGTTGTGAGTTGGATAGTTGTG
GAAAGAGTCAAATGGCTCTCCTCAAGCGTATTCAACAAGGGGCTGAAGGATGCC
CAGAAGGTACCCCATTGTATGGGATCTGATCTGGGGCCTCGGTACACATGCTTTA
CATGTGTTTAGTCGAGGTTAAAAAAACGTCTAGGCCCCCGAACCACGGGGACG
TGGTTTTCCTTTGAAAAACACGATGATAATATGGCCACAAGATCTGCCACCACCG
CCGCCAACATGAGCGAAAAATACATCGTCACCTGGGACATGTTGCAGATCCATG
CACGTAAACTCGCAAGCCGACTGATGCCTTCTGAACAATGGAAAGGCATTATTGC
CGTAAGCCGTGGCGGTCTGGTACCGGGTGCGTTACTGGCGCGTGAACTGGGTATT
CGTCATGTCGATACCGTTTGTATTTCCAGCTACGATCACGACAACCAGCGCGAGC
TTAAAGTGCTGAAACGCGCAGAAGGCGATGGCGAAGGCTTCATCGTTATTGATG
ACCTGGTGGATACCGGTGGTACTGCGGTTGCGATTCGTGAAATGTATCCAAAAGC
GCACTTTGTCACCATCTTCGCAAAACCGGCTGGTCGTCCGCTGGTTGATGACTAT
GTTGTTGATATCCCGCAAGATACCTGGATTGAACAGCCGTGGGATATGGGCGTCG
TATTCGTCCCGCCAATCTCCGGTCGCTAATCTTTTCAACGCCTGGCACTGCCGGG
CGTTGTTCTTTTAACTTCAGGCGGGTTACAATAGTTTCCAGTAAGTATTCTGGAG
GCTGCATCCATGACACAGGCAAACCTGAGCGAAACCCTGTTCAAACCCCGCTTTA
AACATCCTGAAACCTCGACGCTAGTCCGCCGCTTAATCACGGCGCACAACCGCC
TGTGCAGTCGGCCCTTGATGGTAAAACCATCCCTCACTGGTATCGCATGATTAAC

FIG. 20A

B.
CGTCTGATGTGGATCTGGCGCGGCATTGACCCACGCGAAATCCTCGACGTCCAGG
CACGTATTGTGATGAGCGATGCCGAACGTACCGACGATGATTTATACGATACGGT
GATTGGCTACCGTGGCGGCAACTGGATTTATGAGTGGGCCCCGGATCTTTGTGAA
GGAACCTTACTTCTGTGGTGTGACATAATTGGACAAACTACCTACAGAGATTTAA
AGCTCTAAGGTAAATATAAAATTTTTAAGTGTATAATGTGTTAAACTACTGATTC
TAATTGTTTGTGTATTTTAGATTCCAACCTATGGAACTGATGAATGGGAGCAGTG
GTGGAATGCCTTTAATGAGGAAAACCTGTTTGCTCAGAAGAAATGCCATCTAGT
GATGATGAGGCTACTGCTGACTCTCAACATTCTACTCCTCCAAAAAAGAAGAGA
AAGGTAGAAGACCCCAAGGACTTTCCTTCAGAATTGCTAAGTTTTTTGAGTCATG
CTGTGTTTAGTAATAGAACTCTTGCTTGCTTTGCTATTTACACCACAAAGGAAAA
AGCTGCACTGCTATACAAGAAAATTATGGAAAAATATTCTGTAACCTTTATAAGT
AGGCATAACAGTTATAATCATAACATACTGTTTTTTCTTACTCCACACAGGCATA
GAGTGTCTGCTATTAATAACTATGCTCAAAAATTGTGTACCTTTAGCTTTTTAATT
TGTAAAGGGGTTAATAAGGAATATTTGATGTATAGTGCCTTGACTAGAGATCATA
ATCAGCCATACCACATTTGTAGAGGTTTTACTTGCTTTAAAAAACCTCCCACACC
TCCCCCTGAACCTGAAACATAAAATGAATGCAATTGTTGTTGTTAACTTGTTTATT
GCAGCTTATAATGGTTACAAATAAAGCAATAGCATCACAAATTTCACAAATAAA
GCATTTTTTCACTGCATTCTAGTTGTGGTTTGTCCAAACTCATCAATGTATCTTA
TCATGTCTGGGCTAGCCTCGAAGAGATTAGAATCCGAGGGCGCGCCTGAATAAC
TTCGTATAGCATACATTATAGCAATTTATCGAAAAAGCCTGAACTCACCGCGACA
TCCGTGGAGAAATTCCTCATCGAAAAATTCGACTCCGTGTCCGATCTCATGCAGC
TGTCCGAGGGCGAGGAGAGTAGAGCATTCTCATTCGATGTGGGCGGGAGAGGCT
ACGTGCTGAGAGTGAACTCTTGTGCCGACGGCTTCTACAAGGACCGATACGTCTA
CCGGCATTTTGCTTCCGCCGCTCTGCCTATTCCAGAAGTCCTGGACATTGGGGAG
TTTAGCGAGTCCCTCACTTACTGTATTAGCCGGCGAGCCCAGGGAGTGACACTCC
AGGATCTGCCTGAAACTGAACTGCCTGCTGTGCTCCAGCCTGTCGCTGAGGCAAT
GGATGCTATTGCTGCTGCCGATCTGAGTCAGACTAGCGGATTCGGCCCATTTGGA
CCCCAGGGCATTGGCCAGTACACAACATGGCGAGACTTCATCTGTGCTATCGCCG
ATCCTCACGTGTACCATTGGCAGACTGTGATGGACGATACTGTGTCTGCTTCTGT
GGCACAGGCACTCGACGAACTCATGCTGTGGGCTGAGGACTGTCCTGAAGTGAG
ACATCTGGTCCATGCCGATTTTGGCTCCAACAATGTGCTCACCGATAACGGGAGA
ATCACTGCCGTGATCGACTGGAGCGAGGCAATGTTTGGCGATTCCCAGTACGAA
GTGGCCAACATCTTCTTTTGGCGGCCTTGGCTGGCTTGTATGGAACAGCAGACCC
GGTACTTTGAACGGCGCCACCCTGAGCTGGCTGGGAGTCCTAGACTGAGAGCCT
ACATGCTCCGAATTGGCCTGGATCAGCTCTACCAGTCACTGGTGGATGGCAATTT
CGACGATGCTGCTTGGGCACAGGGGCGCTGTGATGCTATTGTCCGATCCGGCGCT
GGAACTGTGGGGAGAACACAGATCGCTAGGAGATCCGCTGCTGTCTGGACCGAT
GGATGTGTGGAAGTGCTGGCCGATAGTGGAAACCGGAGGCCTTCAACCCGACCC
CGGGCAAAGGAGTAATGACCGTTTAAACCCGCTGATCAGCCTCGACTGTGCCTTC
TAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCT
GAGTAGGTGTCATTCTATTCTGGGGGGTGGGGTGGGCAGGACAGCAAGGGGGA
GGATTGGGAAGACAATAGCAGGCATGCTGGGGATGCGGTGGGCTCTATGGGAT
CCCGCGTTGACATTGATTATTGACTAGTTATTAATAGTAATCAATTACGGGGTCA
TTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGT
TCCCATAGTAACGCCAATAGGGACTTTCCATTGACGTCAATGGGTGGAGTATTTA
CGGTAAACTGCCCACTTGGCAGTACATCAAGTGTATCATATGCCAAGTACGCCCC

FIG. 20B

C.
CTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACG
GGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGG
GCGGTAGGCGTGTACGGTGGGAGGTCTATATAAGCAGAGCTCTCTGGCTAACTA
GAGAACCCACTGCTTACTGCTCGACGATCTGATCAAGAGACAGGATAAGGAGCC
GCCACCATGGACATGAGGGTCCCCGCTCAGCTCCTGGGGCTCCTGCTACTCTGGC
TCCGAGGTGCCAGATGTGACATCCAGATGACCCAGAGCCCCAGCAGCCTGAGCG
CCAGCGTGGGCGACAGAGTGACCATCACCTGTCGGGCCAGCCAGTCGATCAGCA
GCTACCTGAACTGGTATCAGCAGAAGCCCGGCAAGGCCCCAAGCTGCTGATCT
ACGCCGCCAGCTCCCTGCACAGTGGTAGTACTCCACTGTCTGGGTGTACAAAAAC
CTCCCTGCACGCCTCTCTAACCTCACAATTCTGTGACGCGTTCCTGAATGCGGCC
GCCACTTCCGGAGTGCTGGATATCAGTCGACCGGTCTGAGTGTCACACCTACTGC
GAGCTCAACCTGGCGGTAACTGTGACCTGGCGGTATGTGTCAGACCCAGATCTCG
TTACTCCAATAGGTCCAAGCTTGGTTTGAGAGGAGAATAGGATTCATGGGGGAA
ATGGGGAAGAAATAGCTAGATTTTTCTCTGAACAAGCAGCCTATCTCATATGATT
GGCTTCAAGAGAGGTTTTTGTATTGGTCTGTACCACTGTGTCCCTGCAGAGCGGC
GTGCCAAGCAGATTCAGCGGCAGCGGCTCCGGCACCGACTTCACCCTGACCATC
AGCAGCCTGCAGCCCGAGGACTTCGCCACCTACTACTGCCAGCAGAGTTACAGT
ACCCCTCTCACTTTCGGCGGAGGGACCAAGGTGGAGATCAAACGTAAGTGCACT
TTCCTAATGCTTTTTCTTATAAGGTTTTAAATTTGGAGCGTTTTGTGTTTGAGAT
ATTAGCTCAGGTCAATTCCAAAGAGTACCAGATGAATTCTTCTGTCTGTCCCTAA
CATGCCCTGTGATTATCCGCAAACAACACACCCAAGGGCAGAACTTTGTTACTTA
AACACCATCCTGTTTGCTTCTTTCCTCAGGAACTGTGGCTGCACCATCTGTCTTCA
TCTTCCCGCCATCTGATGAGCAGTTGAAAAGCGGAACAGCCAGCGTTGTGTGCCT
GCTGAATAACTTCTATCCCAGAGAGGCCAAAGTACAGTGGAAGGTGGATAACGC
CCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACA
CAAAGTCTACGCCTGCGAAGTCACCCATCAGGGCCTGAGCAGCCCCGTCACAAA
GAGCTTCAACAGGGGAGAGTGTGGCGGCGGCAGCTCCCGGCACCGCCGAGCCCT
GGGCGGCGGCAGCGACGTCCCGTCAAATATTGCAAAAATTATCATCGGCCCCCT
CATCTTTGTCTTTCTCTTCTCCGTTGTGATTGGAAGTATTTATCTATTCCTGAGAA
AGAGGCAGCCAGATGGGCCGCTGGGACCGCTTTACGCTTCTGGAAGCGCTATTG
AACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTG
AATGAACTGCAGGACGAGGCAGCGCGGCTATCGTGGCTGGCCACGACGGGCGTT
CCTTGCGCAGCTGTGCTCGACGTTGTCACTGAAGCGGGAAGGGACTGGCTGCTAT
TGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACC
TGCCCATTCGACCACCAAGCGAAACATCGCATCGAGCGAGCACGTACTCGGATG
GAAGCCGGTCTTGTCGATCAGGATGATCTGGACGAGGAGCATCAGGGGCTCGCG
CCAGCCGAACTGTTCGCCAGGCTCAAGGCGCGCATGCCCGACGGCGATGATCTC
GTCGTGACCCATGGCGATGCCTGCTTGCCGAATATCATGGTGGAAAATGGCCGCT
TTTCTGGATTCATCGACTGTGGCCGGCTGGGTGTGGCGGACCGCTATCAGGACAT
AGCGTTGGCTACCCGTGATATTGCTGAGGAGCTTGGCGGCGAATGGGCTGACCG
CTTCCTCGTGCTTTACGGTATCGCCGCTCCCGATTCGCAGCGCATCGCCTTCTATC

FIG. 20C

D.
GCCTTCTTGACGAGTTCTTCTGATCTAGAGGGCCCGTTTAAACCCGCTGATCAGC
CTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAG
GACAGCAAGGGGGAGGATTGGGAAGACAATAGCAGGCATGCTGGGGATGCGGT
GGGCTCTATGGCTTCTGAGGCGGCTGCAGTTATGTCGACCGCGTTGACATTGATT
ATTGACTAGTTATTAATAGTAATCAATTACGGGGTCATTAGTTCATAGCCCATAT
ATGGAGTTCCGCGTTACATAACTTACGGTAAATGGCCCGCCTGGCTGACCGCCCA
ACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTG
GCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCA
CCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGG
TGGGAGGTCTATATAAGCAGAGCTCTCTGGCTAACTAGAGAACCCACTGCTTACT
GGCTTATCGAAATTAATACGACTCACTATAGGGAGACACAAGCTGGCGGCCGCT
AATAAAGGCGATCTGATCAAGAGACAGGATAAGGAGCCGCCACCATGGAGTTTG
GGCTGAGCTGGCTTTTTCTTGTGGCTATTTTAAAAGGTGTCCAGTGTCAGGTGCA
GCTGGTGCAGTCTGGCGCCGAAGTGAAGAAACCTGGCGCCTCCGTGAAGGTGTC
CTGCAAGGCCAGCGGCTACACCTTCACCAGCTACGGCATCAGCTGGGTCCGCCA
GGCTCCTGGACAGGGACTGGAATGGATGGGCTGGATCAGCGCCTACAACGGCAA
CACCAACTACGCCCAGAAACTGCAGGGCAGAGTGACCATGACCACCGACACCAG
CACCAGCACCGCCTACATGGAACTTCGAAGCCTGAGAAGCGACGACACCGCCGT
GTATTACTGTGCGAGAGAGCTAGCCTATGATGCTTTTGATATCTGGGGCCAAGGG
ACAATGGTCACCGTGTCCTCAGCCTCCACCAAGGGCCCATCGGTCTTCCCCCTGG
CACCCTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTGACCA
GCGGCGTGCATACCTTCCCGGCTGTCCTACAGTCCTCAGGACTCTACTCCCTCAG
CAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCT
TGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCTAGAA
CCCCTGAGGTCACATGCGTGGTGGTGGACGTGAGCCACGAAGACCCTGAGGTCA
AGTTCAACTGGTACGTGGACGGCGTGGAGGTGCATAATGCCAAGACAAAGCCGC
GGGAGGAGCAGTACAACAGCACGTACCGTGTGGTCAGCGTCCTCACCGTCCTGC
ACCAGGACTGGCTGAATGGCAAGGAGTACAAGTGCAAGGTGTCCAACAAAGCCC
TCCCAGCCCCCATCGAGAAAACCATCTCCAAAGCCAAAGGTGGGACCCGTGGGG
TGCGAATAGAAGTTCCTATTCCGAAGTTCCTATTCTCTAGAAAGTATAGGAACTT
CGGGCCACATGGAATTAATTCAGAGGCCGGCTCGGCCCACCCTCTGCCCTGAGA
GTGACCGCTGTACCAACCTCTGTCCCTACAGGGCAGCCCCGAGAACCACAGGTG
TACACCCTGCCCCCATCCCGGGATGAGCTGACCAAGAACCAGGTCAGCCTGACC
TGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGA
AGAACCTCTCCCTGTCTCCGGGCAAAGCTGTGGGCCAGGACACGCAGGAGGTCA

TCGTGGTGCCACACTCCTTGCCCTTTAAGGTGGTGGTGATCTCAGCCATCCTGGC
CCTGGTGGTGCTCACCATCATCTCCCTTATCATCCTCATCATGCTTTGGCAGAAGA
AGCCACGTTAGGTTTTCCGGGACGCCGGCTGGATGATCCTCCAGCGCGGGGATCT
CATGCTGGAGTTCTTCGCCCACCCCAACTTGTTTATTGCAGCTTATAATGGTTACA
AATAAAGCAATAGCATCACAAATTTCACAAATAAAGCATTTTTTTCACTGCATTC
TAGTTGTGGTTTGTCCAAACTCATCAATGTATCTTATCATGTCTGACCTCGAGTTA
ATTAACTGGCCTCATGGGCCTTCCGCTCACTGCCCGCTTTCCAGTCGGGAAACCT
GTCGTGCCAGCTGCATTAACATGGTCATAGCTGTTTCCTTGCGTATTGGGCGCTCT
CCGCTTCCTCGCTCACTGACTCGCTGCGCTCGGTCGTTCGGGTAAAGCCTGGGGT
GCCTAATGAGCAAAAGGCCAGCAAAAGGCCAGGAACCGTAAAAAGGCCGCGTT
GCTGGCGTTTTCCATAGGCTCCGCCCCCTGACGAGCATCACAAAAATCGACGC
TCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAG
GGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCA
TCTGGCCCCAGTGCTGCAATGATACCGCGAGAACCACGCTCACCGGCTCCAGATT
TATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAG
TTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGTCCTCC
GATCGTTGTCAGAAGTAAGTTGGCCGCAGTGTTATCACTCATGGTTATGGCAGCA
CTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGC
CCGGCGTCAATACGGGATAATACCGCGCCACATAGCAGAACTTTAAAAGTGCTC
ATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACT
TTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATT
ATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCAC

[SEQ ID NO:74]

FIG. 20E

A.
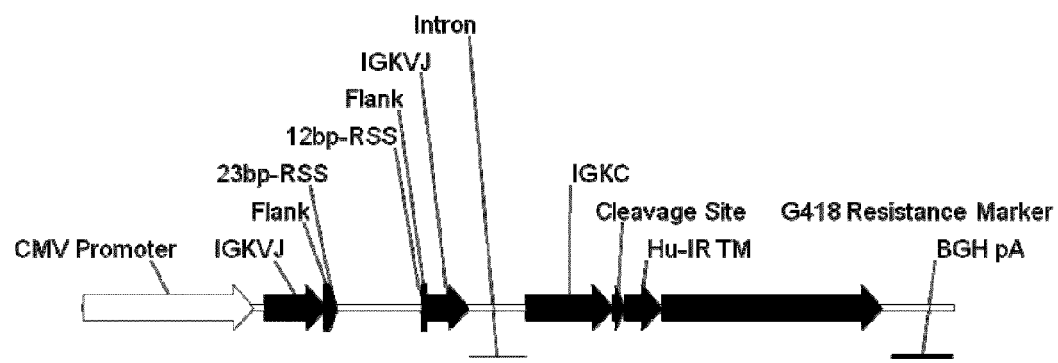
B.
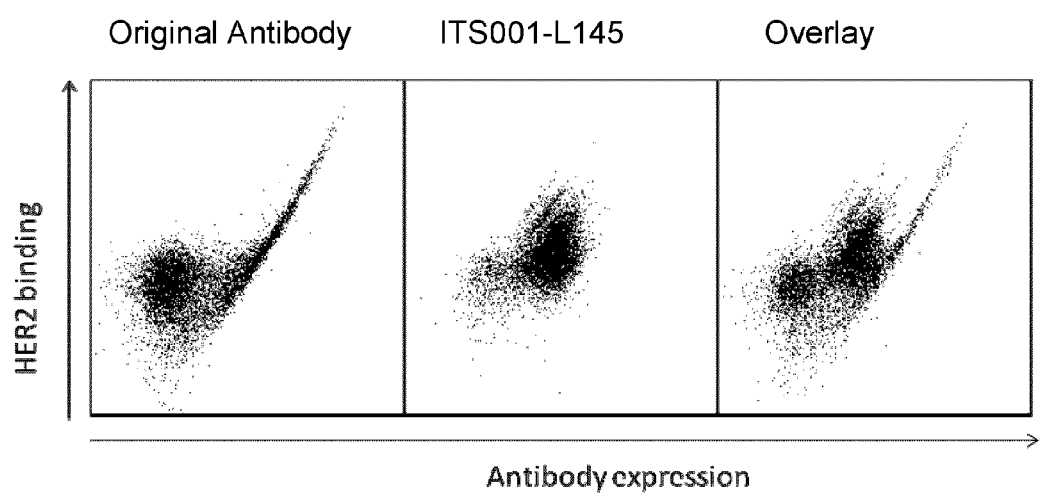
FIG. 21

A.
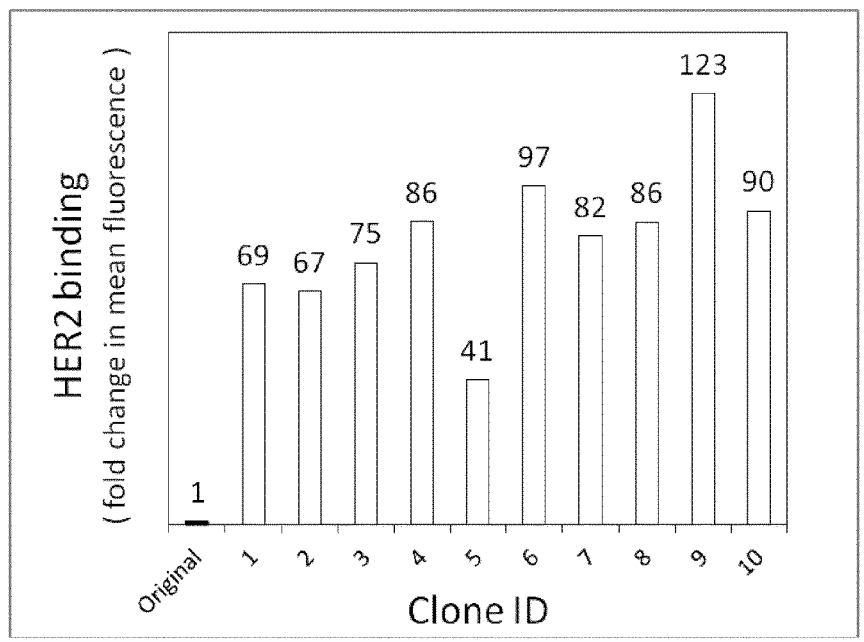
B.
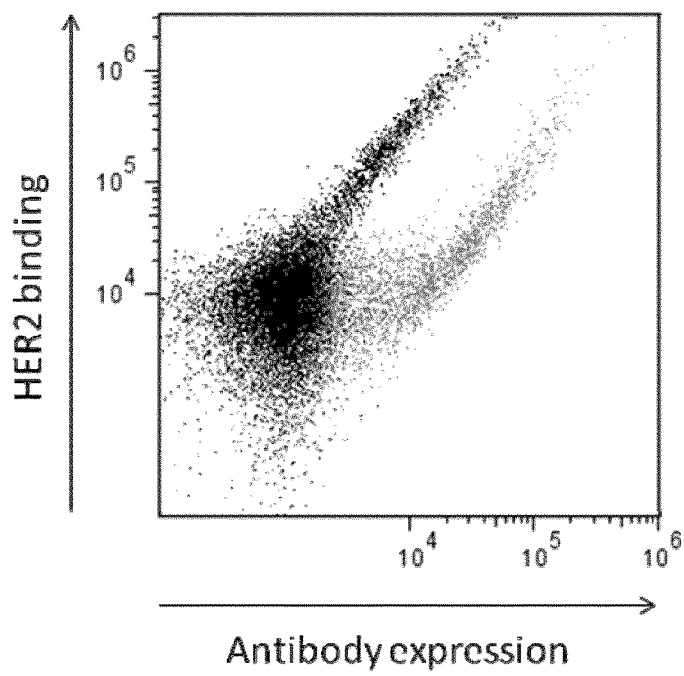
FIG. 22

A.
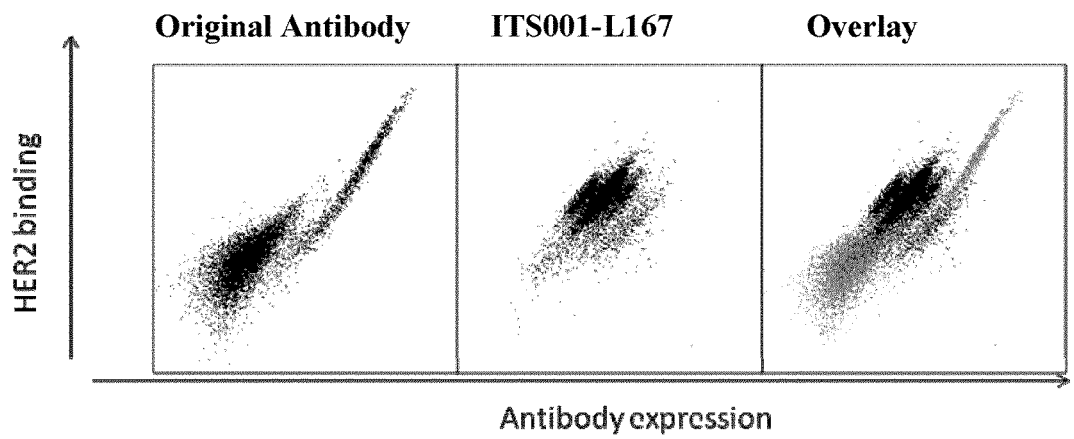
B.
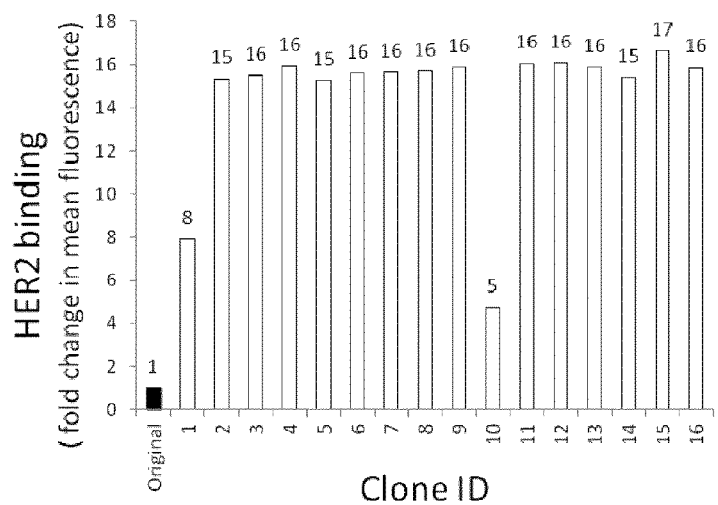
C.
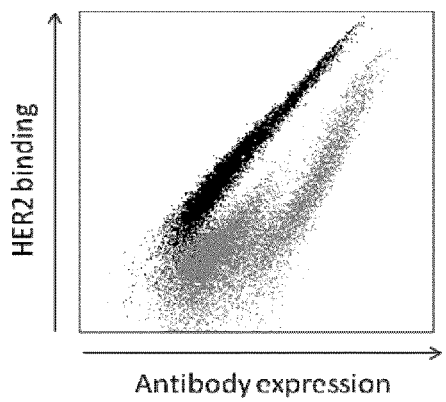
FIG. 23

SEQUENCE LISTING

```
<160> NUMBER OF SEQ ID NOS: 122

<210> SEQ ID NO 1
<211> LENGTH: 7611
<212> TYPE: DNA
<213> ORGANISM: Artificial sequence
<220> FEATURE:
<223> OTHER INFORMATION: E188 vector

<400> SEQUENCE: 1
ctaaattgta agcgttaata ttttgttaaa attcgcgtta aattttttgtt aaatcagctc      60 attttttaac caataggccg aaatcggcaa atcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa aggggatgt      240 gctgcaaggc gattaagttg ggtaacgcca gggttttccc agtcacgacg ttgtaaaacg      300
acggccagtg agcgcgacgt aatacgactc actatagggc gaattggcgg aaggccgtca      360
aggcctaggc gcgcctgaat aacttcgtat agcatacatt atagcaattt atcgaaaaag      420
cctgaactca ccgcgacatc cgtggagaaa ttcctcatcg aaaaattcga ctccgtgtcc      480
gatctcatgc agctgtccga gggcgaggag agtagagcat tctcattcga tgtgggcggg      540
agaggctacg tgctgagagt gaactcttgt gccgacggct tctacaagga ccgatacgtc      600
taccggcatt ttgcttccgc cgctctgcct attccagaag tcctggacat tggggagttt      660
agcgagtccc tcacttactg tattagccgg cgagcccagg gagtgacact ccaggatctg      720
cctgaaactg aactgcctgc tgtgctccag cctgtcgctg aggcaatgga tgctattgct      780
gctgccgatc tgagtcagac tagcggattc ggcccatttg acccccaggg cattggccag      840
tacacaacat ggcgagactt catctgtgct atcgccgatc ctcacgtgta ccattggcag      900
actgtgatgg acgatactgt gtctgcttct gtggcacagg cactcgacga actcatgctg      960
tgggctgagg actgtcctga agtgagacat ctggtccatg ccgatttttgg ctccaacaat     1020
```

```
gtgctcaccg ataacgggag aatcactgcc gtgatcgact ggagcgaggc aatgtttggc    1080
gattcccagt acgaagtggc caacatcttc ttttggcggc cttggctggc ttgtatggaa    1140
cagcagaccc ggtactttga acggcgccac cctgagctgg ctgggagtcc tagactgaga    1200
gcctacatgc tccgaattgg cctggatcag ctctaccagt cactggtgga tggcaatttc    1260
gacgatgctg cttgggcaca ggggcgctgt gatgctattg tccgatccgg cgctggaact    1320
gtggggagaa cacagatcgc taggagatcc gctgctgtct ggaccgatgg atgtgtggaa    1380
gtgctggccg atagtggaaa ccggaggcct tcaacccgac cccgggcaaa ggagtaatga    1440
ccgtttaaac ccgctgatca gcctcgactg tgccttctag ttgccagcca tctgttgttt    1500
gcccctcccc cgtgccttcc ttgaccctgg aaggtgccac tcccactgtc ctttcctaat    1560
aaaatgagga aattgcatcg cattgtctga gtaggtgtca ttctattctg ggggtgggg    1620 tggggcagga cagcaagggg gaggattggg aagacaatag caggcatgct ggggatgcgg    1680
tgggctctat ggggatcccg cgttgacatt gattattgac tagttattaa tagtaatcaa    1740 ttacgggtc attagttcat agcccatata tggagttccg cgttacataa cttacggtaa    1800
atggcccgcc tggctgaccg cccaacgacc cccgcccatt gacgtcaata atgacgtatg    1860
ttcccatagt aacgccaata gggactttcc attgacgtca atgggtggag tatttacggt    1920
aaactgccca cttggcagta catcaagtgt atcatatgcc aagtacgccc cctattgacg    1980
tcaatgacgg taaatggccc gcctggcatt atgcccagta catgacctta tgggactttc    2040
ctacttggca gtacatctac gtattagtca tcgctattac catggtgatg cggttttggc    2100
agtacatcaa tgggcgtgga tagcggtttg actcacgggg atttccaagt ctccacccca    2160
ttgacgtcaa tgggagtttg ttttggcacc aaaatcaacg ggactttcca aaatgtcgta    2220
acaactccgc cccattgacg caaatgggcg gtaggcgtgt acggtgggag gtctatataa    2280
gcagagctct ctggctaact agagaaccca ctgcttactg ctcgacgatc tgatcaagag    2340
acaggataag gagccgccac catggagttt ggctgagct ggcttttct tgtggctatt    2400 ttaaaaggtg tccagtgtta cccatacgat gttccagatt acgcttgtgc ccctcacagt    2460
ggtagtactc cactgtctgg gtgtacaaaa acctccctgc acgcctctct aacctcacaa    2520
ttctgtggcg gccgcgccgc caccatgatt gaacaagatg gattgcacgc aggttctccg    2580
gccgcttggg tggagaggct attcggctat gactgggcac aacagacaat cggctgctct    2640
gatgccgccg tgttccggct gtcagcgcag gggcgcccgg ttcttttgt caagaccgac    2700 ctgtccggtg ccctgaatga actgcaggac gaggcagcgc ggctatcgtg ctggccacg    2760 acgggcgttc cttgcgcagc tgtgctcgac gttgtcactg aagcgggaag ggactggctg    2820
ctattgggcg aagtgccggg gcaggatctc ctgtcatctc accttgctcc tgccgagaaa    2880
gtatccatca tggctgatgc aatgcggcgg ctgcatacgc ttgatccggc tacctgccca    2940
ttcgaccacc aagcgaaaca tcgcatcgag cgagcacgta ctcggatgga agccggtctt    3000
gtcgatcagg tgagtacagg aggtggagag tacgcgtaac acttaagcgt ctctccaagt    3060
gcaaagggac aggaggtttt tgttaagggc tgtatcactg tgagccagtt ccagtgcggc    3120
tccggctacc acagtgatac agcccttaac aaaaacccct actgcaacct ggcggtaaga    3180
gacgtccgga ggccagccct tctcatgttc agagaacatg gttaactggt taagtcatgt    3240
cgtcccacag gatgatctgg acgaagagca tcagggctc gcgccagccg aactgttcgc    3300
caggctcaag gcgcgcatgc ccgacggcga ggatctcgtc gtgacccatg gcgatgcctg    3360
cttgccgaat atcatggtgg aaaatggccg cttttctgga ttcatcgact gtggccggct    3420
```

```
gggtgtggcg gaccgctatc aggacatagc gttggctacc cgtgatattg ctgaagagct    3480
tggcggcgaa tgggctgacc gcttcctcgt gctttacggt atcgccgctc ccgattcgca    3540
gcgcatcgcc ttctatcgcc ttcttgacga gttcttctga gtcgactgca ggagtcccac    3600 tgcaccccc tcccagtctt ctctgtccag gcaccaggcc aggtatctgg ggtgtgcagc    3660
cggcctgggt ctggcctgag gccacaagcc cggggggtctg tgtggctggg gacagggacg    3720
ccggctgcct ctgctctgtg cttgggccat gtgacccatt cgagtgtcct gcacgggcac    3780 aggttttgt acacccagac agtggagtac taccactgtg ggctactgca tcagccagag    3840
atgggtgtgc gacggggaga tgattgcga ggacggcagc gacgaggcca attgtgccgg    3900
ctctgtgcct accgagccca atcttgtga caaaactcac acatgcccac cgtgcccagc    3960
acctgaactc ctgggggac cgtcagtctt cctcttcccc ccaaaaccca aggacaccct    4020
catgatctct agaacccctg aggtcacatg cgtggtggtg gacgtgagcc acgaagaccc    4080
tgaggtcaag ttcaactggt acgtggacgg cgtggaggtg cataatgcca agacaaagcc    4140
gcgggaggag cagtacaaca gcacgtaccg tgtggtcagc gtcctcaccg tcctgcacca    4200
ggactggctg aatggcaagg agtacaagtg caaggtgtcc aacaaagccc tcccagcccc    4260
catcgagaaa accatctcca aagccaaagg gcagccccga gaaccacagg tgtacaccct    4320 gccccatcc cgggatgagc tgaccaagaa ccaggtcagc ctgacctgcc tggtcaaagg    4380
cttctatccc agcgacatcg ccgtggagtg ggagagcaat gggcagccgg agaacaacta    4440
caagaccacg cctcccgtgc tggactccga cggctccttc ttcctctaca gcaagctcac    4500
cgtggacaag tctagatggc agcaggggaa cgtcttctca tgctccgtga tgcatgaggc    4560
tctgcacaac cactacacgc agaagagcct ctccctgtct ccgggcaaac tggctctcat    4620
tgtcctgggc ggcgtggctg cctgctgct gtttattggg ctgggcatct tcttttgtgt    4680
ccggtgtcgg cataggaggc gccaaggagg tggcggatct ggaggggag gatctggagg    4740 gggctcagga tcagggggag gatctggagg cggatcaact gagtacaaac ccactgtgag    4800
gctcgctact agagatgatg tgcctagagc tgtccgaact ctggctgctg ccttcgccga    4860
ttaccctgcc actcgccata ccgtcgatcc cgatcgccac attgaacgag tcaccgaact    4920
ccaggagctg tttctcacta gagtcgggct ggatattggc aaagtctggg tggccgatga    4980
cggagccgct gtcgctgtgt ggactacacc tgagtctgtg gaggctggcg ccgtgtttgc    5040
tgaaattgga cctcggatgg ctgaactgtc tggatctcga ctggctgccc agcagcagat    5100
ggagggactg ctggcaccc atagaccaaa ggaacctgcc tggtttctgg caactgtggg    5160
agtgtcaccc gatcatcagg gcaaaggact gggatctgcc gtggtgctcc ctggcgtgga    5220
ggccgctgaa cgagctggcg tccccgcttt tctcgaaact tctgcccccc gaaatctccc    5280
tttctacgaa cgactgggat tcactgtcac cgccgatgtc gaagtgcctg aggggcctag    5340
aacatggtgt atgaccccga aaccggagc ttaaccgttt aaaccgctg atcagcctcg    5400 actgtgcctt ctagttgcca gccatctgtt gtttgcccct ccccgtgcc ttccttgacc    5460 ctggaaggtg ccactcccac tgtccttttcc taataaaatg aggaaattgc atcgcattgt    5520
ctgagtaggt gtcattctat ctggggggt ggggtgggc aggacagcaa ggggaggat    5580 tgggaagaca atagcaggca tgctgggat gcggtgggct ctatggctcg agttaattaa    5640
ctggcctcat gggccttccg ctcactgccc gctttccagt cgggaaacct gtcgtgccag    5700
ctgcattaac atggtcatag ctgtttcctt gcgtattggg cgctctccgc ttcctcgctc    5760
```

```
actgactcgc tgcgctcggt cgttcgggta agcctggggg tgcctaatga gcaaaaggcc      5820
agcaaaaggc caggaaccgt aaaaaggccg cgttgctggc gttttttccat aggctccgcc     5880 cccctgacga gcatcacaaa aatcgacgct caagtcagag gtggcgaaac ccgacaggac      5940
tataaagata ccaggcgttt ccccctggaa gctccctcgt gcgctctcct gttccgaccc      6000
tgccgcttac cggatacctg tccgcctttc tcccttcggg aagcgtggcg ctttctcata      6060
gctcacgctg taggtatctc agttcggtgt aggtcgttcg ctccaagctg gctgtgtgc      6120 acgaaccccc cgttcagccc gaccgctgcg ccttatccgg taactatcgt cttgagtcca      6180
acccggtaag acacgactta tcgccactgg cagcagccac tggtaacagg attagcagag      6240
cgaggtatgt aggcggtgct acagagttct tgaagtggtg gcctaactac ggctacacta      6300
gaagaacagt atttggtatc tgcgctctgc tgaagccagt taccttcgga aaaagagttg      6360
gtagctcttg atccggcaaa caaaccaccg ctggtagcgg tggttttttt gtttgcaagc      6420
agcagattac gcgcagaaaa aaaggatctc aagaagatcc tttgatcttt tctacggggt      6480
ctgacgctca gtggaacgaa aactcacgtt aagggatttt ggtcatgaga ttatcaaaaa      6540
ggatcttcac ctagatcctt ttaaattaaa aatgaagttt taaatcaatc taaagtatat      6600
atgagtaaac ttggtctgac agttaccaat gcttaatcag tgaggcacct atctcagcga      6660
tctgtctatt tcgttcatcc atagttgcct gactccccgt cgtgtagata actacgatac      6720
gggagggctt accatctggc cccagtgctg caatgatacc gcgagaacca cgctcaccgg      6780
ctccagattt atcagcaata aaccagccag ccggaagggc cgagcgcaga agtggtcctg      6840
caactttatc cgcctccatc cagtctatta attgttgccg ggaagctaga gtaagtagtt      6900
cgccagttaa tagtttgcgc aacgttgttg ccattgctac aggcatcgtg gtgtcacgct      6960
cgtcgtttgg tatggcttca ttcagctccg gttcccaacg atcaaggcga gttacatgat      7020
cccccatgtt gtgcaaaaaa gcggttagct ccttcggtcc tccgatcgtt gtcagaagta      7080
agttggccgc agtgttatca ctcatggtta tggcagcact gcataattct cttactgtca      7140
tgccatccgt aagatgcttt tctgtgactg gtgagtactc aaccaagtca ttctgagaat      7200
agtgtatgcg gcgaccgagt tgctcttgcc cggcgtcaat acgggataat accgcgccac      7260
atagcagaac tttaaaagtg ctcatcattg gaaaacgttc ttcggggcga aaactctcaa      7320
ggatcttacc gctgttgaga tccagttcga tgtaacccac tcgtgcaccc aactgatctt      7380
cagcatcttt tactttcacc agcgtttctg ggtgagcaaa aacaggaagg caaaatgccg      7440
caaaaaaggg aataagggcg acacggaaat gttgaatact catactcttc ctttttcaat      7500
attattgaag catttatcag ggttattgtc tcatgagcgg atacatattt gaatgtattt      7560
agaaaaataa acaaataggg gttccgcgca catttccccg aaaagtgcca c              7611
```

<210> SEQ ID NO 2
<211> LENGTH: 12
<212> TYPE: DNA
<213> ORGANISM: Artificial sequence
<220> FEATURE:
<223> OTHER INFORMATION: RSS spacer sequence

<400> SEQUENCE: 2
atacagacct ta                                                         12

<210> SEQ ID NO 3
<211> LENGTH: 364
<212> TYPE: DNA
<213> ORGANISM: Artificial sequence
<220> FEATURE:
<223> OTHER INFORMATION: Immunoglobulin heavy chain

<400> SEQUENCE: 3

| | |
|---|---|
| caggtgcagc tggtgcagag cggcagcgag ctgaagaaac ctggcgcctc cgtgaaggtg | 60 |
| tcctgcaagg ccagcggcta caccttcacc agctacgcca tgaactgggt ccgccaggcc | 120 |
| ccaggccagg gactggaatg gatgggctgg atcaacacca caccggcaa ccccacctac | 180 |
| gcccagggct tcaccggcag attcgtgttc agcttcgaca ccagcgtgtc caccgcctac | 240 |
| ctgcagatct gtagcctgaa ggccgaggac accgccgtgt attactgtgc gagagggaca | 300 |
| gctatggtac gggctgaata cttccagcac tggggccagg gcaccctggt caccgtgtcc | 360 |
| tcag | 364 |

<210> SEQ ID NO 4
<211> LENGTH: 653
<212> TYPE: DNA
<213> ORGANISM: Artificial sequence
<220> FEATURE:
<223> OTHER INFORMATION: Immunoglobulin heavy chain with RSSs in CDR2

<400> SEQUENCE: 4

| | |
|---|---|
| caggtgcagc tggtgcagag cggcagcgag ctgaagaaac ctggcgcctc cgtgaaggtg | 60 |
| tcctgcaagg ccagcggcta caccttcacc agctacgcca tgaactgggt ccgccaggcc | 120 |
| ccaggccagg gactggaatg gatgggctgg atcaacacca ccacagtgg tagtactcca | 180 |
| ctgtctgggt gtacaaaaac ctccctgcac gcctctctaa cctcacaatt ctgtggcggc | 240 |
| cgctttgtag ccagaccctc ggtcaactgg atgtcacaac tggcacctga gattggaaac | 300 |
| ataaaaacaa atattcttac tattaatcat gttatcagag aacttccctg aagttccagt | 360 |
| cagtactgtg actagctaat tagtcagtta cttaagcgtc tatccaagtg caagggaca | 420 |
| ggaggttttt gttaagggct gtatcactgt gaccggcaac cccacctacg cccagggctt | 480 |
| caccggcaga ttcgtgttca gcttcgacac cagcgtgtcc accgcctacc tgcaaatctg | 540 |
| tagcctgaag gccgaggaca ccgccgtgta ttactgtgcg agagggacag ctatggtccg | 600 |
| ggctgaatac ttccagcact ggggccaggg caccctggtc accgtgtcct cag | 653 |

<210> SEQ ID NO 5
<211> LENGTH: 1086
<212> TYPE: DNA
<213> ORGANISM: Artificial sequence
<220> FEATURE:
<223> OTHER INFORMATION: Immunoglobulin heavy chain with RSSs in CDR1
       and CDR2

<400> SEQUENCE: 5

| | |
|---|---|
| caggtgcagc tggtgcagag cggcagcgag ctgaagaaac ctggcgcctc cgtgaaggtg | 60 |
| tcctgcaagg ccagcggcta caccttcacc agccacagtg gtagtactcc actgtctggg | 120 |
| tgtacaaaaa cctccctgca cgcctctcta acctcacaat tctgtggcgg ccgctttgta | 180 |
| gccagaccct cggtcaactg gatgtcacaa ctggcacctg agattggaaa cataaaaaca | 240 |
| aatattctta ctattaatca tgttatcaga gaacttccct gaagttccag tcagtactgt | 300 |
| gactagctaa ttagtcagtt acttaagcgt ctatccaagt gcaaagggac aggaggtttt | 360 |
| tgttaagggc tgtatcactg tgagctacgc catgaactgg gtccgccagg ccccaggcca | 420 |
| gggacttgaa tggatgggct ggatcaacac caacacccac agtgatacag cccttaacaa | 480 |
| aaaccccta tgcaacctgg cggtaataga cgtccggaag cacactggct gagtaaattc | 540 |

-continued

```
ctagtgttct ccatccttac ctcggagcca gagtagcagg agccactagc cagcttgggt      600
cttcctatcg cgagtcgtat taatttcgat aagccagcaa gcagtgggtt ctctagttag      660
ccagctgcct cctttctctg ggcccagcgt cctctgtcct ggagctggga gataatgtcc      720
gggggctcct tggtctgcgc tgggcaaagg gtgggcagag tcatgcttgt gctggggaca      780
aaatgacctt gggacacggt cgacgggctg gctgccacgg ccggcccggg acagtcggag      840
agtcaggttt ttgtacaccc agacagtgga gtactaccac tgtgaccggc aaccccacct      900
acgcccaggg cttcaccggc agattcgtgt tcagcttcga caccagcgtg tccaccgcct      960
acctgcaaat ctgtagcctg aaggccgagg acaccgccgt gtattactgt gcgagaggga      1020
cagctatggt ccgggctgaa tacttccagc actggggcca gggcaccctg gtcaccgtgt      1080
cctcag                                                                1086
```

<210> SEQ ID NO 6
<211> LENGTH: 289
<212> TYPE: DNA
<213> ORGANISM: Artificial sequence
<220> FEATURE:
<223> OTHER INFORMATION: Heavy chain CDR2 diversifying cassette

<400> SEQUENCE: 6

```
cacagtggta gtactccact gtctgggtgt acaaaaacct ccctgcacgc ctctctaacc       60
tcacaattct gtggcggccg ctttgtagcc agaccctcgg tcaactggat gtcacaactg      120
gcacctgaga ttggaaacat aaaaacaaat attcttacta ttaatcatgt tatcagagaa      180
cttccctgaa gttccagtca gtactgtgac tagctaatta gtcagttact taagcgtcta      240
tccaagtgca aagggacagg aggttttttgt taagggctgt atcactgtg                 289
```

<210> SEQ ID NO 7
<211> LENGTH: 292
<212> TYPE: DNA
<213> ORGANISM: Artificial sequence
<220> FEATURE:
<223> OTHER INFORMATION: Heavy chain CDR1 diversifying cassette

<400> SEQUENCE: 7

```
agccacagtg gtagtactcc actgtctggg tgtacaaaaa cctccctgca cgcctctcta       60
acctcacaat tctgtggcgg ccgctttgta gccagaccct cggtcaactg gatgtcacaa      120
ctggcacctg agattggaaa cataaaaaca aatattctta ctattaatca tgttatcaga      180
gaacttccct gaagttccag tcagtactgt gactagctaa ttagtcagtt acttaagcgt      240
ctatccaagt gcaagggac aggaggtttt tgttaagggc tgtatcactg tg               292
```

<210> SEQ ID NO 8
<211> LENGTH: 430
<212> TYPE: DNA
<213> ORGANISM: Artificial sequence
<220> FEATURE:
<223> OTHER INFORMATION: Heavy chain CDR2 diversifying cassette

<400> SEQUENCE: 8

```
acccacagtg atacagccct aacaaaaac ccctactgca acctggcggt aatagacgtc        60
cggaagcaca ctggctgagt aaattcctag tgttctccat ccttacctcg gagccagagt      120
agcaggagcc actagccagc ttgggtcttc ctatcgcgag tcgtattaat ttcgataagc      180
cagcaagcag tgggttctct agttagccag ctgcctcctt tctctgggcc cagcgtcctc      240
```

```
tgtcctggag ctgggagata atgtccgggg gctccttggt ctgcgctggg caaagggtgg    300
gcagagtcat gcttgtgctg gggacaaaat gaccttggga cacggtcgac gggctggctg    360
ccacggccgg cccgggacag tcggagagtc aggttttgt acacccagac agtggagtac     420
taccactgtg                                                            430

<210> SEQ ID NO 9
<211> LENGTH: 12
<212> TYPE: DNA
<213> ORGANISM: Artificial sequence
<220> FEATURE:
<223> OTHER INFORMATION: RSS spacer sequence

<400> SEQUENCE: 9
ctacagactg ga                                                         12

<210> SEQ ID NO 10
<211> LENGTH: 12
<212> TYPE: DNA
<213> ORGANISM: Artificial sequence
<220> FEATURE:
<223> OTHER INFORMATION: RSS spacer sequence

<400> SEQUENCE: 10
ctccagggct ga                                                         12

<210> SEQ ID NO 11
<211> LENGTH: 12
<212> TYPE: DNA
<213> ORGANISM: Artificial sequence
<220> FEATURE:
<223> OTHER INFORMATION: RSS spacer sequence

<400> SEQUENCE: 11
gtacagacca at                                                         12

<210> SEQ ID NO 12
<211> LENGTH: 23
<212> TYPE: DNA
<213> ORGANISM: Artificial sequence
<220> FEATURE:
<223> OTHER INFORMATION: RSS spacer sequence

<400> SEQUENCE: 12
gtagtactcc actgtctggc tgt                                             23

<210> SEQ ID NO 13
<211> LENGTH: 23
<212> TYPE: DNA
<213> ORGANISM: Artificial sequence
<220> FEATURE:
<223> OTHER INFORMATION: RSS spacer sequence

<400> SEQUENCE: 13
gccgggcccc gcggcccggc ggc                                             23

<210> SEQ ID NO 14
<211> LENGTH: 23
<212> TYPE: DNA
<213> ORGANISM: Artificial sequence
<220> FEATURE:
<223> OTHER INFORMATION: RSS spacer sequence

<400> SEQUENCE: 14
ttgcaaccac atcctgagtg tgt                                             23
```

<210> SEQ ID NO 15
<211> LENGTH: 23
<212> TYPE: DNA
<213> ORGANISM: Artificial sequence
<220> FEATURE:
<223> OTHER INFORMATION: RSS spacer sequence

<400> SEQUENCE: 15
acggagataa aggaggaagc agg                                              23

<210> SEQ ID NO 16
<211> LENGTH: 10
<212> TYPE: DNA
<213> ORGANISM: Artificial sequence
<220> FEATURE:
<223> OTHER INFORMATION: Avimer Loop 1 addition sequence

<400> SEQUENCE: 16
agggccaaga                                                             10

<210> SEQ ID NO 17
<211> LENGTH: 14
<212> TYPE: DNA
<213> ORGANISM: Artificial sequence
<220> FEATURE:
<223> OTHER INFORMATION: Avimer Loop 1 addition sequence

<400> SEQUENCE: 17 taggggggttc cagt                                                       14

<210> SEQ ID NO 18
<211> LENGTH: 14
<212> TYPE: DNA
<213> ORGANISM: Artificial sequence
<220> FEATURE:
<223> OTHER INFORMATION: Avimer Loop 2 addition sequence

<400> SEQUENCE: 18
tggggttaag cctc                                                        14

<210> SEQ ID NO 19
<211> LENGTH: 16
<212> TYPE: DNA
<213> ORGANISM: Artificial sequence
<220> FEATURE:
<223> OTHER INFORMATION: Avimer Loop 2 addition sequence

<400> SEQUENCE: 19
ccctccgtcc tacctc                                                      16

<210> SEQ ID NO 20
<211> LENGTH: 18
<212> TYPE: DNA
<213> ORGANISM: Artificial sequence
<220> FEATURE:
<223> OTHER INFORMATION: Avimer Loop 2 addition sequence

<400> SEQUENCE: 20
tccagtgcgg ctccggga                                                    18

<210> SEQ ID NO 21
<211> LENGTH: 17
<212> TYPE: DNA
<213> ORGANISM: Artificial sequence
<220> FEATURE:

<210> SEQ ID NO 22
<211> LENGTH: 26
<212> TYPE: PRT
<213> ORGANISM: Artificial sequence
<220> FEATURE:
<223> OTHER INFORMATION: Avimer Loop 2 addition sequence

<400> SEQUENCE: 21
ggagccgcac tggaact                                              17

<210> SEQ ID NO 22
<211> LENGTH: 26
<212> TYPE: PRT
<213> ORGANISM: Artificial sequence
<220> FEATURE:
<223> OTHER INFORMATION: Single A Domain Avimer Parent

<400> SEQUENCE: 22

Asp Tyr Ala Cys Ala Pro Ser Gln Phe Gln Cys Gly Ser Gly Tyr Gly
1               5                   10                  15

Tyr Cys Ile Ser Gln Arg Trp Val Cys Asp
            20                  25

<210> SEQ ID NO 23
<211> LENGTH: 22
<212> TYPE: PRT
<213> ORGANISM: Artificial sequence
<220> FEATURE:
<223> OTHER INFORMATION: Single A Domain Avimer Variant

<400> SEQUENCE: 23

Asp Tyr Ala Phe Gln Phe Gln Cys Gly Ser Gly Tyr Asn Cys Ile Ser
1               5                   10                  15

Gln Arg Trp Val Cys Asp
            20

<210> SEQ ID NO 24
<211> LENGTH: 24
<212> TYPE: PRT
<213> ORGANISM: Artificial sequence
<220> FEATURE:
<223> OTHER INFORMATION: Single A Domain Avimer Variant

<400> SEQUENCE: 24

Asp Tyr Ala Cys Ala Pro Thr Ser Ser Ser Ala Ala Pro Ala Tyr Cys
1               5                   10                  15

Ile Ser Gln Arg Trp Val Cys Asp
            20

<210> SEQ ID NO 25
<211> LENGTH: 26
<212> TYPE: PRT
<213> ORGANISM: Artificial sequence
<220> FEATURE:
<223> OTHER INFORMATION: Single A Domain Avimer Variant

<400> SEQUENCE: 25

Asp Tyr Ala Cys Ala Pro Arg Arg Gln Phe Gln Cys Gly Ser Gly Tyr
1               5                   10                  15

Tyr Cys Ile Ser Gln Arg Trp Val Cys Asp
            20                  25

<210> SEQ ID NO 26
<211> LENGTH: 26
<212> TYPE: PRT
<213> ORGANISM: Artificial sequence
<220> FEATURE:
<223> OTHER INFORMATION: Single A Domain Avimer Variant

<400> SEQUENCE: 26

Asp Tyr Ala Cys Ala Leu Leu Ala Ser Ser Ala Ala Pro Ala Thr
1               5                   10                  15

Tyr Cys Ile Ser Gln Arg Trp Val Cys Asp
            20                  25

<210> SEQ ID NO 27
<211> LENGTH: 23
<212> TYPE: PRT
<213> ORGANISM: Artificial sequence
<220> FEATURE:
<223> OTHER INFORMATION: Single A Domain Avimer Variant

<400> SEQUENCE: 27

Asp Tyr Ala Cys Ala Gln Asp Ala Ala Pro Ala Thr Ser Tyr Cys Ile
1               5                   10                  15

Ser Gln Arg Trp Val Cys Asp
            20

<210> SEQ ID NO 28
<211> LENGTH: 2425
<212> TYPE: DNA
<213> ORGANISM: Artificial sequence
<220> FEATURE:
<223> OTHER INFORMATION: Partial nucleotide sequence of avimer construct
      E188

<400> SEQUENCE: 28
gccgccacca tggagtttgg gctgagctgg cttttcttg tggctatttt aaaaggtgtc      60
cagtgttacc catacgatgt tccagattac gcttgtgccc ctcacagtgg tagtactcca    120
ctgtctgggt gtacaaaaac ctccctgcac gcctctctaa cctcacaatt ctgtggcggc    180
cgcgccgcca ccatgattga caagatgga ttgcacgcag ttctccggc cgcttgggtg     240 gagaggctat tcggctatga ctgggcacaa cagacaatcg ctgctctga tgccgccgtg    300 ttccggctgt cagcgcaggg gcgcccggtt cttttgtca agaccgacct gtccggtgcc    360
ctgaatgaac tgcaggacga ggcagcgcgg ctatcgtggc tggccacgac gggcgttcct    420
tgcgcagctg tgctcgacgt tgtcactgaa gcgggaaggg actggctgct attgggcgaa    480
gtgccggggc aggatctcct gtcatctcac cttgctcctg ccgagaaagt atccatcatg    540
gctgatgcaa tgcggcggct gcatacgctt gatccggcta cctgcccatt cgaccaccaa    600
gcgaaacatc gcatcgagcg agcacgtact cggatggaag ccggtcttgt cgatcaggtg    660
agtacaggag gtggagagta cgcgtaacac ttaagcgtct ctccaagtgc aaagggacag    720
gaggtttttg ttaagggctg tatcactgtg agccagttcc agtgcggctc cggctaccac    780
agtgatacag cccttaacaa aaacccctac tgcaacctgg cggtaagaga cgtccggagg    840
ccagcccttc tcatgttcag agaacatggt taactggtta agtcatgtcg tcccacagga    900
tgatctggac gaagagcatc aggggctcgc gccagccgaa ctgttcgcca ggctcaaggc    960
gcgcatgccc gacggcgagg atctcgtcgt gacccatggc gatgcctgct tgccgaatat   1020
catggtggaa aatggccgct tttctggatt catcgactgt ggccggctgg gtgtggcgga   1080
ccgctatcag gacatagcgt tggctacccg tgatattgct gaagagcttg gcggcgaatg   1140
ggctgaccgc ttcctcgtgc tttacggtat cgccgctccc gattcgcagc gcatcgcctt   1200
ctatcgcctt cttgacgagt tcttctgagt cgactgcagg agtcccactg cacccccctc   1260
ccagtcttct ctgtccaggc accaggccag gtatctgggg tgtgcagccg gcctgggtcc   1320
ggcctgaggc cacaagcccg ggggtctgtg tggctgggga cagggacgcc ggctgcctct   1380

-continued

```
gctctgtgct tgggccatgt gacccattcg agtgtcctgc acgggcacag gtttttgtac    1440
acccagacag tggagtacta ccactgtggg ctactgcatc agccagagat gggtgtgcga    1500
cggggagaat gattgcgagg acggcagcga cgaggccaat tgtgccggct ctgtgcctac    1560
cgagcccaaa tcttgtgaca aaactcacac atgcccaccg tgcccagcac ctgaactcct    1620
ggggggaccg tcagtcttcc tcttcccccc aaaacccaag gacaccctca tgatctctag    1680
aacccctgag gtcacatgcg tggtggtgga cgtgagccac gaagaccctg aggtcaagtt    1740
caactggtac gtggacggcg tggaggtgca taatgccaag acaaagccgc gggaggagca    1800
gtacaacagc acgtaccgtg tggtcagcgt cctcaccgtc ctgcaccagg actggctgaa    1860
tggcaaggag tacaagtgca aggtgtccaa caaagccctc ccagccccca tcgagaaaac    1920
catctccaaa gccaaagggc agccccgaga accacaggtg tacaccctgc ccccatcccg    1980
ggatgagctg accaagaacc aggtcagcct gacctgcctg gtcaaaggct tctatcccag    2040
cgacatcgcc gtggagtggg agagcaatgg gcagccggag aacaactaca agaccacgcc    2100
tcccgtgctg gactccgacg gctccttctt cctctacagc aagctcaccg tggacaagtc    2160
tagatggcag caggggaacg tcttctcatg ctccgtgatg catgaggctc tgcacaacca    2220
ctacacgcag aagagcctct ccctgtctcc gggcaaactg gctctcattg tcctgggcgg    2280
cgtggctggc ctgctgctgt ttattgggct gggcatcttc ttttgtgtcc ggtgtcggca    2340
taggaggcgc caaggaggtg gcggatctgg aggggagga tctggagggg gctcaggatc    2400 aggggggagga tctggaggcg gatca                                         2425
```

<210> SEQ ID NO 29
<211> LENGTH: 2533
<212> TYPE: DNA
<213> ORGANISM: Artificial sequence
<220> FEATURE:
<223> OTHER INFORMATION: Partial nucleotide sequence of avimer construct E189

<400> SEQUENCE: 29

```
gccgccacca tggagtttgg gctgagctgg cttttcttg tggctatttt aaaaggtgtc      60
cagtgttacc catacgatgt tccagattac gcttgcctgc cccacagtgg tagtactcca    120
ctgtctgggt gtacaaaaac ctccctgcac gcctctctaa cctcacaatt ctgtggcggc    180
cgcgccgcca ccatgattga acaagatgga ttgcacgcag gttctccggc cgcttgggtg    240
gagaggctat tcggctatga ctgggcacaa cagacaatcg gctgctctga tgccgccgtg    300
ttccggctgt cagcgcaggg gcgcccggtt cttttgtca agaccgacct gtccggtgcc    360
ctgaatgaac tgcaggacga ggcagcgcgg ctatcgtggc tggccacgac gggcgttcct    420
tgcgcagctg tgctcgacgt tgtcactgaa gcgggaaggg actggctgct attgggcgaa    480
gtgccggggc aggatctcct gtcatctcac cttgctcctg ccgagaaagt atccatcatg    540
gctgatgcaa tgcggcggct gcatacgctt gatccggcta cctgcccatt cgaccaccaa    600
gcgaaacatc gcatcgagcg agcacgtact cggatggaag ccggtcttgt cgatcaggtg    660
agtacaggag gtgagagta cgcgtaacac ttaagcgtct ctccaagtgc aaagggacag    720 gaggttttg ttaagggctg tatcactgtg gaccagttca gatgcggcaa cggccagtgc    780 atcccctgg attgggtgtg cgacggcgtg aacgactgcc ccgattccga tgaggaaggc    840
tgccccccta gaacctgtgc ccctagccag cacagtgata cagcccttaa caaaaacccc    900
tactgcaacc tggcggtaag agacgtccgg aggccagccc ttctcatgtt cagagaacat    960
```

-continued

```
ggttaactgg ttaagtcatg tcgtcccaca ggatgatctg gacgaagagc atcagggct    1020 cgcgccagcc gaactgttcg ccaggctcaa ggcgcgcatg cccgacggcg aggatctcgt    1080
cgtgacccat ggcgatgcct gcttgccgaa tatcatggtg gaaaatggcc gcttttctgg    1140
attcatcgac tgtggccggc tgggtgtggc ggaccgctat caggacatag cgttggctac    1200
ccgtgatatt gctgaagagc ttggcggcga atgggctgac cgcttcctcg tgctttacgg    1260
tatcgccgct cccgattcgc agcgcatcgc cttctatcgc cttcttgacg agttcttctg    1320
agtcgactgc aggagtccca ctgcaccccc ctcccagtct tctctgtcca ggcaccaggc    1380
caggtatctg gggtgtgcag ccggcctggg tctggcctga ggccacaagc ccgggggtct    1440
gtgtggctgg ggacagggac gccggctgcc tctgctctgt gcttgggcca tgtgacccat    1500
tcgagtgtcc tgcacgggca caggttttg tacacccaga cagtgagta ctaccactgt    1560 gttccagtgc ggctccggct actgcatcag ccagagatgg gtgtgcgacg gggagaatga    1620
ttgcgaggac ggcagcgacg aggccaattg tgccggctct gtgcctaccg agcccaaatc    1680
ttgtgacaaa actcacacat gcccaccgtg cccagcacct gaactcctgg ggggaccgtc    1740
agtcttcctc ttccccccaa aacccaagga caccctcatg atctctagaa cccctgaggt    1800
cacatgcgtg gtggtggacg tgagccacga agaccctgag gtcaagttca actggtacgt    1860
ggacggcgtg gaggtgcata atgccaagac aaagccgcgg gaggagcagt acaacagcac    1920
gtaccgtgtg gtcagcgtcc tcaccgtcct gcaccaggac tggctgaatg gcaaggagta    1980
caagtgcaag gtgtccaaca aagccctccc agccccatc gagaaaacca tctccaaagc    2040
caaagggcag ccccgagaac cacaggtgta caccctgccc ccatcccggg atgagctgac    2100
caagaaccag gtcagcctga cctgcctggt caaaggcttc tatcccagcg acatcgccgt    2160
ggagtgggag agcaatgggc agccggagaa caactacaag accacgcctc ccgtgctgga    2220
ctccgacggc tccttcttcc tctacagcaa gctcaccgtg gacaagagtca gatggcagca    2280 ggggaacgtc ttctcatgct ccgtgatgca tgaggctctg cacaaccact acacgcagaa    2340
gagcctctcc ctgtctccgg gcaaactggc tctcattgtc ctgggcggcg tggctggcct    2400 gctgctgtttt attgggctgg gcatcttctt ttgtgtccgg tgtcggcata ggaggcgcca    2460
aggaggtggc ggatctggag ggggaggatc tgggaggggc tcaggatcag ggggaggatc    2520
tggaggcgga tca                                                       2533
```

```
<210> SEQ ID NO 30
<211> LENGTH: 29
<212> TYPE: DNA
<213> ORGANISM: Artificial sequence
<220> FEATURE:
<223> OTHER INFORMATION: Primer MG59

<400> SEQUENCE: 30
tcttggcatt atgcacctcc acgccgtcc                                        29

<210> SEQ ID NO 31
<211> LENGTH: 49
<212> TYPE: DNA
<213> ORGANISM: Artificial sequence
<220> FEATURE:
<223> OTHER INFORMATION: Primer MG301

<400> SEQUENCE: 31
gagagagatt ggtctcgaga acccactgct tactgctcga cgatctgat                 49
```

<210> SEQ ID NO 32
<211> LENGTH: 30
<212> TYPE: DNA
<213> ORGANISM: Artificial sequence
<220> FEATURE:
<223> OTHER INFORMATION: Primer MG58

<400> SEQUENCE: 32
gtcttcgtgg ctcacgtcca ccaccacgca         30

<210> SEQ ID NO 33
<211> LENGTH: 29
<212> TYPE: DNA
<213> ORGANISM: Artificial sequence
<220> FEATURE:
<223> OTHER INFORMATION: Primer MG60

<400> SEQUENCE: 33
ctgacctggt tcttggtcag ctcatcccg          29

<210> SEQ ID NO 34
<211> LENGTH: 279
<212> TYPE: DNA
<213> ORGANISM: Artificial sequence
<220> FEATURE:
<223> OTHER INFORMATION: 10Fn3 coding sequence

<400> SEQUENCE: 34
tccgatgtgc ccagggacct ggaagtggtg gccgccacac ctaccagcct gctgatctct    60
tgggatgccc ctgccgtgac cgtgcggtac tacagaatca cctacggcga gacaggcggc   120
aacagccccg tgcaggagtt tacagtgccc ggcagcaaga gcaccgccac catctctgga   180
ctgaagcccg gcgtggacta caccatcacc gtgtacgccg tgacaggcag aggcgacagc   240
cctgccagca gcaagcccat cagcatcaac taccggacc                          279

<210> SEQ ID NO 35
<211> LENGTH: 6139
<212> TYPE: DNA
<213> ORGANISM: Artificial sequence
<220> FEATURE:
<223> OTHER INFORMATION: Acceptor vector

<400> SEQUENCE: 35
ctaaattgta agcgttaata ttttgttaaa attcgcgtta aattttttgtt aaatcagctc    60 attttttaac caataggccg aaatcggcaa aatcccttat aaatcaaaag aatagaccga   120
gatagggttg agtggccgct acagggcgct cccattcgcc attcaggctg cgcaactgtt   180
gggaagggcg tttcggtgcg ggcctcttcg ctattacgcc agctggcgaa agggggatgt   240
gctgcaaggc gattaagttg ggtaacgcca gggttttccc agtcacgacg ttgtaaaacg   300
acggccagtg agcgcgacgt aatacgactc actatagggc gaattggcgg aaggccgtca   360
aggcctaggc gcgcctgaat aacttcgtat agcatacatt atagcaattt atcgaaaaag   420
cctgaactca ccgcgacatc cgtggagaaa ttcctcatcg aaaaattcga ctccgtgtcc   480
gatctcatgc agctgtccga gggcgaggag agtagagcat tctcattcga tgtgggcggg   540
agaggctacg tgctgagagt gaactcttgt gccgacggct ctacaaggac cgatacgtc    600 taccggcatt tgcttccgc cgctctgcct attccagaag tcctggacat tggggagttt   660
agcgagtccc tcacttactg tattagcggg cgagcccagg gagtgacact ccaggatctg   720
cctgaaactg aactgcctgc tgtgctccag cctgtcgctg aggcaatgga tgctattgct   780

```
gctgccgatc tgagtcagac tagcggattc ggcccatttg gaccccaggg cattggccag      840
tacacaacat ggcgagactt catctgtgct atcgccgatc ctcacgtgta ccattggcag      900
actgtgatgg acgatactgt gtctgcttct gtggcacagg cactcgacga actcatgctg      960
tgggctgagg actgtcctga agtgagacat ctggtccatg ccgattttgg ctccaacaat     1020
gtgctcaccg ataacgggag aatcactgcc gtgatcgact ggagcgaggc aatgtttggc     1080
gattcccagt acgaagtggc caacatcttc ttttggcggc cttggctggc ttgtatggaa     1140
cagcagaccc ggtactttga acggcgccac cctgagctgg ctgggagtcc tagactgaga     1200
gcctacatgc tccgaattgg cctggatcag ctctaccagt cactggtgga tggcaatttc     1260
gacgatgctg cttgggcaca ggggcgctgt gatgctattg tccgatccgg cgctggaact     1320
gtggggagaa cacagatcgc taggagatcc gctgctgtct ggaccgatgg atgtgtggaa     1380
gtgctggccg atagtggaaa ccggaggcct caacccgac cccgggcaaa ggagtaatga     1440
ccgtttaaac ccgctgatca gcctcgactg tgccttctag ttgccagcca tctgttgttt     1500
gcccctcccc cgtgccttcc ttgaccctgg aaggtgccac tcccactgtc ctttcctaat     1560
aaaatgagga aattgcatcg cattgtctga gtaggtgtca ttctattctg ggggtgggg     1620 tggggcagga cagcaagggg gaggattggg aagacaatag caggcatgct ggggatgcgg     1680
tgggctctat ggggatcccg cgttgacatt gattattgac tagttattaa tagtaatcaa     1740
ttacggggtc attagttcat agcccatata tggagttccg cgttacataa cttacggtaa     1800
atggcccgcc tggctgaccg cccaacgacc cccgcccatt gacgtcaata atgacgtatg     1860
ttcccatagt aacgccaata gggactttcc attgacgtca atgggtggag tatttacggt     1920
aaactgccca cttggcagta catcaagtgt atcatatgcc aagtacgccc cctattgacg     1980
tcaatgacgg taaatggccc gcctggcatt atgcccagta catgacctta tgggactttc     2040
ctacttggca gtacatctac gtattagtca tcgctattac catggtgatg cggttttggc     2100
agtacatcaa tgggcgtgga tagcggtttg actcacgggg atttccaagt ctccacccca     2160
ttgacgtcaa tgggagtttg ttttggcacc aaaatcaacg ggactttcca aaatgtcgta     2220
acaactccgc cccattgacg caaatgggcg gtaggcgtgt acggtgggag gtctatataa     2280
gcagagctct ctggctaact agagaaccca ctgcttactg ctcgacgatc tgatcaagag     2340
acaggataag gagccgccac catggagttt ggctgagct ggcttttct tgtggctatt     2400 ttaaaaggtg tccagtgtag agaccggaag agattggtac cgagcccaaa tcttgtgaca     2460
aaactcacac atgcccaccg tgcccagcac ctgaactcct gggggaccg tcagtcttcc     2520 tcttcccccc aaaacccaag gacaccctca tgatctctag aacccctgag gtcacatgcg     2580
tggtggtgga cgtgagccac gaagaccctg aggtcaagtt caactggtac gtggacggcg     2640
tggaggtgca taatgccaag acaaagccgc gggaggagca gtacaacagc acgtaccgtg     2700
tggtcagcgt cctcaccgtc ctgcaccagg actggctgaa tggcaaggag tacaagtgca     2760
aggtgtccaa caaagccctc ccagccccca tcgagaaaac catctccaaa gccaagggc     2820 agccccgaga accacaggtg tacaccctgc cccatcccg ggatgagctg accaagaacc     2880
aggtcagcct gacctgcctg gtcaaaggct tctatcccag cgacatcgcc gtggagtggg     2940
agagcaatgg gcagccggag aacaactaca agaccacgcc tcccgtgctg gactccgacg     3000
gctccttctt cctctacagc aagctcaccg tggacaagtc tagatggcag caggggaacg     3060
tcttctcatg ctccgtgatg catgaggctc tgcacaacca ctacacgcag aagagcctct     3120
```

```
ccctgtctcc gggcaaactg gctctcattg tcctgggcgg cgtggctggc ctgctgctgt    3180
ttattgggct gggcatcttc ttttgtgtcc ggtgtcggca taggaggcgc caaggaggtg    3240
gcggatctgg agggggagga tctggagggg gctcaggatc agggggagga tctggaggcg    3300
gatcaactga gtacaaaccc actgtgaggc tcgctactag agatgatgtg cctagagctg    3360
tccgaactct ggctgctgcc ttcgccgatt accctgccac tcgccatacc gtcgatcccg    3420
atcgccacat tgaacgagtc accgaactcc aggagctgtt tctcactaga gtcgggctgg    3480
atattggcaa agtctgggtg gccgatgacg gagccgctgt cgctgtgtgg actacacctg    3540
agtctgtgga ggctggcgcc gtgtttgctg aaattggacc tcggatggct gaactgtctg    3600
gatctcgact ggctgcccag cagcagatgg agggactgct ggcaccccat agaccaaagg    3660
aacctgcctg gtttctggca actgtgggag tgtcacccga tcatcagggc aaaggactgg    3720
gatctgccgt ggtgctccct ggcgtggagg ccgctgaacg agctggcgtc cccgcttttc    3780
tcgaaacttc tgcccccga aatctcccctt tctacgaacg actgggattc actgtcaccg    3840
ccgatgtcga agtgcctgag gggcctagaa catggtgtat gacccggaaa cccggagctt    3900
aaccgtttaa accgctgat cagcctcgac tgtgccttct agttgccagc catctgttgt    3960
ttgcccctcc ccgtgccttt ccttgaccct ggaaggtgcc actcccactg tcctttccta    4020
ataaaatgag gaaattgcat cgcattgtct gagtaggtgt cattctattc tggggggtgg    4080
ggtggggcag gacagcaagg gggaggattg gaagacaat agcaggcatg ctggggatgc    4140
ggtgggctct atggctcgag ttaattaact ggcctcatgg gccttccgct cactgcccgc    4200
tttccagtcg ggaaacctgt cgtgccagct gcattaacat ggtcatagct gtttccttgc    4260
gtattgggcg ctctccgctt cctcgctcac tgactcgctg cgctcggtcg ttcgggtaaa    4320
gcctggggtg cctaatgagc aaaaggccag caaaaggcca ggaaccgtaa aaaggccgcg    4380
ttgctggcgt ttttccatag gctccgcccc cctgacgagc atcacaaaaa tcgacgctca    4440
agtcagaggt ggcgaaaccc gacaggacta taaagatacc aggcgtttcc ccctggaagc    4500
tccctcgtgc gctctcctgt tccgaccctg ccgcttaccg gatacctgtc cgcctttctc    4560
ccttcgggaa gcgtggcgct ttctcatagc tcacgctgta ggtatctcag ttcggtgtag    4620
gtcgttcgct ccaagctggg ctgtgtgcac gaaccccccg ttcagcccga ccgctgcgcc    4680
ttatccggta actatcgtct tgagtccaac ccggtaagac acgacttatc gccactggca    4740
gcagccactg gtaacaggat tagcagagcg aggtatgtag gcggtgctac agagttcttg    4800
aagtggtggc ctaactacgg ctacactaga agaacagtat ttggtatctg cgctctgctg    4860
aagccagtta ccttcggaaa aagagttggt agctcttgat ccggcaaaca aaccaccgct    4920
ggtagcggtg gtttttttgt ttgcaagcag cagattacgc gcagaaaaaa aggatctcaa    4980
gaagatcctt tgatcttttc tacggggtct gacgctcagt ggaacgaaaa ctcacgttaa    5040
gggattttgg tcatgagatt atcaaaaagg atcttcacct agatcctttt aaattaaaaa    5100
tgaagtttta aatcaatcta agtatatat gagtaaactt ggtctgacag ttaccaatgc    5160
ttaatcagtg aggcacctat ctcagcgatc tgtctatttc gttcatccat agttgcctga    5220
ctccccgtcg tgtagataac tacgatacgg gagggcttac catctggccc cagtgctgca    5280
atgataccgc gagaaccacg ctcaccggct ccagatttat cagcaataaa ccagccagcc    5340
ggaagggccg agcgcagaag tggtcctgca actttatccg cctccatcca gtctattaat    5400
tgttgccggg aagctagagt aagtagttcg ccagttaata gtttgcgcaa cgttgttgcc    5460
attgctacag gcatcgtggt gtcacgctcg tcgtttggta tggcttcatt cagctccggt    5520
```

```
tcccaacgat caaggcgagt tacatgatcc cccatgttgt gcaaaaaagc ggttagctcc    5580
ttcggtcctc cgatcgttgt cagaagtaag ttggccgcag tgttatcact catggttatg    5640
gcagcactgc ataattctct tactgtcatg ccatccgtaa gatgcttttc tgtgactggt    5700
gagtactcaa ccaagtcatt ctgagaatag tgtatgcggc gaccgagttg ctcttgcccg    5760
gcgtcaatac gggataatac cgcgccacat agcagaactt taaaagtgct catcattgga    5820
aaacgttctt cggggcgaaa actctcaagg atcttaccgc tgttgagatc cagttcgatg    5880
taacccactc gtgcacccaa ctgatcttca gcatctttta ctttcaccag cgtttctggg    5940
tgagcaaaaa caggaaggca aaatgccgca aaaaagggaa taagggcgac acggaaatgt    6000
tgaatactca tactcttcct ttttcaatat tattgaagca tttatcaggg ttattgtctc    6060
atgagcggat acatatttga atgtatttag aaaaataaac aaataggggt tccgcgcaca    6120
tttccccgaa aagtgccac                                                 6139

<210> SEQ ID NO 36
<211> LENGTH: 57
<212> TYPE: DNA
<213> ORGANISM: Artificial sequence
<220> FEATURE:
<223> OTHER INFORMATION: Leader sequence for 10Fn3 construct

<400> SEQUENCE: 36
atggagtttg ggctgagctg gcttttttctt gtggctattt taaaaggtgt ccagtgt       57

<210> SEQ ID NO 37
<211> LENGTH: 568
<212> TYPE: DNA
<213> ORGANISM: Artificial sequence
<220> FEATURE:
<223> OTHER INFORMATION: Bipartite 10Fn3 construct

<400> SEQUENCE: 37
tccgatgtgc ccagggacct ggaagtggtg gccgccacac ctaccagcct gctgatctct      60
tgggatgccc ctgccgtgac cgtgcggtac tacagaatca cctacggcga gacaggcggc     120
aacagccccg tgcaggagtt tacagtgccc ggcagcaaga gcaccgccac catctctgga     180
ctgaagcccg gcgtggacta caccatcacc gtgtacgccg tgacaggcag aggcgatagc     240
cacagtggta gtactccact gtctgggtgt acaaaaacct ccctgcacgc tctctctaacc    300 tcacaattct gtggcggccg ctttgtagcc agaccctcgg tcaactggat gtcacaactg     360
gcacctgaga ttggaaacat aaaaacaaat attcttacta ttaatcatgt tatcagagaa     420
cttccctgaa gttccagtca gtactgtgac tagctaatta gtcagttact taagcgtcta     480
tccaagtgca aagggacagg aggttttttgt taagggctgt atcactgtgc ctgccagcag    540
caagcccatc agcatcaact accggacc                                        568

<210> SEQ ID NO 38
<211> LENGTH: 1001
<212> TYPE: DNA
<213> ORGANISM: Artificial sequence
<220> FEATURE:
<223> OTHER INFORMATION: Tripartite 10Fn3 construct

<400> SEQUENCE: 38
tccgatgtgc ccagggacct ggaagtggtg gccgccacac ctaccagcct gctgatctct      60
tgggatgccc ctgccgtgac cgtgcggtac tacagaatca cctacggcga gacaggcggc     120
```

```
aacagccccg tgcaggagtt tacagtgccc ggcagcaaga gcaccgccac catctctgga        180
ctgaagcccg gcgtggacta caccatcacc gtgtacgccg tgacaggcca cagtggtagt        240
actccactgt ctgggtgtac aaaaacctcc ctgcacgcct ctctaacctc acaattctgt        300
ggcggccgct ttgtagccag accctcggtc aactggatgt cacaactggc acctgagatt        360
ggaaacataa aaacaaatat tcttactatt aatcatgtta tcagagaact tccctgaagt        420
tccagtcagt actgtgacta gctaattagt cagttactta agcgtctatc caagtgcaaa        480
gggacaggag gttttttgtta agggctgtat cactgtgggc agaggcgaca gccctgccag        540
cagcaagcac agtgatacag cccttaacaa aaaccccctac tgcaacctgg cggtaataga        600
cgtccggaag cacactggct gagtaaattc ctagtgttct ccatccttac ctcggagcca        660
gagtagcagg agccactagc cagcttgggt cttcctatcg cgagtcgtat taatttcgat        720
aagccagcaa gcagtgggtt ctctagttag ccagctgcct cctttctctg ggcccagcgt        780
cctctgtcct ggagctggga gataatgtcc ggggctcct tggtctgcgc tgggcaaagg        840
gtgggcagag tcatgcttgt gctggggaca aaatgacctt gggacacggt cgacgggctg        900
gctgccacgg ccggcccggg acagtcggag agtcaggttt tgtacaccc agacagtgga        960 gtactaccac tgtgaagccc atcagcatca actaccggac c                          1001
```

<210> SEQ ID NO 39
<211> LENGTH: 93
<212> TYPE: PRT
<213> ORGANISM: Artificial sequence
<220> FEATURE:
<223> OTHER INFORMATION: 10Fn3 coding sequence

<400> SEQUENCE: 39

```
Ser Asp Val Pro Arg Asp Leu Glu Val Val Ala Ala Thr Pro Thr Ser
1               5                  10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Arg Gly Asp Ser
65                  70                  75                  80

Pro Ala Ser Ser Lys Pro Ile Ser Ile Asn Tyr Arg Thr
                85                  90
```

<210> SEQ ID NO 40
<211> LENGTH: 7719
<212> TYPE: DNA
<213> ORGANISM: Artificial sequence
<220> FEATURE:
<223> OTHER INFORMATION: Vector E189

<400> SEQUENCE: 40

```
ctaaattgta agcgttaata ttttgttaaa attcgcgtta aattttttgtt aaatcagctc         60 atttttttaac caataggccg aaatcggcaa atcccttat aaatcaaaag aatagaccga        120
gatagggttg agtggccgct acagggcgct cccattcgcc attcaggctg cgcaactgtt        180
gggaagggcg tttcggtgcg ggcctcttcg ctattacgcc agctggcgaa aggggggatgt       240 gctgcaaggc gattaagttg ggtaacgcca gggttttccc agtcacgacg ttgtaaaacg        300
acggccagtg agcgcgacgt aatacgactc actatagggc gaattggcgg aaggccgtca       360
```

```
aggcctaggc gcgcctgaat aacttcgtat agcatacatt atagcaattt atcgaaaaag    420
cctgaactca ccgcgacatc cgtggagaaa ttcctcatcg aaaaattcga ctccgtgtcc    480
gatctcatgc agctgtccga gggcgaggag agtagagcat tctcattcga tgtgggcggg    540
agaggctacg tgctgagagt gaactcttgt gccgacggct tctacaagga ccgatacgtc    600
taccggcatt ttgcttccgc cgctctgcct attccagaag tcctggacat tggggagttt    660
agcgagtccc tcacttactg tattagccgg cgagcccagg gagtgacact ccaggatctg    720
cctgaaactg aactgcctgc tgtgctccag cctgtcgctg aggcaatgga tgctattgct    780
gctgccgatc tgagtcagac tagcggattc ggcccatttg accccaggg cattggccag    840 tacacaacat ggcgagactt catctgtgct atcgccgatc ctcacgtgta ccattggcag    900
actgtgatgg acgatactgt gtctgcttct gtggcacagg cactcgacga actcatgctg    960
tgggctgagg actgtcctga agtgagacat ctggtccatg ccgattttgg ctccaacaat   1020
gtgctcaccg ataacgggag aatcactgcc gtgatcgact ggagcgaggc aatgtttggc   1080
gattcccagt acgaagtggc caacatcttc ttttggcggc cttggctggc ttgtatggaa   1140
cagcagaccc ggtactttga acggcgccac cctgagctgg ctgggagtcc tagactgaga   1200
gcctacatgc tccgaattgg cctggatcag ctctaccagt cactggtgga tggcaatttc   1260
gacgatgctg cttgggcaca ggggcgctgt gatgctattg tccgatccgg cgctggaact   1320
gtggggagaa cacagatcgc taggagatcc gctgctgtct ggaccgatgg atgtgtggaa   1380
gtgctggccg atagtggaaa ccggaggcct tcaacccgac cccgggcaaa ggagtaatga   1440
ccgtttaaac ccgctgatca gcctcgactg tgccttctag ttgccagcca tctgttgttt   1500
gcccctcccc cgtgccttcc ttgacccctgg aaggtgccac tcccactgtc ctttcctaat   1560
aaaatgagga aattgcatcg cattgtctga gtaggtgtca ttctattctg ggggtgggg    1620 tggggcagga cagcaagggg gaggattggg aagacaatag caggcatgct ggggatgcgg   1680
tgggctctat ggggatcccg cgttgacatt gattattgac tagttattaa tagtaatcaa   1740
ttacggggtc attagttcat agcccatata tggagttccg cgttacataa cttacggtaa   1800
atggcccgcc tggctgaccg cccaacgacc cccgcccatt gacgtcaata atgacgtatg   1860
ttcccatagt aacgccaata gggactttcc attgacgtca atgggtggag tatttacggt   1920
aaactgccca cttggcagta catcaagtgt atcatatgcc aagtacgccc cctattgacg   1980
tcaatgacgg taaatggccc gcctggcatt atgcccagta catgacctta tgggactttc   2040
ctacttggca gtacatctac gtattagtca tcgctattac catggtgatg cggttttggc   2100
agtacatcaa tgggcgtgga tagcggtttg actcacgggg atttccaagt ctccacccca   2160
ttgacgtcaa tgggagtttg ttttggcacc aaaatcaacg ggactttcca aaatgtcgta   2220
acaactccgc cccattgacg caaatgggcg gtaggcgtgt acggtgggag gtctatataa   2280
gcagagctct ctggctaact agagaaccca ctgcttactg gcttatcgatc tgatcaagag   2340 acaggataag gagccgccac catggagttt gggctgagct ggctttttct tgtggctatt   2400
ttaaaaggtg tccagtgtta cccatacgat gttccagatt acgcttgcct gccccacagt   2460
ggtagtactc cactgtctgg gtgtacaaaa acctccctgc acgcctctct aacctcacaa   2520
ttctgtggcg gccgcgccgc caccatgatt gaacaagatg gattgcacgc aggttctccg   2580
gccgcttggg tggagaggct attcggctat gactgggcac aacagacaat cggctgctct   2640
gatgccgccg tgttccggct gtcagcgcag gggcgcccgg ttcttttgt caagaccgac   2700
```

```
ctgtccggtg ccctgaatga actgcaggac gaggcagcgc ggctatcgtg gctggccacg    2760
acgggcgttc cttgcgcagc tgtgctcgac gttgtcactg aagcgggaag ggactggctg    2820
ctattgggcg aagtgccggg gcaggatctc ctgtcatctc accttgctcc tgccgagaaa    2880
gtatccatca tggctgatgc aatgcggcgg ctgcatacgc ttgatccggc tacctgccca    2940
ttcgaccacc aagcgaaaca tcgcatcgag cgagcacgta ctcggatgga agccggtctt    3000
gtcgatcagg tgagtacagg aggtggagag tacgcgtaac acttaagcgt ctctccaagt    3060
gcaaagggac aggaggtttt tgttaagggc tgtatcactg tggaccagtt cagatgcggc    3120
aacggccagt gcatcccccT ggattgggtg tgcgacggcg tgaacgactg ccccgattcc    3180
gatgaggaag gctgcccccc tagaacctgt gcccctagcc agcacagtga tacagcccTT    3240
aacaaaaacc cctactgcaa cctggcggta agagacgtcc ggaggccagc ccttctcatg    3300
ttcagagaac atggttaact ggttaagtca tgtcgtccca caggatgatc tggacgaaga    3360
gcatcagggg ctcgcgccag ccgaactgtt cgccaggctc aaggcgcgca tgcccgacgg    3420
cgaggatctc gtcgtgaccc atggcgatgc ctgcttgccg aatatcatgg tggaaaatgg    3480
ccgcttttct ggattcatcg actgtggccg gctgggtgtg gcggaccgct atcaggacat    3540
agcgttggct acccgtgata ttgctgaaga gcttggcggc gaatgggctg accgcttcct    3600
cgtgctttac ggtatcgccg ctcccgattc gcagcgcatc gccttctatc gccttcttga    3660
cgagttcttc tgagtcgact gcaggagtcc cactgcaccc cctcccagt cttctctgtc    3720
caggcaccag gccaggtatc tggggtgtgc agccggcctg ggtctggcct gaggccacaa    3780
gcccggggt ctgtgtggct ggggacaggg acgccggctg cctctgctct gtgcttgggc    3840
catgtgaccc attcgagtgt cctgcacggg cacaggtttt tgtacaccca gacagtggag    3900
tactaccact gtgttccagt gcggctccgg ctactgcatc agccagagat gggtgtgcga    3960
cggggagaat gattgcgagg acggcagcga cgaggccaat tgtgccggct ctgtgcctac    4020
cgagcccaaa tcttgtgaca aaactcacac atgcccaccg tgcccagcac ctgaactcct    4080
gggggaccg tcagtcttcc tcttcccccc aaaacccaag gacaccctca tgatctctag    4140
aaccctgag gtcacatgcg tggtggtgga cgtgagccac gaagaccctg aggtcaagtt    4200
caactggtac gtggacggcg tggaggtgca taatgccaag acaaagccgc gggaggagca    4260
gtacaacagc acgtaccgtg tggtcagcgt cctcaccgtc ctgcaccagg actggctgaa    4320
tggcaaggag tacaagtgca aggtgtccaa caaagccctc ccagccccca tcgagaaaac    4380
catctccaaa gccaaagggc agccccgaga accacaggtg tacaccctgc ccccatcccg    4440
ggatgagctg accaagaacc aggtcagcct gacctgcctg gtcaaaggct tctatcccag    4500
cgacatcgcc gtggagtggg agagcaatgg gcagccggag aacaactaca agaccacgcc    4560
tcccgtgctg gactccgacg gctccttctt cctctacagc aagctcaccg tggacaagtc    4620
taggatgcag caggggaacg tcttctcatg ctccgtgatg catgaggctc tgcacaacca    4680
ctacacgcag aagagcctct ccctgtctcc gggcaaactg gctctcattg tcctgggcgg    4740
cgtggctggc ctgctgctgt ttattgggct gggcatcttc ttttgtgtcc ggtgtcggca    4800
taggaggcgc aaggaggtg gcggatctgg aggggagga tctggagggg gctcaggatc    4860
agggggagga tctggaggcg gatcaactga gtacaaaccc actgtgaggc tcgctactag    4920
agatgatgtg cctagagctg tccgaactct ggctgctgcc ttcgccgatt accctgccac    4980
tcgccatacc gtcgatcccg atcgccacat tgaacgagtac accgaactcc aggagctgtt    5040
tctcactaga gtcgggctgg atattggcaa agtctgggtg gccgatgacg gagccgctgt    5100
```

```
cgctgtgtgg actacacctg agtctgtgga ggctggcgcc gtgtttgctg aaattggacc   5160
tcggatggct gaactgtctg gatctcgact ggctgcccag cagcagatgg agggactgct   5220
ggcaccccat agaccaaagg aacctgcctg gtttctggca actgtgggag tgtcacccga   5280
tcatcagggc aaaggactgg gatctgccgt ggtgctccct ggcgtggagg ccgctgaacg   5340
agctggcgtc cccgcttttc tcgaaacttc tgccccccga aatctcccct tctacgaacg   5400
actgggattc actgtcaccg ccgatgtcga agtgcctgag gggcctagaa catggtgtat   5460
gacccggaaa cccggagctt aaccgtttaa acccgctgat cagcctcgac tgtgccttct   5520
agttgccagc catctgttgt ttgcccctcc ccgtgccttc cttgaccct ggaaggtgcc    5580 actcccactg tcctttccta ataaaatgag gaaattgcat cgcattgtct gagtaggtgt   5640
cattctattc tggggggtgg ggtggggcag gacagcaagg gggaggattg gaagacaat    5700 agcaggcatg ctgggatgc ggtgggctct atggctcgag ttaattaact ggcctcatgg    5760
gccttccgct cactgcccgc tttccagtcg ggaaacctgt cgtgccagct gcattaacat   5820
ggtcatagct gtttccttgc gtattgggcg ctctccgctt cctcgctcac tgactcgctg   5880
cgctcggtcg ttcgggtaaa gctggggtg cctaatgagc aaaaggccag caaaaggcca    5940
ggaaccgtaa aaaggccgcg ttgctggcgt ttttccatag gctccgcccc cctgacgagc   6000
atcacaaaaa tcgacgctca agtcagaggt ggcgaaaccc gacaggacta taaagatacc   6060
aggcgtttcc ccctggaagc tccctcgtgc gctctcctgt tccgaccctg ccgcttaccg   6120
gatacctgtc cgcctttctc ccttcgggaa gcgtggcgct ttctcatagc tcacgctgta   6180
ggtatctcag ttcggtgtag gtcgttcgct ccaagctggg ctgtgtgcac gaaccccccg   6240
ttcagcccga ccgctgcgcc ttatccggta actatcgtct tgagtccaac ccggtaagac   6300
acgacttatc gccactggca gcagccactg gtaacaggat tagcagagcg aggtatgtag   6360
gcggtgctac agagttcttg aagtggtggc ctaactacgg ctacactaga agaacagtat   6420
ttggtatctg cgctctgctg aagccagtta ccttcggaaa aagagttggt agctcttgat   6480
ccggcaaaca aaccaccgct ggtagcggtg gtttttttgt ttgcaagcag cagattacgc   6540
gcagaaaaaa aggatctcaa gaagatcctt tgatctttc tacggggtct gacgctcagt    6600
ggaacgaaaa ctcacgttaa gggattttgg tcatgagatt atcaaaaagg atcttcacct   6660
agatcctttt aaattaaaaa tgaagtttta atcaatcta agtatatat gagtaaactt      6720 ggtctgacag ttaccaatgc ttaatcagtg aggcacctat ctcagcgatc tgtctatttc   6780
gttcatccat agttgcctga ctccccgtcg tgtagataac tacgatacgg gagggcttac   6840
catctggccc cagtgctgca atgataccgc gagaaccacg ctcaccggct ccagatttat   6900
cagcaataaa ccagccagcc ggaagggccg agcgcagaag tggtcctgca actttatccg   6960
cctccatcca gtctattaat tgttgccggg aagctagagt aagtagttcg ccagttaata   7020
gtttgcgcaa cgttgttgcc attgctacag gcatcgtggt gtcacgctcg tcgtttggta   7080
tggcttcatt cagctccggt tcccaacgat caaggcgagt tacatgatcc cccatgttgt   7140
gcaaaaaagc ggttagctcc ttcggtcctc cgatcgttgt cagaagtaag ttggccgcag   7200
tgttatcact catggttatg gcagcactgc ataattctct tactgtcatg ccatccgtaa   7260
gatgcttttc tgtgactggt gagtactcaa ccaagtcatt ctgagaatag tgtatgcggc   7320
gaccgagttg ctcttgcccg gcgtcaatac gggataatac cgcgccacat agcagaactt   7380
taaaagtgct catcattgga aaacgttctt cggggcgaaa actctcaagg atcttaccgc   7440
```

| | |
|---|---|
| tgttgagatc cagttcgatg taacccactc gtgcacccaa ctgatcttca gcatctttta | 7500 |
| ctttcaccag cgtttctggg tgagcaaaaa caggaaggca aaatgccgca aaaaagggaa | 7560 |
| taagggcgac acggaaatgt tgaatactca tactcttcct ttttcaatat tattgaagca | 7620 |
| tttatcaggg ttattgtctc atgagcggat acatatttga atgtatttag aaaaataaac | 7680 |
| aaatagggt tccgcgcaca tttccccgaa aagtgccac | 7719 |

```
<210> SEQ ID NO 41
<211> LENGTH: 1694
<212> TYPE: DNA
<213> ORGANISM: Artificial sequence
<220> FEATURE:
<223> OTHER INFORMATION: Ig Kappa cassette

<400> SEQUENCE: 41
```

| | |
|---|---|
| aattcttctg tctgtcccta acatgccctg tgattatccg caaacaacac acccaagggc | 60 |
| agaactttgt tacttaaaca ccatcctgtt tgcttctttc ctcaggaact gtggctgcac | 120 |
| catctgtctt catcttcccg ccatctgatg agcagttgaa aagcggaaca gccagcgttg | 180 |
| tgtgcctgct gaataacttc tatcccagag aggccaaagt acagtggaag gtggataacg | 240 |
| ccctccaatc gggtaactcc caggagagtg tcacagagca ggacagcaag gacagcacct | 300 |
| acagcctcag cagcaccctg acgctgagca agcagacta cgagaaacac aaagtctacg | 360 |
| cctgcgaagt cacccatcag ggcctgagca gccccgtcac aaagagcttc aacaggggag | 420 |
| agtgtggcgg cggcagctcc cggcaccgcc gagccctggg cggcggcagc gacgtcccgt | 480 |
| caaatattgc aaaaattatc atcggccccc tcatctttgt ctttctcttc tccgttgtga | 540 |
| ttggaagtat ttatctattc ctgagaaaga ggcagccaga tgggccgctg gaccgcttt | 600 |
| acgcttctgg aagcgctatt gaacaagatg gattgcacgc aggttctccg gccgcttggg | 660 |
| tggagaggct attcggctat gactgggcac aacagacaat cggctgctct gatgccgccg | 720 |
| tgttccggct gtcagcgcag gggcgcccgg ttctttttgt caagaccgac ctgtccggtg | 780 |
| ccctgaatga actgcaggac gaggcagcgc ggctatcgtg gctggccacg acgggcgttc | 840 |
| cttgcgcagc tgtgctcgac gttgtcactg aagcgggaag ggactggctg ctattgggcg | 900 |
| aagtgccggg gcaggatctc ctgtcatctc accttgctcc tgccgagaaa gtatccatca | 960 |
| tggctgatgc aatgcggcgg ctgcatacgc ttgatccggc tacctgccca ttcgaccacc | 1020 |
| aagcgaaaca tcgcatcgag cgagcacgta ctcggatgga agccggtctt gtcgatcagg | 1080 |
| atgatctgga cgaagagcat caggggctcg cgccagccga actgttcgcc aggctcaagg | 1140 |
| cgcgcatgcc cgacggcgat gatctcgtcg tgacccatgg cgatgcctgc ttgccgaata | 1200 |
| tcatggtgga aaatggccgc ttttctggat tcatcgactg tggccggctg ggtgtggcgg | 1260 |
| accgctatca ggacatagcg ttggctaccc gtgatattgc tgaagagctt ggcggcgaat | 1320 |
| gggctgaccg cttcctcgtg ctttacggta tcgccgctcc cgattcgcag cgcatcgcct | 1380 |
| tctatcgcct tcttgacgag ttcttctgat ctagagggcc cgtttaaacc cgctgatcag | 1440 |
| cctcgactgt gccttctagt tgccagccat ctgttgtttg cccctccccc gtgccttcct | 1500 |
| tgaccctgga aggtgccact cccactgtcc tttcctaata aaatgaggaa attgcatcgc | 1560 |
| attgtctgag taggtgtcat tctattctgg ggggtggggt gggcaggac agcaagggg | 1620 |
| aggattggga agacaatagc aggcatgctg gggatgcggt gggctctatg gcttctgagg | 1680 |
| cggctgcagt tatg | 1694 |

-continued

```
<210> SEQ ID NO 42
<211> LENGTH: 24
<212> TYPE: PRT
<213> ORGANISM: Artificial sequence
<220> FEATURE:
<223> OTHER INFORMATION: Single A Domain Avimer Variant

<400> SEQUENCE: 42

Asp Tyr Ala Cys Ala Pro Pro Gln Phe Gln Cys Gly Ser Gly Tyr Cys
1               5                   10                  15

Ile Ser Gln Arg Trp Val Cys Asp
            20

<210> SEQ ID NO 43
<211> LENGTH: 20
<212> TYPE: PRT
<213> ORGANISM: Artificial sequence
<220> FEATURE:
<223> OTHER INFORMATION: Single A Domain Avimer Variant

<400> SEQUENCE: 43

Asp Tyr Ala Cys Ala Pro Ser Ser Ser Ser Asp Cys Ile Ser Gln Arg
1               5                   10                  15

Trp Val Cys Asp
            20

<210> SEQ ID NO 44
<211> LENGTH: 25
<212> TYPE: PRT
<213> ORGANISM: Artificial sequence
<220> FEATURE:
<223> OTHER INFORMATION: Single A Domain Avimer Variant

<400> SEQUENCE: 44

Asp Tyr Ala Cys Ala Pro Arg Ser Arg Ser Arg Thr Gly Thr Gly Tyr
1               5                   10                  15

Cys Ile Ser Gln Arg Trp Val Cys Asp
            20                  25

<210> SEQ ID NO 45
<211> LENGTH: 23
<212> TYPE: PRT
<213> ORGANISM: Artificial sequence
<220> FEATURE:
<223> OTHER INFORMATION: Single A Domain Avimer Variant

<400> SEQUENCE: 45

Asp Tyr Ala Cys Ala Pro Ala Ser Ser Ser Ala Ala Pro Ala Cys Ile
1               5                   10                  15

Ser Gln Arg Trp Val Cys Asp
            20

<210> SEQ ID NO 46
<211> LENGTH: 23
<212> TYPE: PRT
<213> ORGANISM: Artificial sequence
<220> FEATURE:
<223> OTHER INFORMATION: Single A Domain Avimer Variant

<400> SEQUENCE: 46

Asp Tyr Ala Cys Ala Pro Arg Phe Gln Cys Gly Ser Gly Ser Cys Ile
1               5                   10                  15

Ser Gln Arg Trp Val Cys Asp
            20
```

```
<210> SEQ ID NO 47
<211> LENGTH: 27
<212> TYPE: PRT
<213> ORGANISM: Artificial sequence
<220> FEATURE:
<223> OTHER INFORMATION: Single A Domain Avimer Variant

<400> SEQUENCE: 47

Asp Tyr Ala Cys Ala Pro Arg Arg Gln Phe Gln Cys Gly Ser Gly Phe
1               5                   10                  15

Pro Tyr Cys Ile Ser Gln Arg Trp Val Cys Asp
            20                  25

<210> SEQ ID NO 48
<211> LENGTH: 25
<212> TYPE: PRT
<213> ORGANISM: Artificial sequence
<220> FEATURE:
<223> OTHER INFORMATION: Single A Domain Avimer Variant

<400> SEQUENCE: 48

Asp Tyr Ala Cys Ala Pro Gln Phe Gln Cys Gly Ser Gly Tyr Asp Tyr
1               5                   10                  15

Cys Ile Ser Gln Arg Trp Val Cys Asp
            20                  25

<210> SEQ ID NO 49
<211> LENGTH: 25
<212> TYPE: PRT
<213> ORGANISM: Artificial sequence
<220> FEATURE:
<223> OTHER INFORMATION: Single A Domain Avimer Variant

<400> SEQUENCE: 49

Asp Tyr Ala Cys Ala Pro Arg Ala Lys Arg Leu Trp Gly Ala Ser Tyr
1               5                   10                  15

Cys Ile Ser Gln Arg Trp Val Cys Asp
            20                  25

<210> SEQ ID NO 50
<211> LENGTH: 26
<212> TYPE: PRT
<213> ORGANISM: Artificial sequence
<220> FEATURE:
<223> OTHER INFORMATION: Single A Domain Avimer Variant

<400> SEQUENCE: 50

Asp Tyr Ala Cys Ala Pro Ser Gln Phe Gln Cys Gly Ser Gly Tyr Gly
1               5                   10                  15

Tyr Cys Ile Ser Gln Arg Trp Val Cys Asp
            20                  25

<210> SEQ ID NO 51
<211> LENGTH: 25
<212> TYPE: PRT
<213> ORGANISM: Artificial sequence
<220> FEATURE:
<223> OTHER INFORMATION: Single A Domain Avimer Variant

<400> SEQUENCE: 51

Asp Tyr Ala Cys Ala Pro Arg Gln Phe Gln Cys Gly Ser Gly Tyr Gly
1               5                   10                  15

Cys Ile Ser Gln Arg Trp Val Cys Asp
            20                  25
```

```
<210> SEQ ID NO 52
<211> LENGTH: 26
<212> TYPE: PRT
<213> ORGANISM: Artificial sequence
<220> FEATURE:
<223> OTHER INFORMATION: Single A Domain Avimer Variant

<400> SEQUENCE: 52

Asp Tyr Ala Cys Ala Leu Gly Gly Ser Ser Ala Ala Pro Ala Glu Gly
1               5                   10                  15

Tyr Cys Ile Ser Gln Arg Trp Val Cys Asp
            20                  25

<210> SEQ ID NO 53
<211> LENGTH: 27
<212> TYPE: PRT
<213> ORGANISM: Artificial sequence
<220> FEATURE:
<223> OTHER INFORMATION: Single A Domain Avimer Variant

<400> SEQUENCE: 53

Asp Tyr Ala Cys Ala Pro Arg Thr Val Pro Val Pro Leu Arg Pro Thr
1               5                   10                  15

Ser Tyr Cys Ile Ser Gln Arg Trp Val Cys Asp
            20                  25

<210> SEQ ID NO 54
<211> LENGTH: 24
<212> TYPE: PRT
<213> ORGANISM: Artificial sequence
<220> FEATURE:
<223> OTHER INFORMATION: Single A Domain Avimer Variant

<400> SEQUENCE: 54

Asp Tyr Ala Cys Ala Pro Ser Gly Asp Ser Gln Phe Gln Cys His Cys
1               5                   10                  15

Ile Ser Gln Arg Trp Val Cys Asp
            20

<210> SEQ ID NO 55
<211> LENGTH: 18
<212> TYPE: PRT
<213> ORGANISM: Artificial sequence
<220> FEATURE:
<223> OTHER INFORMATION: Single A Domain Avimer Variant

<400> SEQUENCE: 55

Asp Tyr Ala Cys Ala Pro Pro Ser Ser Ser Ala Ala Pro Gly Val
1               5                   10                  15

Cys Asp

<210> SEQ ID NO 56
<211> LENGTH: 26
<212> TYPE: PRT
<213> ORGANISM: Artificial sequence
<220> FEATURE:
<223> OTHER INFORMATION: Single A Domain Avimer Variant

<400> SEQUENCE: 56

Asp Tyr Ala Cys Ala Pro Leu Gln Phe Gln Cys Gly Ser Gly Phe Gly
1               5                   10                  15

Tyr Cys Ile Ser Gln Arg Trp Val Cys Asp
            20                  25
```

-continued

<210> SEQ ID NO 57
<211> LENGTH: 24
<212> TYPE: PRT
<213> ORGANISM: Artificial sequence
<220> FEATURE:
<223> OTHER INFORMATION: Single A Domain Avimer Variant

<400> SEQUENCE: 57

Asp Tyr Ala Cys Ala Leu Ala Ser Ser Ser Ala Ala Pro Ala Tyr Cys
1               5                   10                  15

Ile Ser Gln Arg Trp Val Cys Asp
            20

<210> SEQ ID NO 58
<211> LENGTH: 37
<212> TYPE: PRT
<213> ORGANISM: Artificial sequence
<220> FEATURE:
<223> OTHER INFORMATION: A Domain 1 Avimer parent

<400> SEQUENCE: 58

Asp Tyr Ala Cys Leu Pro Asp Gln Phe Arg Cys Gly Asn Gly Gln Cys
1               5                   10                  15

Ile Pro Leu Asp Trp Val Cys Asp Gly Val Asn Asp Cys Pro Asp Ser
            20                  25                  30

Asp Glu Glu Gly Cys
        35

<210> SEQ ID NO 59
<211> LENGTH: 36
<212> TYPE: PRT
<213> ORGANISM: Artificial sequence
<220> FEATURE:
<223> OTHER INFORMATION: A Domain 1 Avimer Variant

<400> SEQUENCE: 59

Asp Tyr Ala Cys Leu Asp Gln Phe Arg Cys Gly Asn Gly Gln Cys Ile
1               5                   10                  15

Pro Leu Asp Trp Val Cys Asp Gly Val Asn Asp Cys Pro Asp Ser Asp
            20                  25                  30

Glu Glu Gly Cys
        35

<210> SEQ ID NO 60
<211> LENGTH: 37
<212> TYPE: PRT
<213> ORGANISM: Artificial sequence
<220> FEATURE:
<223> OTHER INFORMATION: A Domain 1 Avimer Variant

<400> SEQUENCE: 60

Asp Tyr Ala Cys Leu Pro Asp Gln Phe Arg Cys Gly Asn Gly Gln Cys
1               5                   10                  15

Ile Pro Leu Asp Trp Val Cys Asp Gly Val Asn Asp Cys Pro Asp Ser
            20                  25                  30

Asp Glu Glu Gly Cys
        35

<210> SEQ ID NO 61
<211> LENGTH: 37
<212> TYPE: PRT
<213> ORGANISM: Artificial sequence
<220> FEATURE:
<223> OTHER INFORMATION: A Domain 1 Avimer Variant

<400> SEQUENCE: 61

Asp Tyr Ala Cys Leu Pro Gly Gln Phe Arg Cys Gly Asn Gly Gln Cys
1               5                   10                  15

Ile Pro Leu Asp Trp Val Cys Asp Gly Val Asn Asp Cys Pro Asp Ser
            20                  25                  30

Asp Glu Glu Gly Cys
        35

<210> SEQ ID NO 62
<211> LENGTH: 37
<212> TYPE: PRT
<213> ORGANISM: Artificial sequence
<220> FEATURE:
<223> OTHER INFORMATION: A Domain 1 Avimer Variant

<400> SEQUENCE: 62

Asp Tyr Ala Cys Leu Pro Asp Gln Phe Arg Cys Gly Asn Gly Gln Cys
1               5                   10                  15

Ile Pro Leu Asp Trp Val Cys Asp Gly Val Asn Asp Cys Pro Asp Ser
            20                  25                  30

Asp Glu Glu Gly Cys
        35

<210> SEQ ID NO 63
<211> LENGTH: 35
<212> TYPE: PRT
<213> ORGANISM: Artificial sequence
<220> FEATURE:
<223> OTHER INFORMATION: A Domain 1 Avimer Variant

<400> SEQUENCE: 63

Asp Tyr Ala Cys Leu Gln Phe Arg Cys Gly Asn Gly Gln Cys Ile Pro
1               5                   10                  15

Leu Asp Trp Val Cys Asp Gly Val Asn Asp Cys Pro Asp Ser Asp Glu
            20                  25                  30

Glu Gly Cys
        35

<210> SEQ ID NO 64
<211> LENGTH: 36
<212> TYPE: PRT
<213> ORGANISM: Artificial sequence
<220> FEATURE:
<223> OTHER INFORMATION: A Domain 1 Avimer Variant

<400> SEQUENCE: 64

Asp Tyr Ala Cys Leu Asp Gln Phe Arg Cys Gly Asn Gly Gln Cys Ile
1               5                   10                  15

Pro Leu Asp Trp Val Cys Asp Gly Val Asn Asp Cys Pro Asp Ser Asp
            20                  25                  30

Glu Glu Gly Cys
        35

<210> SEQ ID NO 65
<211> LENGTH: 39
<212> TYPE: PRT
<213> ORGANISM: Artificial sequence
<220> FEATURE:
<223> OTHER INFORMATION: A Domain 1 Avimer Variant -continued

<400> SEQUENCE: 65

Asp Tyr Ala Cys Leu Pro Gly Thr Gly Gln Phe Arg Cys Gly Asn Gly
1               5                   10                  15

Gln Cys Ile Pro Leu Asp Trp Val Cys Asp Gly Val Asn Asp Cys Pro
            20                  25                  30

Asp Ser Asp Glu Glu Gly Cys
        35

<210> SEQ ID NO 66
<211> LENGTH: 18
<212> TYPE: PRT
<213> ORGANISM: Artificial sequence
<220> FEATURE:
<223> OTHER INFORMATION: A Domain 2 Avimer parent

<400> SEQUENCE: 66

Pro Pro Arg Thr Cys Ala Pro Ser Gln Phe Gln Cys Gly Ser Gly Tyr
1               5                   10                  15

Cys Ile

<210> SEQ ID NO 67
<211> LENGTH: 18
<212> TYPE: PRT
<213> ORGANISM: Artificial sequence
<220> FEATURE:
<223> OTHER INFORMATION: A Domain 2 Avimer Variant

<400> SEQUENCE: 67

Pro Pro Arg Thr Cys Ala Pro Ser Leu Leu Gln Cys Gly Ser Gly Tyr
1               5                   10                  15

Cys Ile

<210> SEQ ID NO 68
<211> LENGTH: 16
<212> TYPE: PRT
<213> ORGANISM: Artificial sequence
<220> FEATURE:
<223> OTHER INFORMATION: A Domain 2 Avimer Variant

<400> SEQUENCE: 68

Pro Pro Arg Thr Cys Ala Pro Arg Arg Cys Gly Ser Gly Tyr Cys Ile
1               5                   10                  15

<210> SEQ ID NO 69
<211> LENGTH: 18
<212> TYPE: PRT
<213> ORGANISM: Artificial sequence
<220> FEATURE:
<223> OTHER INFORMATION: A Domain 2 Avimer Variant

<400> SEQUENCE: 69

Pro Pro Arg Thr Cys Ala Pro Ser His Phe Gln Cys Gly Ser Gly Tyr
1               5                   10                  15

Cys Ile

<210> SEQ ID NO 70
<211> LENGTH: 20
<212> TYPE: PRT
<213> ORGANISM: Artificial sequence
<220> FEATURE:
<223> OTHER INFORMATION: A Domain 2 Avimer Variant

<400> SEQUENCE: 70

```
Pro Pro Arg Thr Cys Ala Pro Ser Gln Leu Leu Phe Gln Cys Gly Ser
1               5                   10                  15

Gly Tyr Cys Ile
            20

<210> SEQ ID NO 71
<211> LENGTH: 15
<212> TYPE: PRT
<213> ORGANISM: Artificial sequence
<220> FEATURE:
<223> OTHER INFORMATION: A Domain 2 Avimer Variant

<400> SEQUENCE: 71

Pro Pro Arg Thr Cys Ala Pro Gly Cys Gly Ser Gly Tyr Cys Ile
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: A Domain 2 Avimer Variant

<400> SEQUENCE: 72

Pro Pro Arg Thr Cys Glu Phe Gln Cys Gly Ser Gly Tyr Cys Ile
1               5                   10                  15

<210> SEQ ID NO 73
<211> LENGTH: 16
<212> TYPE: PRT
<213> ORGANISM: Artificial sequence
<220> FEATURE:
<223> OTHER INFORMATION: A Domain 2 Avimer Variant

<400> SEQUENCE: 73

Pro Pro Arg Thr Cys Ala Ala Phe Gln Cys Gly Ser Gly Tyr Cys Ile
1               5                   10                  15

<210> SEQ ID NO 74
<211> LENGTH: 12802
<212> TYPE: DNA
<213> ORGANISM: Artificial Sequence
<220> FEATURE:
<223> OTHER INFORMATION: Plasmid ITS001-V655

<400> SEQUENCE: 74
ctaaattgta agcgttaata ttttgttaaa attcgcgtta aattttttgtt aaatcagctc      60 atttttttaac caataggccg aaatcggcaa atcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg     300
acggccagtg agcgcgacgt aatacgactc actatagggc gaattggcgg aaggccgtca     360
aggcctacgc gccgaccgag tccactagtt aactagctga gggccgaggc cgccctgctg     420
cagtgcaccg ccgataccct ggccgacgcc gtgctgatca ccaccgccca cgcttggcag     480
caccagggca agacactgtt catctccaga aagacctacc ggatcgacgg cagcggccag     540
atggccatca cagtggacgt ggaggtggcc tccgacaccc ctcaccccgc cagaatcggc     600
ctgaactgtc agctggccca ggtggccgag agagtgaact ggctgggcct gggccccag      660 gagaactacc ccgaccggct gaccgccgcc tgcttcgaca gatgggacct gcctctgagc     720
```

```
gacatgtaca cccctacgt gttccccagc gagaatggcc tgagatgcgg cacccgggag    780
ctgaactacg gccccacca gtggaggggc gacttccagt tcaacatcag ccggtactcg    840
gatctgaagt tcctattccg aagttcctat tctctagaaa gtataggaac ttcgggccac   900
atggacagag gccggctcgg cccacccctct gccctgagag tgaccgctgt accaacctct  960
gtccctacag ggcagccccg agaaccacag gtgtacaccc tgcctccaag cagggacgaa  1020
ctgacaaaga tcaggtgtc cctcacctgc ctcgtgaagg cttttaccc ctccgatatc    1080
gcagtggaat gggagtccaa cggccagccc gagaataatt acaaaacaac cccccctgtg  1140
ctggacagcg acggcagctt ctttctgtac tccaagctga cagtggataa gtcccgctgg  1200
cagcagggca atgtgttcag ctgctctgtg atgcacgaag ccctccacaa tcattatacc  1260
cagaagtccc tgagcctgag ccccggcaag tgacaattcc aacgccgccc ctctccctcc  1320
ccccccccta acgttactgg ccgaagccgc ttggaataag gccggtgtgc gtttgtctat  1380
atgttatttt ccaccatatt gccgtctttt ggcaatgtga gggcccggaa acctggccct  1440
gtcttcttga cgagcattcc tagggtgtctt tccctctcg ccaaaggaat gcaaggtctg   1500
ttgaatgtcg tgaaggaagc agttcctctg gaagcttctt gaagacaaac aacgtctgta  1560
gcgaccttt gcaggcagcg gaaccccca cctggcgaca ggtgcctctg cggccaaaag    1620
ccacgtgtat aagatacacc tgcaaaggcg gcacaacccc agtgccacgt tgtgagttgg  1680
atagttgtgg aaagagtcaa atggctctcc tcaagcgtat tcaacaaggg gctgaaggat  1740
gcccagaagg tacccattg tatgggatct gatctggggc ctcggtacac atgctttaca   1800
tgtgtttagt cgaggttaaa aaacgtctca ggccccccga accacgggga cgtggttttc  1860
ctttgaaaaa cacgatgata atatggccac aagatctgcc accaccgccg ccaacatgag  1920
cgaaaaatac atcgtcacct gggacatgtt gcagatccat gcacgtaaac tcgcaagccg  1980
actgatgcct tctgaacaat ggaaaggcat tattgccgta agccgtggcg gtctggtacc  2040
gggtgcgtta ctggcgcgtg aactgggtat tcgtcatgtc gataccgttt gtatttccag  2100
ctacgatcac gacaaccagc gcgagcttaa agtgctgaaa cgcgcagaag gcgatggcga  2160
aggcttcatc gttattgatg acctggtgga taccggtggt actgcggttg cgattcgtga  2220
aatgtatcca aaagcgcact tgtcaccat cttcgcaaaa ccggctggtc gtccgctggt  2280
tgatgactat gttgttgata tcccgcaaga tacctggatt gaacagccgt gggatatggg  2340
cgtcgtattc gtcccgccaa tctccggtcg ctaatctttt caacgcctgg cactgccggg  2400
cgttgttctt tttaacttca ggcgggttac aatagtttcc agtaagtatt ctggaggctg  2460
catccatgac acaggcaaac ctgagcgaaa ccctgttcaa accccgcttt aaacatcctg  2520
aaacctcgac gctagtccgc cgctttaatc acggcgcaca accgcctgtg cagtcggccc  2580
ttgatggtaa aaccatccct cactggtatc gcatgattaa ccgtctgatg tggatctggc  2640
gcggcattga cccacgcgaa atcctcgacg tccaggcacg tattgtgatg agcgatgccg  2700
aacgtaccga cgatgattta tacgatacgg tgattggcta ccgtggcggc aactggattt  2760
atgagtgggc cccggatctt tgtgaaggaa ccttacttct gtggtgtgac ataattggac  2820
aaactaccta cagagattta aagctctaag gtaaatataa aattttttaag tgtataatgt  2880
gttaaactac tgattctaat gtttgtgta ttttagattc caacctatgg aactgatgaa   2940
tgggagcagt ggtggaatgc ctttaatgag gaaaacctgt tttgctcaga gaaaatgcca  3000
tctagtgatg atgaggctac tgctgactct caacattcta ctcctccaaa aaagaagaga  3060
aaggtagaag accccaagga cttttccttca gaattgctaa gttttttgag tcatgctgtg  3120
```

```
tttagtaata gaactcttgc ttgctttgct atttacacca caaaggaaaa agctgcactg   3180
ctatacaaga aaattatgga aaaatattct gtaacccttta taagtaggca taacagttat   3240
aatcataaca tactgttttt tcttactcca cacaggcata gagtgtctgc tattaataac   3300
tatgctcaaa aattgtgtac ctttagcttt ttaatttgta aaggggttaa taaggaatat   3360
ttgatgtata gtgccttgac tagagatcat aatcagccat accacatttg tagaggtttt   3420
acttgcttta aaaaacctcc cacacctccc cctgaacctg aaacataaaa tgaatgcaat   3480
tgttgttgtt aacttgttta ttgcagctta taatggttac aaataaagca atagcatcac   3540
aaatttcaca aataaagcat ttttttcact gcattctagt tgtggtttgt ccaaactcat   3600
caatgtatct tatcatgtct gggctagcct cgaagagatt agaatccgag ggcgcgcctg   3660
aataacttcg tatagcatac attatagcaa tttatcgaaa aagcctgaac tcaccgcgac   3720
atccgtggag aaattcctca tcgaaaaatt cgactccgtg tccgatctca tgcagctgtc   3780
cgagggcgag gagagtagag cattctcatt cgatgtgggc gggagaggct acgtgctgag   3840
agtgaactct tgtgccgacg gcttctacaa ggaccgatac gtctaccggc attttgcttc   3900
cgccgctctg cctattccag aagtcctgga cattggggag tttagcgagt ccctcactta   3960
ctgtattagc cggcgagccc agggagtgac actccaggat ctgcctgaaa ctgaactgcc   4020
tgctgtgctc cagcctgtcg ctgaggcaat ggatgctatt gctgctgccg atctgagtca   4080
gactagcgga ttcggcccat tggaccccca gggcattggc cagtacacaa catggcgaga   4140
cttcatctgt gctatcgccg atcctcacgt gtaccattgg cagactgtga tggacgatac   4200
tgtgtctgct tctgtggcac aggcactcga cgaactcatg ctgtgggctg aggactgtcc   4260
tgaagtgaga catctggtcc atgccgattt tggctccaac aatgtgctca ccgataacgg   4320
gagaatcact gccgtgatcg actggagcga ggcaatgttt ggcgattccc agtacgaagt   4380
ggccaacatc ttcttttggc ggccttggct ggcttgtatg gaacagcaga cccggtactt   4440
tgaacggcgc caccctgagc tggctgggag tcctagactg agagcctaca tgctccgaat   4500
tggcctggat cagctctacc agtcactggt ggatggcaat ttcgacgatg ctgcttgggc   4560 acagggcgc tgtgatgcta ttgtccgatc cggcgctgga actgtgggga gaacacagat   4620
cgctaggaga tccgctgctg tctggaccga tggatgtgtg gaagtgctgg ccgatagtgg   4680
aaaccggagg ccttcaaccc gaccccgggc aaaggagtaa tgaccgttta aacccgctga   4740
tcagcctcga ctgtgccttc tagttgccag ccatctgttg tttgcccctc ccccgtgcct   4800
tccttgaccc tggaaggtgc cactcccact gtcctttcct aataaaatga ggaaattgca   4860
tcgcattgtc tgagtaggtg tcattctatt ctggggggtg gggtgggca ggacagcaag   4920 ggggaggatt gggaagacaa tagcaggcat gctgggatg cggtgggctc tatgggatc   4980 ccgcgttgac attgattatt gactagttat taatagtaat caattacggg gtcattagtt   5040
catagcccat atatggagtt ccgcgttaca taacttacgg taaatggccc gcctggctga   5100
ccgcccaacg acccccgccc attgacgtca ataatgacgt atgttcccat agtaacgcca   5160
atagggactt tccattgacg tcaatgggtg gagtatttac ggtaaactgc ccacttggca   5220
gtacatcaag tgtatcatat gccaagtacg ccccctattg acgtcaatga cggtaaatgg   5280
cccgcctggc attatgccca gtacatgacc ttatgggact ttcctacttg gcagtacatc   5340
tacgtattag tcatcgctat taccatggtg atgcggtttt ggcagtacat caatgggcgt   5400
ggatagcggt ttgactcacg gggatttcca agtctccacc ccattgacgt caatgggagt   5460
```

```
ttgttttggc accaaaatca acgggacttt ccaaaatgtc gtaacaactc cgccccattg   5520
acgcaaatgg gcggtaggcg tgtacggtgg gaggtctata taagcagagc tctctggcta   5580
actagagaac ccactgctta ctgctcgacg atctgatcaa gagacaggat aaggagccgc   5640
caccatggac atgagggtcc ccgctcagct cctggggctc ctgctactct ggctccgagg   5700
tgccagatgt gacatccaga tgacccagag ccccagcagc ctgagcgcca gcgtgggcga   5760
cagagtgacc atcacctgtc gggccagcca gtcgatcagc agctacctga actggtatca   5820
gcagaagccc ggcaaggccc ccaagctgct gatctacgcc gccagctccc tgcacagtgg   5880
tagtactcca ctgtctgggt gtacaaaaac ctccctgcac gcctctctaa cctcacaatt   5940
ctgtgacgcg ttcctgaatg cggccgccac ttccggagtg ctggatatca gtcgaccggt   6000
ctgagtgtca cacctactgc gagctcaacc tggcggtaac tgtgacctgg cggtatgtgt   6060
cagacccaga tctcgttact ccaataggtc caagcttggt ttgagaggag aataggattc   6120
atggggaaa tggggaagaa atagctagat ttttctctga acaagcagcc tatctcatat   6180
gattggcttc aagagaggtt tttgtattgg tctgtaccac tgtgtccctg cagagcggcg   6240
tgccaagcag attcagcggc agcggctccg gcaccgactt caccctgacc atcagcagcc   6300
tgcagcccga ggacttcgcc acctactact gccagcagag ttacagtacc cctctcactt   6360
tcggcggagg gaccaaggtg gagatcaaac gtaagtgcac tttcctaatg cttttctta   6420
taaggtttta aatttggagc gttttgtgt ttgagatatt agctcaggtc aattccaaag   6480
agtaccagat gaattcttct gtctgtccct aacatgccct gtgattatcc gcaaacaaca   6540
cacccaaggg cagaactttg ttacttaaac accatcctgt ttgcttcttt cctcaggaac   6600
tgtggctgca ccatctgtct tcatcttccc gccatctgat gagcagttga aagcggaac   6660
agccagcgtt gtgtgcctgc tgaataactt ctatcccaga gaggccaaag tacagtggaa   6720
ggtggataac gccctccaat cgggtaactc ccaggagagt gtcacagagc aggacagcaa   6780
ggacagcacc tacagcctca gcagcaccct gacgctgagc aaagcagact acgagaaaca   6840
caaagtctac gcctgcgaag tcacccatca gggcctgagc agcccgtca caaagagctt   6900
caacagggga gagtgtggcg gcggcagctc cggcaccgc cgagccctgg gcggcggcag   6960
cgacgtcccg tcaaatattg caaaaattat catcggcccc ctcatctttg tctttctctt   7020
ctccgttgtg attggaagta tttatctatt cctgagaaag aggcagccag atgggccgct   7080
gggaccgctt tacgcttctg gaagcgctat tgaacaagat ggattgcacg caggttctcc   7140
ggccgcttgg gtggagaggc tattcggcta tgactgggca caacagacaa tcggctgctc   7200
tgatgccgcc gtgttccggc tgtcagcgca ggggcgcccg gttctttttg tcaagaccga   7260
cctgtccggt gccctgaatg aactgcagga cgaggcagcg cggctatcgt ggctggccac   7320
gacgggcgtt ccttgcgcag ctgtgctcga cgttgtcact gaagcgggaa gggactggct   7380
gctattgggc gaagtgccgg ggcaggatct cctgtcatct caccttgctc ctgccgagaa   7440
agtatccatc atggctgatg caatgcggcg gctgcatacg cttgatccgg ctacctgccc   7500
attcgaccac caagcgaaac atcgcatcga gcgagcacgt actcggatgg aagccggtct   7560
tgtcgatcag gatgatctgg acgaggagca tcagggctc gcgccagccg aactgttcgc   7620
caggctcaag gcgcgcatgc ccgacggcga tgatctcgtc gtgacccatg gcgatgcctg   7680
cttgccgaat atcatggtgg aaaatggccg cttttctgga ttcatcgact gtggccggct   7740
gggtgtggcg gaccgctatc aggacatagc gttggctacc cgtgatattg ctgaggagct   7800
tggcggcgaa tgggctgacc gcttcctcgt gctttacggt atcgccgctc ccgattcgca   7860
```

```
gcgcatcgcc ttctatcgcc ttcttgacga gttcttctga tctagagggc ccgtttaaac   7920
ccgctgatca gcctcgactg tgccttctag ttgccagcca tctgttgttt gcccctcccc   7980
cgtgccttcc ttgaccctgg aaggtgccac tcccactgtc ctttcctaat aaaatgagga   8040
aattgcatcg cattgtctga gtaggtgtca ttctattctg gggggtgggg tggggcagga   8100
cagcaagggg gaggattggg aagacaatag caggcatgct ggggatgcgg tgggctctat   8160
ggcttctgag gcggctgcag ttatgtcgac cgcgttgaca ttgattattg actagttatt   8220
aatagtaatc aattacgggg tcattagttc atagcccata tatggagttc cgcgttacat   8280
aacttacggt aaatggcccg cctggctgac cgcccaacga cccccgccca ttgacgtcaa   8340
taatgacgta tgttcccata gtaacgccaa tagggacttt ccattgacgt caatgggtgg   8400
agtatttacg gtaaactgcc cacttggcag tacatcaagt gtatcatatg ccaagtacgc   8460
cccctattga cgtcaatgac ggtaaatggc ccgcctggca ttatgcccag tacatgacct   8520
tatgggactt tcctacttgg cagtacatct acgtattagt catcgctatt accatggtga   8580
tgcggttttg gcagtacatc aatgggcgtg atagcggttt gactcacggg gatttccaa   8640 gtctccaccc cattgacgtc aatgggagtt tgttttggca ccaaaatcaa cgggactttc   8700
caaaatgtcg taacaactcc gccccattga cgcaaatggg cggtaggcgt gtacggtggg   8760
aggtctatat aagcagagct ctctggctaa ctagagaacc cactgcttac tggcttatcg   8820
aaattaatac gactcactat agggagacac aagctggcgg ccgctaataa aggcgatctg   8880
atcaagagac aggataagga ccgccacca tggagtttgg gctgagctgg cttttcttg   8940 tggctatttt aaaaggtgtc cagtgtcagg tgcagctggt gcagtctggc gccgaagtga   9000
agaaacctgg cgcctccgtg aaggtgtcct gcaaggccag cggctacacc ttcaccagct   9060
acggcatcag ctgggtccgc caggctcctg gacagggact ggaatggatg ggctggatca   9120
gcgcctacaa cggcaacacc aactacgccc agaaactgca gggcagagtg accatgacca   9180
ccgacaccag caccagcacc gcctacatgg aacttcgaag cctgagaagc gacgacaccg   9240
ccgtgtatta ctgtgcgaga gagctagcct atgatgcttt tgatatctgg ggccaaggga   9300
caatggtcac cgtgtcctca gcctccacca agggcccatc ggtcttcccc ctggcaccct   9360
cctccaagag cacctctggg ggcacagcgg ccctgggctg cctggtcaag gactacttcc   9420
ccgaaccggt gacggtgtcg tggaactcag gcgccctgac cagcggcgtg cataccttcc   9480
cggctgtcct acagtcctca ggactctact ccctcagcag cgtggtgacc gtgccctcca   9540
gcagcttggg cacccagacc tacatctgca acgtgaatca caagcccagc aacaccaagg   9600
tggacaagaa agttgagccc aaatcttgtg acaaaactca cacatgccca ccgtgcccag   9660
cacctgaact cctgggggga ccgtcagtct tcctcttccc cccaaaaccc aaggacaccc   9720
tcatgatctc tagaacccct gaggtcacat gcgtggtggt ggacgtgagc cacgaagacc   9780
ctgaggtcaa gttcaactgg tacgtggacg gcgtggaggt gcataatgcc aagacaaagc   9840
cgcgggagga gcagtacaac agcacgtacc gtgtggtcag cgtcctcacc gtcctgcacc   9900
aggactggct gaatggcaag gagtacaagt gcaaggtgtc caacaaagcc ctcccagccc   9960
ccatcgagaa aaccatctcc aaagccaaag gtgggacccg tggggtgcga atagaagttc  10020
ctattccgaa gttcctattc tctagaaagt ataggaactt cgggccacat ggaattaatt  10080
cagaggccgg ctcggcccac cctctgccct gagagtgacc gctgtaccaa cctctgtccc  10140
tacagggcag ccccgagaac cacaggtgta caccctgccc ccatcccggg atgagctgac  10200
```

```
caagaaccag gtcagcctga cctgcctggt caaaggcttc tatcccagcg acatcgccgt    10260
ggagtgggag agcaatgggc agccggagaa caactacaag accacgcctc ccgtgctgga    10320
ctccgacggc tccttcttcc tctacagcaa gctcaccgtg gacaagagca ggtggcagca    10380
ggggaacgtc ttctcatgct ccgtgatgca tgaggctctg cacaaccact acacgcagaa    10440
gaacctctcc ctgtctccgg gcaaagctgt gggccaggac acgcaggagg tcatcgtggt    10500
gccacactcc ttgcccttta aggtggtggt gatctcagcc atcctggccc tggtggtgct    10560
caccatcatc tcccttatca tcctcatcat gctttggcag aagaagccac gttaggtttt    10620 ccggacgcc ggctggatga tcctccagcg cggggatctc atgctggagt tcttcgccca    10680
ccccaacttg tttattgcag cttataatgg ttacaaataa agcaatagca tcacaaattt    10740
cacaaataaa gcattttttt cactgcattc tagttgtggt ttgtccaaac tcatcaatgt    10800
atcttatcat gtctgacctc gagttaatta actggcctca tgggccttcc gctcactgcc    10860
cgctttccag tcgggaaacc tgtcgtgcca gctgcattaa catggtcata gctgtttcct    10920
tgcgtattgg gcgctctccg cttcctcgct cactgactcg ctgcgctcgg tcgttcgggt    10980 aaagctggg gtgcctaatg agcaaaaggc cagcaaaagg ccaggaaccg taaaaaggcc    11040
gcgttgctgg cgttttttcca taggctccgc cccctgacg agcatcacaa aaatcgacgc    11100
tcaagtcaga ggtggcgaaa cccgacagga ctataaagat accaggcgtt tccccctgga    11160
agctccctcg tgcgctctcc tgttccgacc ctgccgctta ccggatacct gtccgccttt    11220
ctcccttcgg gaagcgtggc gctttctcat agctcacgct gtaggtatct cagttcggtg    11280
taggtcgttc gctccaagct gggctgtgtg cacgaacccc ccgttcagcc cgaccgctgc    11340
gccttatccg gtaactatcg tcttgagtcc aacccggtaa gacacgactt atcgccactg    11400
gcagcagcca ctggtaacag gattagcaga gcgaggtatg taggcggtgc tacagagttc    11460
ttgaagtggt ggcctaacta cggctacact agaagaacag tatttggtat ctgcgctctg    11520
ctgaagccag ttaccttcgg aaaaagagtt ggtagctctt gatccggcaa acaaaccacc    11580
gctggtagcg gtggtttttt tgtttgcaag cagcagatta cgcgcagaaa aaaggatct    11640 caagaagatc ctttgatctt ttctacgggg tctgacgctc agtggaacga aaactcacgt    11700
taagggattt tggtcatgag attatcaaaa aggatcttca cctagatcct tttaaattaa    11760
aaatgaagtt ttaaatcaat ctaaagtata tatgagtaaa cttggtctga cagttaccaa    11820
tgcttaatca gtgaggcacc tatctcagcg atctgtctat ttcgttcatc catagttgcc    11880
tgactccccg tcgtgtagat aactacgata cgggagggct taccatctgg ccccagtgct    11940
gcaatgatac cgcgagaacc acgctcaccg gctccagatt tatcagcaat aaaccagcca    12000
gccggaaggg ccgagcgcag aagtggtcct gcaactttat ccgcctccat ccagtctatt    12060
aattgttgcc gggaagctag agtaagtagt tcgccagtta atagtttgcg caacgttgtt    12120
gccattgcta caggcatcgt ggtgtcacgc tcgtcgtttg gtatggcttc attcagctcc    12180
ggttcccaac gatcaaggcg agttacatga tcccccatgt tgtgcaaaaa agcggttagc    12240
tccttcggtc ctccgatcgt tgtcagaagt aagttggccg cagtgttatc actcatggtt    12300
atggcagcac tgcataattc tcttactgtc atgccatccg taagatgctt ttctgtgact    12360
ggtgagtact caaccaagtc attctgagaa tagtgtatgc ggcgaccgag ttgctcttgc    12420
ccggcgtcaa tacgggataa taccgcgcca catagcagaa ctttaaaagt gctcatcatt    12480
ggaaaacgtt cttcggggcg aaaactctca aggatcttac cgctgttgag atccagttcg    12540
atgtaaccca ctcgtgcacc caactgatct tcagcatctt ttactttcac cagcgtttct    12600
```

```
gggtgagcaa aaacaggaag gcaaaatgcc gcaaaaaagg gaataagggc gacacggaaa    12660
tgttgaatac tcatactctt cctttttcaa tattattgaa gcatttatca gggttattgt    12720
ctcatgagcg gatacatatt tgaatgtatt tagaaaaata aacaaatagg ggttccgcgc    12780
acatttcccc gaaaagtgcc ac                                             12802
```

```
<210> SEQ ID NO 75
<211> LENGTH: 8
<212> TYPE: PRT
<213> ORGANISM: Artificial Sequence
<220> FEATURE:
<223> OTHER INFORMATION: Light Chain CDR2 Sequence

<400> SEQUENCE: 75

Tyr Ala Ala Ser Ser Leu Gln Ser
1               5

<210> SEQ ID NO 76
<211> LENGTH: 8
<212> TYPE: PRT
<213> ORGANISM: Artificial Sequence
<220> FEATURE:
<223> OTHER INFORMATION: Variant Light Chain CDR2 Sequence

<400> SEQUENCE: 76

Phe Val Ala Ser Thr Leu Gln Ser
1               5

<210> SEQ ID NO 77
<211> LENGTH: 10
<212> TYPE: PRT
<213> ORGANISM: Artificial Sequence
<220> FEATURE:
<223> OTHER INFORMATION: Variant Light Chain CDR2 Sequence

<400> SEQUENCE: 77

Tyr Ala Ala Ser Ser Leu Gln Gly Leu Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Variant Light Chain CDR2 Sequence

<400> SEQUENCE: 78

Tyr Ala Ala Ser Ser Leu Pro Pro Ser Leu Gln Ser
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Variant Light Chain CDR2 Sequence

<400> SEQUENCE: 79

Phe Val Ala Ser Arg Leu Gln Ser
1               5

<210> SEQ ID NO 80
<211> LENGTH: 13
<212> TYPE: PRT
<213> ORGANISM: Artificial Sequence
```

```
<220> FEATURE:
<223> OTHER INFORMATION: Variant Light Chain CDR2 Sequence

<400> SEQUENCE: 80

Tyr Ala Ala Ser Ser Gln Ala Gly Leu Ser Leu Gln Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Light Chain CDR1 Sequence

<400> SEQUENCE: 81

Arg Ala Ser Gln Ser Ile Ser Ser Tyr Leu Asn
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Variant Light Chain CDR1 Sequence

<400> SEQUENCE: 82

Arg His Ser Gln Arg Lys Ser Asp Val Ser Gly Tyr Ala Asn
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Variant Light Chain CDR1 Sequence

<400> SEQUENCE: 83

Arg His Ser Gln Arg Lys Trp Asp Val Ser Gly Tyr Ala Asn
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Variant Light Chain CDR1 Sequence

<400> SEQUENCE: 84

Arg Ala Pro Gln Pro Tyr Ile Arg Gly Tyr Leu Asn
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Variant Light Chain CDR1 Sequence

<400> SEQUENCE: 85

Arg His Ser Gln Arg Lys Phe Asp Val Ser Gly Tyr Ala Asn
1               5                   10

<210> SEQ ID NO 86
<211> LENGTH: 27
<212> TYPE: DNA
<213> ORGANISM: Artificial Sequence
<220> FEATURE:
```

<223> OTHER INFORMATION: Cassette for Generating Avimer Sequence
      Diversity

<400> SEQUENCE: 86
agccagttcc agtgcggctc cggctac                                          27

<210> SEQ ID NO 87
<211> LENGTH: 9
<212> TYPE: PRT
<213> ORGANISM: Artificial Sequence
<220> FEATURE:
<223> OTHER INFORMATION: Cassette for Generating Avimer Sequence
      Diversity

<400> SEQUENCE: 87

Ser Gln Phe Gln Cys Gly Ser Gly Tyr
1               5

<210> SEQ ID NO 88
<211> LENGTH: 33
<212> TYPE: DNA
<213> ORGANISM: Artificial Sequence
<220> FEATURE:
<223> OTHER INFORMATION: Cassette for Generating Avimer Sequence
      Diversity

<400> SEQUENCE: 88
tacagccagt ttgtgtgcgg ctccggctac tac                                   33

<210> SEQ ID NO 89
<211> LENGTH: 10
<212> TYPE: PRT
<213> ORGANISM: Artificial Sequence
<220> FEATURE:
<223> OTHER INFORMATION: Cassette for Generating Avimer Sequence
      Diversity

<400> SEQUENCE: 89

Gln Pro Val Cys Val Arg Leu Arg Leu Leu
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Cassette for Generating Avimer Sequence
      Diversity

<400> SEQUENCE: 90

Thr Ala Ser Leu Cys Ala Ala Pro Ala Thr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Cassette for Generating Avimer Sequence
      Diversity

<400> SEQUENCE: 91

Tyr Ser Gln Phe Val Cys Gly Ser Gly Tyr Tyr
1               5                   10

<210> SEQ ID NO 92
<211> LENGTH: 279

<212> TYPE: DNA
<213> ORGANISM: Artificial Sequence
<220> FEATURE:
<223> OTHER INFORMATION: Fn10

<400> SEQUENCE: 92

```
tccgatgtgc ccagggacct ggaagtggtg gccgccacac ctaccagcct gctgatctct      60
tgggatgccc ctgccgtgac cgtgcggtac tacagaatca cctacggcga gacaggcggc     120
aacagccccg tgcaggagtt tacagtgccc ggcagcaaga gcaccgccac catctctgga     180
ctgaagcccg gcgtggacta caccatcacc gtgtacgccg tgacaggcag aggcgacagc     240
cctgccagca gcaagcccat cagcatcaac taccggacc                            279
```

<210> SEQ ID NO 93
<211> LENGTH: 93
<212> TYPE: PRT
<213> ORGANISM: Artificial Sequence
<220> FEATURE:
<223> OTHER INFORMATION: Fn10

<400> SEQUENCE: 93

```
Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Arg Gly Asp Ser
65                  70                  75                  80

Pro Ala Ser Ser Lys Pro Ile Ser Ile Asn Tyr Arg Thr
                85                  90
```

<210> SEQ ID NO 94
<211> LENGTH: 63
<212> TYPE: DNA
<213> ORGANISM: Artificial Sequence
<220> FEATURE:
<223> OTHER INFORMATION: 23bp RSS region of a bipartite 10Fn3 construct

<400> SEQUENCE: 94

```
acaggcagag gcgatagcca cagtggtagt actccactgt ctgggtgtac aaaaacctcc      60
ctg                                                                    63
```

<210> SEQ ID NO 95
<211> LENGTH: 61
<212> TYPE: DNA
<213> ORGANISM: Artificial Sequence
<220> FEATURE:
<223> OTHER INFORMATION: 12bp RSS region of a bipartite 10Fn3 construct

<400> SEQUENCE: 95

```
gacaggaggt ttttgttaag ggctgtatca ctgtgcctgc cagcagcaag cccatcagca      60
t                                                                      61
```

<210> SEQ ID NO 96
<211> LENGTH: 61
<212> TYPE: DNA
<213> ORGANISM: Artificial Sequence
<220> FEATURE:

-continued

<223> OTHER INFORMATION: 23bp RSS region of a tripartite 10Fn3 construct

<400> SEQUENCE: 96
gtgtacgccg tgacaggcca cagtggtagt actccactgt ctgggtgtac aaaaacctcc    60
c                                                                    61

<210> SEQ ID NO 97
<211> LENGTH: 91
<212> TYPE: DNA
<213> ORGANISM: Artificial Sequence
<220> FEATURE:
<223> OTHER INFORMATION: 12bp RSS regions of a tripartite 10Fn3
      construct

<400> SEQUENCE: 97
ggaggttttt gttaagggct gtatcactgt gggcagaggc gacagccctg ccagcagcaa    60
gcacagtgat acagccctta acaaaaaccc c                                   91

<210> SEQ ID NO 98
<211> LENGTH: 10
<212> TYPE: PRT
<213> ORGANISM: Artificial Sequence
<220> FEATURE:
<223> OTHER INFORMATION: 10Fn3 FG loop

<400> SEQUENCE: 98

Ala Glu Ala Thr Ala Leu Pro Ala Ala Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: 10Fn3 FG loop

<400> SEQUENCE: 99

Gly Arg Gly Asp Ser Pro Ala Ser Ser Lys
1               5                   10

<210> SEQ ID NO 100
<211> LENGTH: 10
<212> TYPE: PRT
<213> ORGANISM: Artificial Sequence
<220> FEATURE:
<223> OTHER INFORMATION: 10Fn3 FG loop

<400> SEQUENCE: 100

Gln Arg Arg Gln Pro Cys Gln Gln Gln Ala
1               5                   10

<210> SEQ ID NO 101
<211> LENGTH: 62
<212> TYPE: DNA
<213> ORGANISM: Artificial Sequence
<220> FEATURE:
<223> OTHER INFORMATION: 23bp RSS region of a tripartite 10Fn3 construct

<400> SEQUENCE: 101
ggagagtcag gttttttgtac acccagacag tggagtacta ccactgtgaa gcccatcagc    60
at                                                                   62

<210> SEQ ID NO 102
<211> LENGTH: 37

```
<212> TYPE: DNA
<213> ORGANISM: Artificial Sequence
<220> FEATURE:
<223> OTHER INFORMATION: 5'/3' junction for CDR1 RSS placement

<400> SEQUENCE: 102
gctacacctt caccagctac gccatgaact gggtccg                              37

<210> SEQ ID NO 103
<211> LENGTH: 43
<212> TYPE: DNA
<213> ORGANISM: Artificial Sequence
<220> FEATURE:
<223> OTHER INFORMATION: 5'/3' junction for CDR2 RSS placement

<400> SEQUENCE: 103
ggatcaacac caacaccggc aaccccacct acgcccaggg ctt                       43

<210> SEQ ID NO 104
<211> LENGTH: 61
<212> TYPE: DNA
<213> ORGANISM: Artificial Sequence
<220> FEATURE:
<223> OTHER INFORMATION: 23bp RSS region of heavy chain CDR2 construct

<400> SEQUENCE: 104
tgggctggat caacaccaac cacagtggta gtactccact gtctgggtgt acaaaaacct     60
c                                                                    61

<210> SEQ ID NO 105
<211> LENGTH: 46
<212> TYPE: DNA
<213> ORGANISM: Artificial Sequence
<220> FEATURE:
<223> OTHER INFORMATION: 12bp RSS region of heavy chain CDR2 construct

<400> SEQUENCE: 105
aggtttttgt taagggctgt atcactgtga ccggcaaccc caccta                    46

<210> SEQ ID NO 106
<211> LENGTH: 70
<212> TYPE: DNA
<213> ORGANISM: Artificial Sequence
<220> FEATURE:
<223> OTHER INFORMATION: 23bp RSS region at heavy chain CDR1 5' junction

<400> SEQUENCE: 106
agcggctaca ccttcaccag ccacagtggt agtactccac tgtctgggtg tacaaaaacc     60
tccctgcacg                                                           70

<210> SEQ ID NO 107
<211> LENGTH: 56
<212> TYPE: DNA
<213> ORGANISM: Artificial Sequence
<220> FEATURE:
<223> OTHER INFORMATION: 12bp RSS region at heavy chain CDR1 3' junction

<400> SEQUENCE: 107 gaggttttg ttaagggctg tatcactgtg agctacgcca tgaactgggt ccgcca          56

<210> SEQ ID NO 108
<211> LENGTH: 56
<212> TYPE: DNA
<213> ORGANISM: Artificial Sequence
```

```
<220> FEATURE:
<223> OTHER INFORMATION: 12bp RSS region at heavy chain CDR2 5' junction

<400> SEQUENCE: 108
ggctggatca acaccaacac ccacagtgat acagcccta acaaaaaccc ctactg        56

<210> SEQ ID NO 109
<211> LENGTH: 70
<212> TYPE: DNA
<213> ORGANISM: Artificial Sequence
<220> FEATURE:
<223> OTHER INFORMATION: 12bp RSS region at heavy chain CDR2 3' junction

<400> SEQUENCE: 109
tcaggttttt gtacacccag acagtggagt actaccactg tgaccggcaa ccccacctac   60
gcccagggct                                                         70

<210> SEQ ID NO 110
<211> LENGTH: 63
<212> TYPE: DNA
<213> ORGANISM: Artificial Sequence
<220> FEATURE:
<223> OTHER INFORMATION: antisense strand of SEQ ID NO: 94

<400> SEQUENCE: 110
cagggaggtt tttgtacacc cagacagtgg agtactacca ctgtggctat cgcctctgcc   60
tgt                                                                63

<210> SEQ ID NO 111
<211> LENGTH: 61
<212> TYPE: DNA
<213> ORGANISM: Artificial Sequence
<220> FEATURE:
<223> OTHER INFORMATION: antisense strand of SEQ ID NO: 95

<400> SEQUENCE: 111
atgctgatgg gcttgctgct ggcaggcaca gtgatacagc ccttaacaaa aacctcctgt   60
c                                                                  61

<210> SEQ ID NO 112
<211> LENGTH: 61
<212> TYPE: DNA
<213> ORGANISM: Artificial Sequence
<220> FEATURE:
<223> OTHER INFORMATION: antisense strand of SEQ ID NO: 96

<400> SEQUENCE: 112
gggaggtttt tgtacaccca gacagtggag tactaccact gtggcctgtc acggcgtaca   60
c                                                                  61

<210> SEQ ID NO 113
<211> LENGTH: 91
<212> TYPE: DNA
<213> ORGANISM: Artificial Sequence
<220> FEATURE:
<223> OTHER INFORMATION: antisense strand of SEQ ID NO: 97

<400> SEQUENCE: 113 ggggttttg ttaagggctg tatcactgtg cttgctgctg gcagggctgt cgcctctgcc    60
cacagtgata cagcccttaa caaaaacctc c                                  91
```

<210> SEQ ID NO 114
<211> LENGTH: 62
<212> TYPE: DNA
<213> ORGANISM: Artificial Sequence
<220> FEATURE:
<223> OTHER INFORMATION: antisense strand of SEQ ID NO: 101

<400> SEQUENCE: 114
atgctgatgg gcttcacagt ggtagtactc cactgtctgg gtgtacaaaa acctgactct    60
cc                                                                  62

<210> SEQ ID NO 115
<211> LENGTH: 37
<212> TYPE: DNA
<213> ORGANISM: Artificial Sequence
<220> FEATURE:
<223> OTHER INFORMATION: antisense strand of SEQ ID NO: 102

<400> SEQUENCE: 115
cggacccagt tcatggcgta gctggtgaag gtgtagc                             37

<210> SEQ ID NO 116
<211> LENGTH: 43
<212> TYPE: DNA
<213> ORGANISM: Artificial Sequence
<220> FEATURE:
<223> OTHER INFORMATION: antisense strand of SEQ ID NO: 103

<400> SEQUENCE: 116
aagccctggg cgtaggtggg gttgccggtg ttggtgttga tcc                      43

<210> SEQ ID NO 117
<211> LENGTH: 61
<212> TYPE: DNA
<213> ORGANISM: Artificial Sequence
<220> FEATURE:
<223> OTHER INFORMATION: antisense strand of SEQ ID NO: 104

<400> SEQUENCE: 117 gaggttttg tacacccaga cagtggagta ctaccactgt ggttggtgtt gatccagccc    60
a                                                                   61

<210> SEQ ID NO 118
<211> LENGTH: 46
<212> TYPE: DNA
<213> ORGANISM: Artificial Sequence
<220> FEATURE:
<223> OTHER INFORMATION: antisense strand of SEQ ID NO: 105

<400> SEQUENCE: 118
taggtggggt tgccggtcac agtgatacag cccttaacaa aaacct                   46

<210> SEQ ID NO 119
<211> LENGTH: 70
<212> TYPE: DNA
<213> ORGANISM: Artificial Sequence
<220> FEATURE:
<223> OTHER INFORMATION: antisense strand of SEQ ID NO: 106

<400> SEQUENCE: 119
cgtgcaggga ggttttttgta cacccagaca gtggagtact accactgtgg ctggtgaagg    60
tgtagccgct                                                            70

```
<210> SEQ ID NO 120
<211> LENGTH: 56
<212> TYPE: DNA
<213> ORGANISM: Artificial Sequence
<220> FEATURE:
<223> OTHER INFORMATION: antisense strand of SEQ ID NO: 107

<400> SEQUENCE: 120
tggcggaccc agttcatggc gtagctcaca gtgatacagc ccttaacaaa aacctc         56

<210> SEQ ID NO 121
<211> LENGTH: 56
<212> TYPE: DNA
<213> ORGANISM: Artificial Sequence
<220> FEATURE:
<223> OTHER INFORMATION: antisense strand of SEQ ID NO: 108

<400> SEQUENCE: 121
cagtaggggt ttttgttaag ggctgtatca ctgtgggtgt tggtgttgat ccagcc         56

<210> SEQ ID NO 122
<211> LENGTH: 70
<212> TYPE: DNA
<213> ORGANISM: Artificial Sequence
<220> FEATURE:
<223> OTHER INFORMATION: antisense strand of SEQ ID NO: 109

<400> SEQUENCE: 122
agccctgggc gtaggtgggg ttgccggtca cagtggtagt actccactgt ctgggtgtac    60
aaaaacctga                                                           70
```

GENERATING TARGETED SEQUENCE DIVERSITY IN PROTEINS

CROSS-REFERENCE TO RELATED APPLICATIONS

This is the U.S. National Stage of International Application No. PCT/CA2013/050203, filed Mar. 14, 2013, which claims the benefit of U.S. Provisional Patent Application No. 61/610,774, filed Mar. 14, 2012, the disclosures of which are hereby incorporated by reference in their entireties.

INCORPORATION OF SEQUENCE LISTING

A sequence listing contained in the file named "Sequence_listing_ST25_PCT_CA2013_050203.txt" which is 89,547 bytes (measured in MS-Windows) and comprising 109 nucleotide sequences, created on Sep. 11, 2014, is electronically filed herewith and is incorporated by reference in its entirety.

FIELD OF THE INVENTION

The present invention relates to the field of protein mutagenesis and, in particular, to methods and compositions for targeted protein mutagenesis.

BACKGROUND OF THE INVENTION

Protein function can be modified and improved in vitro by a variety of methods, including site-directed mutagenesis, combinatorial cloning and random mutagenesis combined with an appropriate selection system.

The method of random mutagenesis together with selection has been used in a number of cases to improve protein function and generally follows one of two strategies. The first involves randomisation of the entire gene sequence in combination with the selection of a variant (mutant) protein with desired characteristics. This process can be repeated on the selected variant until a protein variant is found which is considered optimal. Mutations are typically introduced by error-prone PCR (Leung et al., 1989, *Technique*, 1:11-15) with a mutation rate of approximately 0.7%. The second strategy is to mutagenize defined regions of the gene with degenerate primers ("saturation mutagenesis"), which allows for mutation rates of up to 100% (Griffiths et al., 1994, *EMBO. J*, 13:3245-3260; Yang et al., 1995, *J. Mol. Biol.* 254:392-403), followed by selection of variants with interesting characteristics. The mutated DNA regions from different variants, each with interesting characteristics, may subsequently be combined into one coding sequence (Yang et al., ibid).

Another process for in vitro mutation of protein function is "DNA shuffling," which uses random fragmentation of DNA and assembly of fragments into a functional coding sequence (Stemmer, 1994, *Nature* 370:389-391). The DNA shuffling process generates diversity by recombination, combining useful mutations from individual genes. The genes are randomly fragmented using DNase I and then reassembled by recombination with each other. The starting material can be either a single gene (first randomly mutated using error-prone PCR) or naturally occurring homologous sequences (so-called family shuffling).

V(D)J recombination is the process responsible for the assembly of antibody gene segments (V, D and J; or V and J in the case of the light chain) and as part of the assembly process creates the CDR3 of the respective antibody chain. V(D)J recombination can be considered conceptually as a segment shuffler for antibodies, i.e. it brings together the different VH segments, D segments and JH segments to create an antibody (similarly V(D)J recombination at the light chain assembles different combinations of light chain V and J segments at either the kappa or lambda locus). The recombination event results in large chromosomal deletions in order to bring the required segments together. V(D)J recombination is targeted by the presence of specific DNA sequences called the recombination signal sequences (RSSs). The recombination reaction involves the recombination proteins RAG-1 and RAG-2 and follows a 12/23 rule where an RSS with a 23 bp spacer is paired only with an RSS with 12 bp spacer and adjacent sequences are subsequently joined by double-stranded break repair proteins.

The V(D)J recombination reaction is responsible for the creation of CDR3, as it is the sole mechanism for gene segment assembly and antibody generation in the bone marrow. V(D)J recombination does not occur at CDR1 or CDR2. V(D)J recombination therefore is not involved in affinity maturation but in primary B cell development and antibody assembly.

U.S. Pat. No. 8,012,714 describes compositions and methods for generating sequence diversity in the CDR3 region of de novo generated immunoglobulins in vitro. The methods comprise constructing nucleic acid molecules that comprise polynucleotide sequences encoding immunoglobulin V, D, J and C regions, together with recombination signal sequences (RSS), and subsequently introducing these nucleic acid molecules into suitable recombination-competent host cells. The methods provide for the assembly of gene segments to generate a functional antibody in vitro.

The use of "protein scaffolds" for the generation of novel binding proteins via combinatorial engineering has recently emerged as a powerful alternative to natural or recombinant antibodies. It has been found that novel binding sites can be introduced into proteins from several protein families with non-Ig architectures by combinatorial engineering, such as site-directed random mutagenesis combined with phage display or other selection techniques (Rothe, A., et al., 2006, *FASEB J.*, 20:1599-1610). This concept requires a stable protein architecture ("scaffold") tolerating multiple substitutions or insertions at the primary structural level (see reviews by Binz, H. K., et al., 2005, *Nature Biotechnology*, 23(10):1257-1268; Nygren, P-A. & Skerra, A., 2004, *J Immunol. Methods*, 290:3-28, and Gebauer, M. & Skerra, A., 2009, *Curr. Op. Chem. Biol.*, 13:245-255).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods and compositions for generating sequence diversity in proteins. In accordance with an aspect of the invention, there is provided a method of generating variants of a target protein comprising the steps of: (i) providing a polynucleotide comprising a nucleic acid sequence encoding the target protein and comprising a sequence cassette that comprises a first recombination signal sequence (RSS) linked by an intervening nucleotide sequence to a second RSS, the first RSS capable of functional recombination with the second RSS, wherein the first and second RSS are located in a portion of the nucleic acid sequence that encodes a non-conformational region of the target protein, and wherein the first intervening nucleotide sequence is 100 base pairs or more in length; (ii) introducing the polynucleotide into a recombination-competent host cell, and (iii) culturing the host cell in vitro under conditions allowing recombination and expression of the nucleic acid sequence, thereby generating variants of the target protein.

In accordance with another aspect of the invention, there is provided a polynucleotide comprising a nucleic acid sequence encoding a target protein and comprising a sequence cassette that comprises a first recombination signal sequence (RSS) linked by an intervening nucleotide sequence to a second RSS, the first RSS capable of functional recombination with the second RSS, wherein the first and second RSS are located in a portion of the nucleic acid sequence that encodes a non-conformational region of the target protein, and wherein the intervening nucleotide sequence is 100 base pairs or more in length.

In accordance with another aspect, there is provided an isolated host cell comprising a polynucleotide of the invention.

In accordance with another aspect, there is provided a variant protein produced by the methods described herein.

BRIEF DESCRIPTION OF THE DRAWINGS

These and other features of the invention will become more apparent in the following detailed description in which reference is made to the appended drawings.

FIG. 1 presents a partial nucleotide sequence of avimer construct E188 that comprises a single avimer A domain, a pair of RSSs introduced into loop 1 of the construct and a pair of RSSs introduced into loop 2 of the construct together with flanking sequences encoding GY amino acid residues [SEQ ID NO:28].

FIG. 2 presents a partial nucleotide sequence of avimer construct E189 that comprises double avimer A domains and a pair of RSSs in each loop 1 of the construct, as well as stop codons in other reading frames in the 3' loop 1.1 to 5' loop 1.2 region [SEQ ID NO:29].

FIG. 6 depicts (A) the nucleotide and amino acid sequences of RSS flanked cassettes used to introduce sequence diversity into avimer sequences [SEQ ID NOs:86 & 87], and (B) the nucleotide and amino acid sequences of RSS flanked cassettes used to introduce sequence diversity into avimer sequences in which the CCA nucleotides have been changed to TGT introducing cysteines in two additional reading frames (nucleotide sequence: SEQ ID NO:88; amino acid sequences: SEQ ID NOs:89-91).

FIG. 7 depicts (A) the nucleotide sequence containing the 10Fn3 coding sequence [SEQ ID NO:34] used in the preparation of 10Fn3 constructs, (B) the amino acid sequence encoded by the nucleotide sequence shown in (A) [SEQ ID NO:39], (C) a schematic representation of the acceptor vector used in the construction of the 10Fn3 constructs and for CDR diversification, and (D) the nucleotide sequences for the vector represented in (C) [SEQ ID NO:35] (BsaI and KpnI restriction sites are bolded).

FIG. 10 presents (A) the sequence of the construct shown in FIG. 9A [SEQ ID NO:37], in which the 23 bp RSS and the 12 bp RSS are shown in bold, and (B) the sequence of the construct shown in FIG. 11A [SEQ ID NO:38], in which the 23 bp RSS and the 12 bp RSS are shown in bold.

FIG. 13 presents (A) a schematic representation of the positions selected within CDR1 and CDR2 of an immunoglobulin heavy chain for insertion of pairs of RSSs, (B) sequence details selected for the 5' and 3' junctions selected for the CDR1 RSS placement [topmost sequence: SEQ ID NO:102; bottom sequence: SEQ ID NO: 115], and (C) sequence details for the 5' and 3' junctions selected for the CDR2 RSS placement [topmost sequence: SEQ ID NO:103; bottom sequence: SEQ ID NO: 116].

FIG. 14 presents (A) a schematic representation of the immunoglobulin heavy chain shown in FIG. 13 including a pair of RSSs in CDR2, (B) sequence details of the 23 bp RSS shown in (A) [topmost sequence: SEQ ID NO:104; bottom sequence: SEQ ID NO: 117], and (C) sequence details of the 12 bp RSS shown in (A) [topmost sequence: SEQ ID NO:105; bottom sequence: SEQ ID NO: 118].

FIG. 15 presents (A) a schematic representation of the immunoglobulin heavy chain shown in FIG. 13 including a pair of RSSs, together with 5' trinucleotide repeat flanking sequences, in each of CDR1 and CDR2, (B) sequence details of the 5' 23 bp RSS shown in (A) [topmost sequence: SEQ ID NO:106; bottom sequence: SEQ ID NO: 119], (C) sequence details of the 5' 12 bp RSS shown in (A) [topmost sequence: SEQ ID NO:107; bottom sequence: SEQ ID NO: 120], (D) sequence details of the 3' 12 bp RSS shown in (A) [topmost sequence: SEQ ID NO:108; bottom sequence: SEQ ID NO: 121], and (E) sequence details of the 3' 23 bp RSS shown in (A) [topmost sequence: SEQ ID NO:109; bottom sequence: SEQ ID NO: 122].

FIG. 16 shows (A) the nucleotide sequence of the unmodified immunoglobulin heavy chain depicted schematically in FIG. 13 [SEQ ID NO:3] with the CDR1 and CDR2 regions shown in bold, (B) the nucleotide sequence of the immunoglobulin heavy chain including a pair of complementary RSSs positioned within CDR2 as depicted schematically in FIG. 14A [SEQ ID NO:4] with the RSSs shown in bold, and (C) the nucleotide sequence of the immunoglobulin heavy chain including a pair of RSSs positioned, together with 5' trinucleotide repeat flanking sequences, within each of CDR1 and CDR2 as depicted schematically in FIG. 15A [SEQ ID NO:5], with the RSSs shown in bold.

FIG. 17 presents the nucleotide sequence for the vector E188 [SEQ ID NO:1].

FIG. 18 presents the nucleotide sequence for the vector E189 [SEQ ID NO:40].

FIG. 19 presents (A) a schematic representation of a cassette for generating in-frame selection of a secreted protein (shown is Ig Kappa) showing from constant region to poly(A), and (B) the nucleotide sequence of the cassette shown in (A) [SEQ ID NO:41] with the furin cleavage site in bold.

FIG. 20 presents the nucleotide sequence for the vector ITS001-V655 [SEQ ID NO:74].

FIG. 21 presents (A) a schematic diagram of the light chain CDR2 optimization cassette from the vector ITS001-V655, and (B) the results from FACS-based analysis of HER2 binding versus antibody expression for a population of cells expressing light chain CDR2 optimized antibodies (ITS001-L145) as compared to cells expressing the original antibody.

FIG. 22 presents (A) a bar chart summarizing the results of a FACS-based assay of HER2 binding to cells expressing light chain CDR2 optimized antibodies cloned from ITS001-L145 relative to cells expressing the original antibody, and (B) results from the FACS-based assay for an individual clone (Clone 9) as compared to the original antibody.

FIG. 23 presents (A) the results from FACS-based analysis of HER2 binding versus antibody expression for a population of cells expressing light chain CDR1 optimized antibodies (ITS001-L167) as compared to cells expressing the original antibody, (B) a bar chart summarizing the results of a FACS-based assay of HER2 binding to cells expressing light chain CDR1 optimized antibodies cloned from ITS001-L167 relative to cells expressing the original antibody, and (C) results from the FACS-based assay for an individual clone (Clone 15) as compared to the original antibody.

DETAILED DESCRIPTION OF THE INVENTION

Figure 3C:
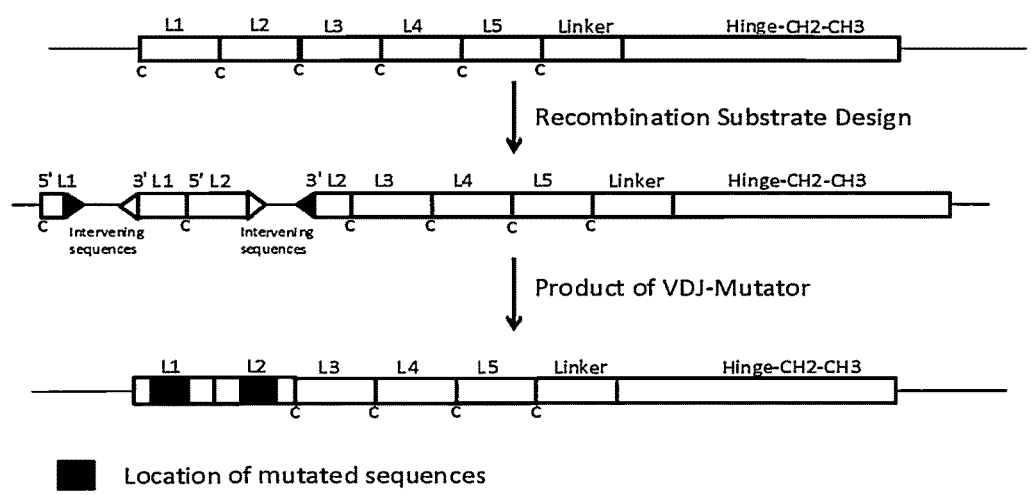
FIG. 3 presents (A) a schematic representation of a single domain A avimer construct comprising a pair of RSSs in loop 1 and a pair of RSSs in loop 2, a selectable marker was included between the Tm domain and the poly A; (B) sequence details of the construct shown in (A) with arrows indicating the positions of insertion of the RSS cassettes, and (C) a schematic overview of the steps for mutagenesis of the single domain A avimer construct shown in (A).

The present invention is based on the finding, illustrated herein, that the use of components of the antibody V(D)J recombination system can be expanded outside their natural role of mediating assembly of antibody gene segments to their use to modify an existing protein sequence.

Accordingly, in certain embodiments, the invention relates to methods of generating sequence diversity in a known protein sequence, such as a ligand-binding protein sequence, by targeted introduction of two or more recombination signal sequences (RSSs) into the protein coding sequence and subsequent introduction of the modified protein coding sequence into a recombination-competent host cell, specifically a host cell that is capable of expressing at least RAG-1 and RAG-2, resulting in the generation and expression of variants of the protein. In certain embodiments, the present invention relates to polynucleotides comprising a nucleic acid sequence encoding a target protein, such as a ligand-binding protein, and comprising two or more RSSs, and compositions comprising same.

The present invention recognizes that the natural V(D)J reaction has inherent characteristics, specifically the imprecise junctions generated during the joining process, that make it useful as a general means to generate sequence diversity. The use of V(D)J recombination as a method to modify an existing protein sequence as opposed to assembly of a protein from gene segments, however, has a number of challenges, including a number of features of the reaction that are under-appreciated in the art.

The V(D)J recombination reaction is known to bring together different DNA sequences and result in large chromosomal deletions, which suggests that its utility to introduce sequence diversity would be limited to extended stretches of nucleic acid sequence that permit such large deletions. As demonstrated herein, however, the components of the V(D)J recombination system can be manipulated to allow the utility of this reaction to be extended to include targeted sequences within a restricted size of protein sequence, such as a small loop.

In addition, although the involvement of the enzyme TdT, which is responsible for non-template nucleotide additions (N-additions), is central to the reaction, the net size of the product following gene segment assembly is frequently less than would be predicted if no deletions or additions were to occur, i.e. the V(D)J reaction often results in a net loss of sequence. For example, the average size of the assembled germline V, D and J segments, without any additions or deletions, is 15 amino acids and yet the average CDR3 reported in humans is 12-13 amino acids, which includes N additions from TdT (Rock et al., 1994, *J Exp Med,* 179:323-328).

Another feature of V(D)J recombination that is under-appreciated is that the additions introduced by TdT are small. In vivo and in vitro TdT additions have been reported to be typically an average of 2-4 nucleotides (Kallenbach et al., 1992, *PNAS USA,* 89:2799-2903; Bentolila et al., 1997, *J Immunol.,* 158:715-723). An larger number of amino acid changes per variant is generally preferred for mutagenesis techniques in order to allow for a greater amount of diversity to be sampled.

The above-noted features of V(D)J recombination can represent challenges to the application of V(D)J recombination to a non-antibody scaffold. The methods provided by the present invention, however, allow for this random deletional process to be used as a valuable tool for semi-rational protein engineering.

In some embodiments, for example, the methods employ flanking sequences adjacent to one or more of the RSSs to allow for incorporation of additional sequences into the final variant protein to minimise any net deletion effect of the V(D)J recombination reaction and/or to introduce additional functionality by way of addition of specific amino acid residues. By way of example, when the targeted location is within a small loop of a protein, flanking sequences may be used in conjunction with the RSSs to ensure that the loop retains a minimal length once sequence diversification has taken place.

The V(D)J reaction in vivo generates deletions and additions of different size and composition on either side of the junctions flanked by the RSSs. In certain embodiments, the methods of the present invention allow for control of the reaction so that deletions can be focused to one junction or the other through the use of flanking sequences. In some embodiments, the methods allow for specific heterologous sequences to be incorporated into the final variant protein through the use of flanking sequences.

In addition, in some embodiments, the methods make use of a tripartite reaction that involves two pairs of RSSs so that diversity is generated at two junctions rather than a single junction. In accordance with those embodiments in which a tripartite reaction is employed, sequence diversity may be introduced at a single target location in the protein, or at two independent locations in the protein. Use of a tripartite reaction with an appropriately sized RSS flanked donor cassette sequence also allows for the incorporation of sequences from the donor cassette at the targeted location. In certain embodiments, the methods provide for sequence diversity to be introduced at a single location by way of a "bipartite" reaction that involves a single pair of RSSs, which may be used with or without flanking sequences.

The methods in accordance with the present invention have a number of features that make them attractive for generating sequence diversity. For example, the diversity can be targeted so that mutations are focused at one or more predetermined locations as opposed to being randomly distributed across a protein as would be the result of traditional approaches, such as PCR- or somatic hypermutation (SHM)-based approaches. The methods may also be used to simultaneously introduce mutations at two different target locations within the protein. These locations may be close together or distant, in terms of either sequence or structure. For example, in certain embodiments, the methods are used to simultaneously introduce sequence diversity simultaneously into two separate loops of a target protein.

In addition, in certain embodiments, the methods of the present invention allow for the generation of both composition and length diversity simultaneously. In some embodiments, the methods are entirely cell-mediated thus eliminating the requirement for cloning of variants and their subsequent introduction into cells as is required by other methods.

The methods of the present invention additionally allow for the generation of a very large number of protein variants such that, in certain embodiments, mutations imparting the desired functionality to the protein can be identified in a single round. For example, for binding proteins, the attainable affinity from a library of random binding proteins is assumed to increase with its diversity (Griffiths, A. D., et al., 1994, *EMBO J.,* 13:3245-3260). Accordingly, the methods in accordance with certain embodiments of the present invention provide for the generation of sufficient diversity within a target binding protein to allow for variants with high affinity for a selected ligand to be generated in a single round.

The methods in accordance with certain embodiments of the invention include the use of flanking sequences adjacent to the RSSs and/or tripartite substrate structures to allow for the production of a large repertoire of functional variants.

In certain embodiments, the methods employ an inducible form of one or more of the components of the recombination system to allow induction of sequence diversity generation to be controlled, for example to allow for expansion of the host cell prior to induction of sequence diversity generation.

In general, the methods comprise the steps of introducing a pair of RSSs at a selected location within the coding sequence for a target protein, introducing the modified coding sequence into a cell that is capable of expressing at least RAG-1 and RAG-2 to allow for recombination and expression of the variant protein.

DEFINITIONS

Unless defined otherwise, all technical and scientific terms used herein have the same meaning as commonly understood by one of ordinary skill in the art to which this invention belongs.

"Naturally occurring," as used herein with reference to an object, refers to the fact that the object can be found in nature. For example, an organism, or a polypeptide or polynucleotide sequence that is present in an organism that can be isolated from a source in nature and which has not been intentionally modified by man in the laboratory is naturally occurring.

The term "isolated," as used herein with reference to a material, means that the material is removed from its original environment (for example, the natural environment if it is naturally occurring). For example, a naturally occurring polynucleotide or polypeptide present in a living animal is not isolated, but the same polynucleotide or polypeptide separated from some or all of the co-existing materials in the natural system, is isolated. Such polynucleotides could be part of a vector and/or such polynucleotides or polypeptides could be part of a composition, and still be isolated in that such vector or composition is not part of its natural environment.

The term "gene," as used herein, refers to a segment of DNA involved in producing a polypeptide chain. The segment of DNA may include regions preceding and/or following the coding region, as well as intervening sequences (introns) between individual coding segments (exons), and may also include regulatory elements (for example, promoters, enhancers, repressor binding sites and the like).

The term "deletion" as used herein with reference to a polynucleotide, polypeptide or protein has its common meaning as understood by those familiar with the art and may refer to molecules that lack one or more of a portion of a sequence from either terminus or from a non-terminal region, relative to a corresponding full length molecule. For example, in certain embodiments, a deletion may be a deletion of between 1 and about 1500 contiguous nucleotide or amino acid residues from the full length sequence.

The term "expression vector," as used herein, refers to a vehicle used in a recombinant expression system for the purpose of expressing a polynucleotide sequence constitutively or inducibly in a host cell, including prokaryotic, yeast, fungal, plant, insect or mammalian host cells, either in vitro or in vivo. The term includes both linear and circular expression systems. The term includes expression systems that remain episomal and expression systems that integrate into the host cell genome. The expression systems can have the ability to self-replicate or they may not (for example, they may drive only transient expression in a cell).

The term "antigen-binding domain," as used herein, refers to one or more fragments of an antibody that retain the ability to specifically bind to an antigen. Non-limiting examples of antibody fragments comprising antigen-binding domains include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulphide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR). The term also encompasses single chain Fv (scFv) fragments, which comprise the two domains of the Fv fragment, $V_L$ and $V_H$, joined using recombinant methods by a synthetic linker that enables them to be made as a single protein chain in which the $V_L$ and $V_H$ regions pair to form monovalent molecules.

The term "bipartite reaction," as used herein, refers to a recombination reaction that involves a single pair of RSSs (12 bp and 23 bp, or 23 bp and 12 bp). When V(D)J recombination occurs it generates a double-stranded break in the nucleic acid sequence containing the RSSs. The double-stranded break is targeted as a result of the RSSs in that a 12 bp and 23 bp RSS are assembled with the RAG proteins to initiate the reaction. The ends of the DNA that will be subsequently rejoined will comprise the coding joint (or junction). An example of a bipartite reaction is in vivo immunoglobulin light chain recombination, which joins the Variable to the Joining segment—these two segments comprise the "substrates" for the bipartite reaction. The bipartite reaction can occur in the presence or absence of TdT.

The term "tripartite reaction," as used herein, refers to a recombination reaction that involves two pairs of RSSs (each 12 bp and 23 bp, or 23 bp and 12 bp). An example of a tripartite reaction is in vivo immunoglobulin heavy chain recombination, which joins the V, the D and the J gene segments. A tripartite reaction generates two independent coding junctions. Two sequential bipartite reactions can be considered to be a tripartite reaction in that a tripartite reaction may comprise two bipartite reactions occurring in the same substrate, usually (but not always) in close temporal time. The tripartite reaction can occur in the presence or absence of TdT.

The term "recombination-competent" when used herein with reference to a host cell means that the host cell is capable of mediating RAG-1/RAG-2 recombination. The host cell may, therefore, express RAG-1 and RAG-2, or functional fragments thereof, or may be modified (for example, transformed or transfected with appropriate genetic constructs) such that it expresses RAG-1 and RAG-2, or functional fragments thereof. The expression of one or both of RAG-1 and RAG-2 in the recombination-competent host cell may be constitutive or it may be inducible. A recombination-competent host cell may optionally further express TdT, or a functional fragment thereof.

As used herein, the term "about" refers to an approximately +/−10% variation from a given value. It is to be understood that such a variation is always included in any given value provided herein, whether or not it is specifically referred to.

The term "plurality" as used herein means more than one, for example, two or more, three or more, four or more, and the like.

Methods of Generating Sequence Diversity

The methods according to the present invention generally comprise the steps of introducing a pair of RSSs at a selected location within the coding sequence for a target protein, and introducing the modified coding sequence into a recombination-competent host cell to allow for recombination and expression of variants of the target protein. Accordingly, in its simpler aspects, the present invention provides methods of generating variants of a target protein comprising the steps of: providing a polynucleotide comprising a nucleic acid sequence encoding a target protein and comprising a complementary pair of RSSs, introducing the polynucleotide into a recombination-competent host cell, the host cell capable of expressing at least RAG-1 and RAG-2, and culturing the host cell in vitro under conditions allowing recombination and expression of the polynucleotide, thereby generating variants of the target protein. In certain embodiments, the methods further comprise screening the variant proteins for variants having defined functional characteristics.

In certain embodiments of the present invention, the methods are applied to a target protein that is a ligand-binding protein. In some embodiments, the methods are applied to a ligand-binding protein in order to introduce sequence diversity into a loop region involved in ligand-binding and comprise the steps of: providing a polynucleotide comprising a nucleic acid sequence encoding a target ligand-binding protein, the nucleic acid sequence comprising a complementary pair of RSSs in a region of the sequence encoding a ligand-binding loop of the protein, introducing the polynucleotide into a recombination-competent host cell, and culturing the host cell under conditions allowing recombination and expression of the polynucleotide, thereby generating variants of the target ligand-binding protein.

The host cell may constitutively express RAG-1 and RAG-2, and optionally TdT, or one or more of these proteins may be under inducible control. In certain embodiments, expression of one or more of RAG-1 and RAG-2, and optionally TdT, in the host cell is under inducible control allowing, for example, for expansion of the host cell prior to the induction of sequence diversity generation. Accordingly, in some embodiments, the method comprises the steps of: providing a polynucleotide comprising a nucleic acid sequence encoding a target protein and comprising a pair of RSSs, introducing the polynucleotide into a recombination-competent host cell, the host cell capable of expressing at least RAG-1 and RAG-2 and optionally TdT, wherein expression of one or more of RAG-1, RAG-2 and TdT is under inducible control, culturing the host cell under conditions allowing expansion of the host cell, inducing expression of one or more of RAG-1, RAG-2 and TdT, culturing the expanded host cells under conditions allowing recombination and expression of the polynucleotide, thereby generating variants of the target protein.

The polynucleotide may be introduced into the host cell on a suitable vector and may be, for example, stably integrated into the genome of the cell, stably maintained exogenously to the genome or transiently expressed.

In some embodiments, the nucleic acid encoding the target protein comprised by the polynucleotide is operably linked to a regulatable promoter, for example, an inducible promoter, such that expression of the target protein can be controlled.

In certain embodiments, the polynucleotide may comprise additional pairs of RSSs allowing for generation of additional sequence diversity in the protein. In some embodiments, the polynucleotide comprises two complementary pairs of RSSs, each pair positioned to introduce sequence diversity into a different region of the target protein.

In some embodiments, the polynucleotide may also comprise additional coding sequences and thus may encode a fusion protein comprising the target protein fused to a polypeptide that provides additional functionality to the protein. For example, the polypeptide may localize the target protein to the cell membrane, nucleus or other organelle; provide for secretion of the target protein from the cell; introduce a detectable label, or the like.

In certain embodiments, the recombination is controlled. In some embodiments, the host cell is capable of cell divisions without recombination. As described herein, these and related embodiments permit expansion of the host cell population prior to the initiation of recombination events that give rise to sequence diversity in the target protein. Control of recombination in such host cells may be achieved, for example, through the use of an operably linked recombination control element (such as an inducible recombination control element, which may be a tightly regulated inducible recombination control element), and/or through the use of one or more low efficiency RSSs in the polynucleotide (as described in more detail below), and/or through the use of low host cell expression levels of one or more of RAG-1 or RAG-2, and/or through design of the polynucleotide to integrate at a chromosomal integration site offering poor accessibility to host cell recombination mechanisms (for example, RAG-1 and/or RAG-2).

In some embodiments, the methods further comprise selecting a variant having the desired functional characteristics. In some embodiments, the methods further comprise subjecting a selected variant to one or more additional rounds of sequence diversity generation in order to obtain further variants having optimised functional characteristics.

Target Proteins

In accordance with the present invention, the methods of generating sequence diversity may be applied to a wide variety of proteins for which a functional assay can be designed for screening. In accordance with certain embodiments of the invention, the target protein of the methods is preferably a ligand-binding protein, wherein the ligand may be an antigen, another protein, a nucleic acid, a carbohydrate, a lipid, a metal, a vitamin or the like. In the context of the present invention, the term "ligand-binding protein" includes receptor-binding proteins. In some embodiments, the target protein is a ligand-binding protein, wherein the ligand is another protein, a nucleic acid, a carbohydrate, a lipid, a vitamin or a metal. In some embodiments, the target protein is a ligand-binding protein, wherein the ligand is another protein. In certain embodiments, the target protein is a ligand-binding protein, wherein the ligand is an antigen. In some embodiments, the target protein is a receptor-binding protein.

In some embodiments, the target protein of the methods is an immunoglobulin, wherein the target location(s) for introduction of sequence diversity are the CDR1 and/or CDR2 region. The natural process of B cell development does not involve V(D)J recombination of CDR1 and/or CDR2. As described herein, however, the use of components of the antibody V(D)J recombination system can be expanded to introduce sequence diversity at CDR1 and/or CDR2 in order to generate antibodies with improved affinity and/or specificity.

In certain embodiments, the target protein is an existing immunoglobulin and the target location is CDR3, wherein the existing CDR3 can be sequence diversified to generate improved binding characteristics (for example improved affinity or specificity) over the original immunoglobulin.

The immunoglobulin may comprise a germline sequence or it may comprise a sequence that has already undergone affinity maturation or one or more artificial sequence optimization steps to improve the affinity of the immunoglobulin. Accordingly, in some embodiments, the methods can be used to improve the affinity of a germline immunoglobulin, and in some embodiments, the methods can be used to further improve the affinity of a known immunoglobulin.

In certain embodiments, the target protein of the methods is an immunoglobulin, wherein the target location(s) for introduction of sequence diversity is a non-CDR loop of the Ig molecule located in the constant region of the protein.

Immunoglobulins that may be used as target proteins in the methods of the present invention are antibodies or antibody fragments that comprise an antigen-binding domain including at least one of a CDR1, CDR2 or CDR3. Examples include, but are not limited to, IgA, IgA2, IgD, IgE, IgGs (i.e. IgG1, IgG2, IgG3 and/or IgG4) and IgM antibodies; camelid antibodies; HCAns; single chain antibodies; shark antibodies; antibody fragments such as Fab, Fab', F(ab')$_2$, Fd, Fv and single-chain Fv (scFv) antibody fragments; diabodies, nobodies and fluorobodies. In certain embodiments, the target protein is an IgG antibody or fragment thereof. In some embodiments, the target protein is an immunoglobulin $V_H$ chain or $V_L$ chain.

Immunoglobulins suitable for use in the methods described herein may be derived from a variety of sources and technologies including, but not limited to, mammals including mice, transgenic mice and humans, phage display or yeast display, or they may be synthetically derived immunoglobulins or fragments thereof.

In one embodiment, the methods are applied to a target protein that is a non-immunoglobulin protein.

Non-immunoglobulin ligand-binding proteins that may be used as target proteins include naturally-occurring proteins and non-naturally occurring proteins.

Naturally-occurring ligand-binding proteins include human proteins and non-human proteins, for example, proteins from a non-human animal, a plant, or a micro-organism. Examples of naturally-occurring ligand-binding proteins include, but are not limited to, biotin-binding proteins (such as avidin and streptavidin), lipid-binding proteins (such as β-lactoglobulin, $α_1$-microglobulin and plasma transthyretin), periplasmic binding proteins, lectins, serum albumins, phosphate binding proteins, sulphate binding proteins, immunophilins, metal-binding proteins, DNA-binding proteins, GTP-binding proteins (G-proteins), transporter proteins and receptor proteins (soluble and non-soluble). Non-limiting examples of metal-binding proteins include transferrin, ferritin and metallothionein. Non-limiting examples of DNA-binding proteins include histones, transcription factors, single-stranded DNA-binding proteins and helicases. Non-limiting examples of transporter and receptor proteins include, haemoglobin, cytochromes, G-protein coupled receptors, adrenalin receptors, acetylcholine receptors, histamine receptors, dopamine receptors, serotonin receptors, glutamate receptors, serotonin transporters, oestrogen receptors, $Ca^{2+}$ channels, $Na^+$ channels and $Cl^-$ channels. Non-limiting examples of soluble receptors include receptors for peptide hormones or cytokines, such as receptors for growth factors, lymphokines, monokines, interleukins, interferons, chemokines, colony-stimulating factors, hematopoietic factors, neurotrophic factors and differentiation-inhibiting factors. In certain embodiments, the ligand-binding protein may be a T-cell receptor.

Non-naturally occurring ligand-binding proteins include polypeptides that comprise one or more ligand-binding domains or fragments of naturally-occurring proteins capable of binding a ligand, such as fibronectin III domains (for example, FN3 and Adnectins™), the immunoglobulin binding domain of *Staphylococcus aureus* protein A ("affibodies"), src homology domains 2 and 3 (SH2 and SH3, respectively) and PDZ domains. Non-naturally occurring ligand-binding proteins also include artificial ligand-binding proteins such as designed ankyrin repeat proteins ("DARPins"), avimers and aptamers.

In certain embodiments, the non-naturally occurring ligand-binding proteins are protein scaffolds consisting of a stably folded non-Ig protein capable of being equipped with a binding site as described in Binz, et al. (2005, *Nature Biotechnology*, 23(10):1257-1268), Nygren & Skerra (2004, *J Immunol. Methods*, 290:3-28) and Gebauer & Skerra (2009, *Curr. Op. Chem. Biol.*, 13:245-255). Examples of such protein scaffolds include, but are not limited to, cytotoxic lymphocyte-associated antigen-4 (CTLA-4), Tendamistat, 10$^{th}$ fibronectin type 3 domain ($^{10}$FN3), carbohydrate-binding module 4 of family 2 of xylanase of *Rhodothermus marinus* (CBM4-2), lipocalins ("anticalins"), T-cell receptor, Protein A domain (protein Z), immunity protein 9 (Im9), designed ankyrin repeat proteins (DARPins), designed tetratrico repeat (TPR) proteins, zinc finger proteins, protein VIII of filamentous bacteriophage (pVIII), avian pancreatic polypeptide, general control non-derepressible (yeast transcription factor) (GCN4), WW domain, Src homology domain 3 (SH3), Src homology domain 2 (SH2), PDZ domains, TEM-1, β-lactamase, green fluorescent protein (GFP), thioredoxin, staphylococcal nuclease, plant homeodomain finger protein (PHD-finger), chymotrypsin inhibitor 2 (CI-2), bovine pancreatic trypsin inhibitor (BPTI), Alzheimer amyloid β-protein precursor inhibitor (APPI), human pancreatic secretory trypsin inhibitor (hPSTI), ecotin, human lipoprotein-associated coagulation inhibitor domain 1 (LACI-D1), leech-derived trypsin inhibitor (LDTI), MTI-II, scorpion toxins, insect defensin A peptide, Ecballium elaterium trypsin inhibitor II (EETI-II), Min-23, cellulose-binding domain (CBD), periplasmic binding proteins (PBP), cytochrome $b_{562}$, low density lipoprotein (ldl) receptor domain A, γ-crystallin, ubiquitin, transferrin and C-type lectin-like domain.

Protein scaffolds can be considered as falling into two groups: a first group consisting of loop presenting scaffolds (which includes scaffolds presenting a single loop and scaffolds presenting a plurality of loops), and a second group consisting of interface presenting scaffolds, in which the binding site is presented on a secondary structure element. Examples of scaffolds in the first group include, but are not limited to, Kunitz domain inhibitors, hPSTI, APPI, LACI-D1, ecotin, members of the knottin family of proteins (such as EETI-II), thioredoxin, staphylococcal nuclease, immunoglobulins, CTLA-4, FN3, Tendamistat, GFP, members of the lipocalin family of proteins, and bilin binding protein (BBP) from *Pieris brassicae*. Examples in the second group include, but are not limited to, the immunoglobulin binding domain of Staphylococcal protein A (SPA) ("affibodies"), DARPins, leucine-rich repeat polypeptides, PDZ domains, cellulose binding domains (CBD), members of the lipocalin family of proteins, γ-crystallins, and Cys$_2$His$_2$ zinc-finger polypeptides. The binding domains of both of these groups of proteins have been studied and regions suitable for modification have been identified (see review by Nygren & Skerra, ibid.). The present invention contemplates that in various embodiments, the methods described herein may be applied to both loop presenting scaffolds and to interface presenting scaffolds. In certain embodiments, therefore, the target protein for the methods is a loop presenting scaffold protein, wherein sequence diversity is introduced into one or more loops. In some embodiments, the target protein for the methods is an interface presenting scaffold protein, in which sequence diversity is introduced into the binding site.

In certain embodiments, the methods are applied to target proteins that comprise a ligand-binding region that includes one or more loops, in which a loop can be defined as a region supported by a protein scaffold that can carry altered amino acids or sequence insertions without substantially compromising the structure of the scaffold, and wherein sequence diversity is introduced into one or more of the loops. In some embodiments, the methods are applied to target proteins that comprise a ligand-binding region that includes one or more surface-exposed loops, wherein one or more of the loops are targeted locations for introduction of sequence diversity. Examples of loop containing proteins are found within various categories of proteins described above and include, for example, immunoglobulins and loop presenting scaffold proteins.

While the term "target protein" is used herein, it is to be understood that the methods of the present invention are equally applicable to protein fragments and that the term "target protein" thus incorporates both the full length protein and fragments of the protein, for example, functional fragments, fragments comprising one or more domains, and the like. In certain embodiments, fragments include one or more deletions from either terminus of the protein or a deletion from a non-terminal region of the protein, for example, in some embodiments, deletions of between about 1 and about 500 contiguous amino acid residues. In some embodiments, the fragments may comprise a deletion of between about 1 and about 300 contiguous amino acid residues, for example, between 1 and about 250 contiguous amino acid residues, between 1 and about 200 contiguous amino acid residues, between 1 and about 150 contiguous amino acid residues, between 1 and about 100 contiguous amino acid residues, or between 1 and about 50 contiguous amino acid residues, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 contiguous amino acid residues. In some embodiments, deletions of between 1-30, 31-40, 41-50, 51-60, 61-70, 71-80, 81-90, 91-100, 101-150, 151-200, 201-250 or 251-300 contiguous amino acid residues are contemplated.

Certain embodiments of the invention also contemplate that the methods may be applied to variants of a target protein, for example, naturally-occurring variants, or variants that have been generated by conventional mutagenesis methods in order to modulate a property of the protein. Variants generated by the present methods are also suitable candidates for additional rounds of sequence diversity generation in order to further modulate one or more property of the protein.

Polynucleotides

Polynucleotides employed in the methods of the present invention comprise a nucleic acid sequence encoding a target protein ("coding sequence"). The polynucleotides may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A nucleic acid sequence which encodes a target protein for use in the methods of the present invention may be identical to the coding sequence known in the art for the target protein or may be a different coding sequence, which, as a result of the redundancy or degeneracy of the genetic code, encodes the same protein.

The polynucleotides may include only the coding sequence for the target protein; the coding sequence for the target protein and additional coding sequence; the coding sequence for the target protein (and optionally additional coding sequence) and non-coding sequence, such as introns or non-coding sequences 5' and/or 3' of the coding sequence. The coding sequence may be in the form of one or more exons, which may be contiguous or may be interspersed with one or more introns. The non-coding sequences may include, for example, one or more regulatory nucleic acid sequences that may be a regulated or regulatable promoter, enhancer, other transcription regulatory sequence, repressor binding sequence, translation regulatory sequence or other regulatory nucleic acid sequence. Thus, the term "polynucleotide encoding" a target protein encompasses a polynucleotide which includes only coding sequence for the target protein as well as polynucleotides that include additional coding and/or non-coding sequence(s).

The coding sequence for various proteins suitable for use as target proteins are known in the art and can be obtained from public databases such as GenBank. Many proteins have been cloned and polynucleotides comprising the coding sequences for these proteins may be obtained from commercial sources. Alternatively, coding sequences can be obtained from an appropriate source using standard molecular biology techniques, such as those described in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.). In addition, many companies offer custom gene synthesis and may be used as a source of coding sequences for a target protein.

As noted above, the term "target protein" as used herein includes both the full-length protein and fragments of the protein. Accordingly, the polynucleotides for use in the methods of the invention that encode a target protein may encode the full length protein or a fragment thereof. In some embodiments, the polynucleotide may be a truncated nucleic acid molecule which has less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene may comprise coding sequences and optionally non-coding sequences, promoters, enhancers and other regulatory sequences, flanking sequences and the like, and other functional and non-functional sequences that are recognized as part of the gene. In certain embodiments, truncated nucleic acid molecules correspond to a mRNA sequence and contain less than the full length mRNA transcript, which may include various translated and non-translated regions as well as other functional and non-functional sequences. In certain embodiments, truncated nucleic acid molecules may include one or more deletions from either terminus of the polynucleotide or a deletion from a non-terminal region of the polynucleotide, for example, in some embodiments, deletions of between about 1 and about 1500 contiguous nucleotides. In some embodiments, truncated nucleic acid molecules may include deletions of between 1 and about 1200 contiguous nucleotides, for example, between 1 and about 1000 contiguous nucleotides, between 1 and about 750 contiguous nucleotides, between 1 and about 500 contiguous nucleotides, between 1 and about 300 contiguous nucleotides, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotides.

In certain embodiments, the polynucleotide may be codon-optimized according to standard codon usage preference tables, such that its expression in the chosen host cell is optimized.

Certain embodiments of the invention encompass the use of variant polynucleotides in the present methods, for example, polynucleotides that encode analogs and/or derivatives of a target protein. The polynucleotide variants may be, for example, naturally-occurring allelic variants of the polynucleotide or non-naturally occurring variants. As is known in the art, an allelic variant is an alternate form of a nucleic acid sequence which may have at least one of a substitution, a deletion or an addition of one or more nucleotides, any of which does not substantially alter the function of the encoded protein. Non-naturally occurring polynucleotide variants may be accomplished by a number of conventional methods. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion(s), substitution(s), or deletion(s). Alternatively, oligonucleotide-directed site-specific mutagenesis procedures can be employed to provide an altered gene wherein predetermined codons can be altered by substitution, deletion or insertion. Exemplary methods of making such alterations are described, for example, in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.).

In certain embodiments, as noted above, the target protein may be a variant with modulated properties. Polynucleotides that encode such variants are thus also contemplated and may be generated by conventional mutagenesis methods as described above or by the present methods as candidates for additional rounds of sequence diversity generation.

Recombination Signal Sequences (RSSs)

The recombination signal sequence (RSS) in accordance with the present invention preferably consists of two conserved sequences (for example, heptamer, 5'-CACAGTG-3', and nonamer, 5'-ACAAAAACC-3'), separated by a spacer of either 12+/−1 bp (a "12-signal" RSS) or 23+/−1 bp (a "23-signal" RSS). Within the host cell, two RSSs (one 12-signal RSS and one 23-signal RSS) are selected and rearranged under the "12/23 rule." Recombination does not occur between two RSS signals with the same size spacer. As would be appreciated by one of skill in the art, the orientation of the RSS determines if recombination results in a deletion or inversion of the intervening sequence.

As a result of extensive investigations of RSS processes, it is known in the art which nucleotide positions within RSSs cannot be varied without compromising RSS functional activity in genetic recombination mechanisms, which nucleotide positions within RSSs can be varied to alter (for example, increase or decrease in a statistically significant manner) the efficiency of RSS functional activity in genetic recombination mechanisms, and which positions within RSSs can be varied without having any significant effect on RSS functional activity in genetic recombination mechanisms (see, for example, Ramsden et al., 1994, *Proc Natl Acad Sci USA* 88(23): 10721-10725; Akamatsu et al., 1994, *J Immunol* 153:4520; Hesse et al., 1989, *Genes Dev* 3:1053; Fanning et al., 1996, *Immunogenetics* 44(2):146-150; Larijani et al., 1999, *Nucleic Acids Res* 27(11):2304-2309; Nadel et al., 1998, *J Exp Med* 187:1495; Lee et al., 2003, *PLoS Biol* 1:E1; and Cowell et al., 2004, *Immunol. Rev.* 200:57).

In certain embodiments, the RSS selected for inclusion in the target protein coding sequence is a RSS that is known to the art. Also contemplated in some embodiments are sequence variants of known RSSs that comprise one or more nucleotide substitutions (for example, about 1, 2, 3, 4, 5, 6, 7, 8, 9, 10, 11, 12, 13, 14, 15, 16, 17, 18 or more substitutions) relative to the known RSS sequence and which, by virtue of such substitutions, predictably have low efficiency (for example, about 1% or less, relative to a high efficiency RSS), medium efficiency (for example, about 10% to about 20%, relative to a high efficiency RSS) or high efficiency. Also contemplated in some embodiments are those RSS variants for which one or more nucleotide substitutions relative to a known RSS sequence will have no significant effect on the recombination efficiency of the RSS (for example, the success rate of the RSS in promoting formation of a recombination product, as known in the art).

In accordance with certain embodiments of the invention, RSSs selected for inclusion in the target protein coding sequence are pairs of RSSs in which the first RSS of the pair is capable of functional recombination with the second RSS of the pair (i.e. "complementary pairs"). It is to be understood that when a first RSS (for example present in a first polynucleotide or nucleic acid sequence) is described as being capable of functional recombination with a second RSS (for example present in a second polynucleotide or nucleic acid sequence), such capability includes compliance with the above-noted 12/23 rule for RSS spacers, such that if the first RSS comprises a 12-nucleotide spacer then the second RSS will comprise a 23-nucleotide spacer, and similarly if the first RSS comprises a 23-nucleotide spacer then the second RSS will comprise a 12-nucleotide spacer.

Examples of RSS sequences known in the art, including their characterization as high, medium or low efficiency RSSs, are presented in Table 1A and 1B.

TABLE 1A

EXEMPLARY RECOMBINATION SIGNAL SEQUENCES (12 NUCLEOTIDE SPACER)

| | Heptamer H12 | Spacer S12 | Nonamer N12 |
|---|---|---|---|
| | Part I. Efficiency: HIGH | | |
| 1 | CACAGTG | ATACAGACCTTA [SEQ ID NO: 2] | ACAAAAACC |
| 2 | CACAGTG | CTACAGACTGGA [SEQ ID NO: 9] | ACAAAAACC |
| 3 | CACAGTG | CTCCAGGGCTGA [SEQ ID NO: 10] | ACAAAAACC |
| 4 | CACAGTG | CTACAGACTGGA [SEQ ID NO: 9] | ACAAAAACC |
| 5 | CACAGTG | CTACAGACTGGA [SEQ ID NO: 9] | ACAAAAACC |
| 6 | CACAGTG | CTACAGACTGGA [SEQ ID NO: 9] | ACAAAAACC |
| 7 | CACAGTG | GTACAGACCAAT [SEQ ID NO: 11] | ACAGAAACC |
| | Part II Efficiency: MEDIUM (~10-20% of High) | | |
| 8 | CACGGTG | CTACAGACTGGA [SEQ ID NO: 9] | ACAAAAACC |
| 9 | CACAATG | CTACAGACTGGA [SEQ ID NO: 9] | ACAAAAACC |
| 10 | CACAGCG | CTACAGACTGGA [SEQ ID NO: 9] | ACAAAAACC |
| 11 | CACAGTG | CTACAGACTGGA [SEQ ID NO: 9] | ACAAAAACC |
| 12 | CACAGTG | CTACAGACTGGA [SEQ ID NO: 9] | ACAAAAACC |
| 13 | CACAGTG | CTACAGACTGGA [SEQ ID NO: 9] | ACAAAAACC |
| 14 | CACAGTG | CTACAGACTGGA [SEQ ID NO: 9] | ACAAAAACC |
| 15 | CACAGTG | CTACAGACTGGA [SEQ ID NO: 9] | ACAAAAACC |
| 16 | CACAGTG | CTACAGACTGGA [SEQ ID NO: 9] | ACAAAAACC |
| 17 | CACAGTG | CTACAGACTGGA [SEQ ID NO: 9] | CAAAACCC |
| 18 | CACAGTG | CTACAGACTGGA [SEQ ID NO: 9] | ACAAAAACC |
| 19 | CACAATG | CTACAGACTGGA [SEQ ID NO: 9] | ACAAAAACC |
| 20 | CACAGCG | CTACAGACTGGA [SEQ ID NO: 9] | ACAAAAACC |
| | Part III. Efficiency: LOW (~1% or less of High) | | |
| 21 | TACAGTG | CTACAGACTGGA [SEQ ID NO: 9] | ACAAAAACC |
| 22 | GACAGTG | CTACAGACTGGA [SEQ ID NO: 9] | ACAAAAACC |
| 23 | CATAGTG | CTACAGACTGGA [SEQ ID NO: 9] | ACAAAAACC |
| 24 | CACAATG | CTACAGACTGGA [SEQ ID NO: 9] | ACAAAAACC |
| 25 | CACAGTG | CTACAGACTGGA [SEQ ID NO: 9] | ACAAAAACC |
| 26 | CAGAGTG | CTCCAGGGCTGA [SEQ ID NO: 10] | ACAAAAACC |

TABLE 1A-continued

EXEMPLARY RECOMBINATION SIGNAL SEQUENCES (12 NUCLEOTIDE SPACER)

| | Heptamer H12 | Spacer S12 | Nonamer N12 |
|---|---|---|---|
| 27 | CACAGTG | CTCCAGGGCTGA [SEQ ID NO: 10] | AAAAAAACC |
| 28 | CTCAGTG | CTCCAGGGCTGA [SEQ ID NO: 10] | ACAAAAACC |

TABLE 1B

EXEMPLARY RECOMBINATION SIGNAL SEQUENCES (23 NUCLEOTIDE SPACER)

| | Heptamer H23 | Spacer S23 | Nonamer N23 | Ref.* |
|---|---|---|---|---|
| | Part I. Efficiency: HIGH | | | |
| 1 | CACAGTG | GTAGTACTCCACTGTCTGGCTGT [SEQ ID NO: 12] | ACAAAAACC | 4 |
| 2 | CACAGTG | GTAGTACTCCACTGTCTGGCTGT [SEQ ID NO: 12] | ACAAAAACC | 3 |
| 3 | CACAGTG | GTAGTACTCCACTGTCTGGGTGT [SEQ ID NO: 12] | ACAAAAACC | 1 |
| 4 | CACAGTG | TTGCAACCACATCCTGAGTGTGT [SEQ ID NO: 14] | ACAAAAACC | 2 |
| 5 | CACAGTG | GTAGTACTCCACTGTCTGGCTGT [SEQ ID NO: 12] | ACAAAAACC | 2 |
| 6 | CACAGTG | ACGGAGATAAAGGAGGAAGCAGG [SEQ ID NO: 15] | ACAAAAACC | 2 |
| 7 | CACAGTG | GCCGGGCCCCGCGGCCCGGCGGC [SEQ ID NO: 13] | ACAAAAACC | 5 |
| | Part II. Efficiency: MEDIUM (~10-20% of High) | | | |
| 8 | CACAGTG | GTAGTACTCCACTGTCTGGCTGT [SEQ ID NO: 12] | ACAAAAACC | 3 |
| 9 | CACAGTG | GTAGTACTCCACTGTCTGGCTGT [SEQ ID NO: 12] | ACAAAAACC | 3 |
| 10 | CACAGTG | GTAGTACTCCACTGTCTGGCTGT [SEQ ID NO: 12] | ACAAAAACC | 3 |
| 11 | CACAATG | GTAGTACTCCACTGTCTGGCTGT [SEQ ID NO: 12] | ACAAAAACC | 3 |
| 12 | CACAGCG | GTAGTACTCCACTGTCTGGCTGT [SEQ ID NO: 12] | ACAAAAACC | 3 |
| 13 | CACAGTA | GTAGTACTCCACTGTCTGGCTGT [SEQ ID NO: 12] | ACAAAAACC | 3 |
| 14 | CACAGTG | GTAGTACTCCACTGTCTGGCTGT [SEQ ID NO: 12] | ACAATAACC | 3 |
| 15 | CACAGTG | GTAGTACTCCACTGTCTGGCTGT [SEQ ID NO: 12] | ACAAGAACC | 3 |
| 16 | CACAGTG | GTAGTACTCCACTGTCTGGCTGT [SEQ ID NO: 12] | ACACGAACC | 3 |
| 17 | CACAGTG | GTAGTACTCCACTGTCTGGCTGT [SEQ ID NO: 12] | ACAAAAACC | 3 |
| 18 | CACAGTG | GTAGTACTCCACTGTCTGGCTGT [SEQ ID NO: 12] | ACACGAACC | 3 |
| 19 | CACAATG | GTAGTACTCCACTGTCTGGCTGT [SEQ ID NO: 12] | ACAAAAACC | 3 |
| 20 | CACAGCG | GTAGTACTCCACTGTCTGGCTGT [SEQ ID NO: 12] | ACAAAAACC | 3 |
| | Part III. Efficiency: LOW (~1% or less of High) | | | |
| 21 | CACAGTA | GTAGTACTCCACTGTCTGGCTGT [SEQ ID NO: 12] | ACAAAAACC | 3 |
| 22 | CACAGTG | GTAGTACTCCACTGTCTGGCTGT [SEQ ID NO: 12] | ACAAAAACC | 3 |
| 23 | CACAATG | GTAGTACTCCACTGTCTGGCTGT [SEQ ID NO: 12] | ACAAAAACC | 3 |
| 24 | CATAGTG | GTAGTACTCCACTGTCTGGCTGT [SEQ ID NO: 12] | ACAAAAACC | 3 |
| 25 | CACAGTG | GTAGTACTCCACTGTCTGGCTGT | TGTCTCTGA | 3 |
| | | [SEQ ID NO: 12] | | |
| 26 | CACAGTG | GTAGTACTCCACTGTCTGGGTGT [SEQ ID NO: 12] | ACAAAAACC | 1 |

TABLE 1B-continued

EXEMPLARY RECOMBINATION SIGNAL SEQUENCES (23 NUCLEOTIDE SPACER)

| | Heptamer H23 | Spacer S23 | Nonamer N23 | Ref.* |
|---|---|---|---|---|
| 27 | CACAGTG | GTAGTACTCCACTGTCTGGGTGT [SEQ ID NO: 12] | ACAAAAACC | 1 |
| 28 | CACAGTG | GTAGTACTCCACTGTCTGGGTGT [SEQ ID NO: 12] | ACAAAAACC | 1 |

*(1) Akamatsu, 1994, ibid; (2) Cowell, 2004, ibid; (3) Hesse, 1989 ibid; (4) Lee, 2003 ibid; (5) Nadel, 1998, ibid.

Positioning the RSSs within the Protein Coding Sequence

In accordance with the present invention, the RSSs are positioned at a predetermined (targeted) location or locations within the target protein coding sequence.

While various regions of the target protein may be selected as a targeted location for the introduction of sequence diversity, it is generally preferred that the targeted location is not within a region of the protein important for protein folding and/or adoption of the protein's functional conformation, although this does remain an alternative option. Selection of appropriate target locations can be readily made by one skilled in the art with reference to the target protein's known or predicted structure. For example, the crystal structures of many proteins are known and available, for example, from sources such as the Protein Data Bank (PDB) maintained by the Research Collaboratory for Structural Bioinformatics (RCSB). In addition, many resources are publicly available allowing for the prediction of secondary and/or tertiary structure of a known protein, for example, RaptorX (University of Chicago), ESyPred3D (University of Namur), HHPred (Max Planck Institute for Experimental Biology), Phyre2 (Imperial College, London), ProtInfo ABCM, BAGHEERATH-H (Ministry of Science and Technology, India, Department of Biotechnology), Rosetta@home (University of Washington), JPred (University of Dundee), NetSurfP (Centre for Biological Sequence Analysis), PredictProtein, PSIPred (UCL), SymPred, and the like.

In accordance with certain embodiments, the targeted location is selected such that it is within a non-conformational region of the protein (i.e. a region of the protein that is not important for folding and/or adoption of the protein's functional conformation). In some embodiments, the targeted location is selected such that it is within an externally exposed region of the protein.

In certain embodiments in which the target protein is a ligand-binding protein, the targeted location is selected such that it is within or proximal to a ligand-binding domain, or in a region that otherwise impacts on ligand binding by the protein.

In some embodiments, the targeted location is selected such that it is within or proximal to a loop region, for example, an externally exposed loop. Loop regions of a target protein can be readily identified with reference to the target protein's known or predicted structure. In addition, various programs are available that allow loop regions of a protein to be identified based on the known amino acid sequence (for example, ArchPred, FREAD, ModLoop, RAPPER and SuperLooper). In some embodiments, the targeted location is selected such that it is within an externally exposed loop. In certain embodiments in which the targeted location is within a loop region of the protein, the location is selected such that it is substantially within the central portion of the loop.

For example, the 10$^{th}$ domain of FN3 ($^{10}$FN3) is known to comprise three loops at one end of a β-sandwich, which can be sequence diversified to provide binding to a target ligand. Specifically, the three loops of $^{10}$FN3 that are analogous to the antigen binding loops of the IgG heavy chain are defined by amino acid residues 21-31, 51-56 and 76-88. Each of these loops is thus a suitable target for introduction of sequence diversity according to the present methods. The second loop is only 6 amino acids in length and as such may be extended, for example by about 10 to 16 amino acids, at the same time as, or in addition to, introducing sequence diversity.

In immunoglobulins, both CDR1 and CDR2 are loop regions which can be readily identified and are suitable target locations for introduction of sequence diversity using the methods described herein. CDR3 is also a loop region of immunoglobulins that is a suitable target locations for introduction of sequence diversity in certain embodiments.

In those embodiments in which the targeted location is within a loop region of the protein, it is contemplated that the RSSs can be located at various positions within the loop. For example, one or both of the RSSs in a complementary pair may be positioned at or proximal to the start (i.e. the N-terminal, or 5', side) of the loop, or one or both of the RSSs may be positioned at or proximal to the end (i.e. the C-terminal, or 3', side) of the loop, or one or both of the RSSs may be positioned proximal to the centre point of the loop. Other combinations for the positioning of the RSSs will be readily apparent to the skilled worker and are included. In one embodiment, the RSSs are located within a loop region of the target protein and at least one of the RSSs is positioned proximal to the centre point of the loop.

As noted above, in certain embodiments, complementary pairs of RSSs are introduced into the coding sequence for the target protein, in which the first RSS of the pair is capable of functional recombination with the second RSS of the pair. In accordance with these embodiments, the two RSSs of the complementary pair are separated by an intervening sequence of about 100 bp or more in length. The nucleotide sequence of the intervening sequence is not critical to the invention and may be comprised of a sequence heterologous to the coding sequence or it may be comprised of part of the coding sequence. For example, in certain embodiments, the complementary pair of RSSs are introduced individually into the coding sequence such that part of the coding sequence forms the intervening sequence. In other embodiments, the complementary pair of RSSs is introduced together with a heterologous intervening sequence into the coding sequence as a "cassette." The nucleotide sequence of the intervening sequence can accommodate a wide variety of sequences, including for example some selectable markers, some promoters and other regulatory elements such as polyadenylation signals, but preferably does not include insulator-like elements as exemplified by cHS4 and AAV1.

In certain embodiments, the intervening sequence comprises an expression cassette, for example containing a promoter and optionally poly(A) sequences that drive expression of a marker such as GFP or a cell surface marker such that recombination can be monitored, or a selectable marker such as a drug resistance gene such that the cell can be maintained in the un-recombined state via drug selection.

Regardless of the composition of the intervening sequence, it is preferably selected to be at least 100 bp in length, for example, at least 110 bp, at least 120 bp, at least 130 bp, at least 140 bp, at least 150 bp, but may range up to several kilobases in size, for example up to about 5 kb. One skilled in the art will understand that the exact upper limit for the intervening sequence will be dictated by the limitation of the vector system used. In certain embodiments, the intervening sequence is selected to be between about 100 bp and 5 kb, for example, between about 150 bp and 5 kb, between about 180 bp and 5 kb, between about 180 bp and 4 kb, between about 180 bp and 3 kb or between about 180 bp and 2 kb. In some embodiments, the intervening sequence is selected to be between about 100 bp and 1.5 kb, for example, between about 110 bp and 1.5 kb, between about 120 bp and 1.5 kb, between about 130 bp and 1.5 kb, between 140 bp and 1.5 kb, or between 150 bp and 1.5 kb. In some embodiments, the intervening sequence is selected to be between about 180 bp and 1.9 kb, for example, between about 180 bp and 1.8 kb, between about 180 bp and 1.7 kb, between about 180 bp and 1.6 kb, or between 180 bp and 1.5 kb. Other exemplary embodiments include intervening sequences of between about 190 bp and 1.5 kb, between about 200 bp and 1.5 kb, between about 210 bp and 1.5 kb, between about 220 bp and 1.5 kb, between about 230 bp and 1.5 kb, between about 240 bp and 1.5 kb, and between about 250 bp and 1.5 kb.

In certain embodiments, flanking sequences are included adjacent to the heptamer of the RSS. In accordance with this embodiment, the flanking sequences may be chosen to have a defined sequence (for example, to specifically encode one or more amino acids) or they may have a random sequence. In some embodiments, the flanking sequences may be selected to introduce certain characteristics at the site of insertion, for example, through the addition of one or more charged amino acids, histidine residues or cysteine residues. In certain embodiments, the flanking sequence may comprise a duplication of a part of the sequence into which the RSSs are to be introduced. In some embodiments, the position and length of the flanking sequences are selected to bias diversification towards one side of the insertion point, or to provide a larger loop size prior to diversification.

When used, the length of the flanking sequence is selected such that it does not interfere with the structural integrity of the target protein. In certain embodiments in which flanking sequences accompany the RSSs and are introduced into a loop region of the target protein, the flanking sequence(s) are selected such that their introduction into the loop results in an increase in loop length of about 150% or less, for example, 100% or less, or 50% or less. In some embodiments, the flanking sequence(s) are selected such that their introduction into the loop results in an increase in loop length of 0% to about 50%, for example, between about 1% and about 50%.

In some embodiments in which the targeted location is within a small loop of a protein, flanking sequences may be used in conjunction with the RSSs to ensure that the majority of the products include a loop that retains a minimal length once sequence diversification has taken place. In certain embodiments the RSSs are inserted into a region of the protein such that sequences are deleted resulting in a net smaller loop size than the parent molecule, for example, a decrease in loop length of between about 1% and about 50%.

The methods of the present invention contemplate the introduction of one, or more than one, complementary pairs of RSSs into the coding sequence for a target protein. In certain embodiments, one complementary pair of RSSs is introduced into the coding sequence in order to generate sequence diversity at a targeted location in the protein. In some embodiments, two complementary pairs of RSSs are introduced into the coding sequence in order to generate sequence diversity at more than one targeted location in the protein. In certain embodiments in which two pairs of RSSs are used, they may be oriented such that recombination between the distal members of the two pairs cannot occur (i.e. the 5' RSS of the first pair and the 3' RSS of the second pair are both 23 bp RSSs or are both 12 bp RSSs).

In certain embodiments, two or more complementary pairs of RSSs are introduced into the coding sequence in order to generate sequence diversity at more than one targeted location in the protein.

In certain embodiments, a complementary pair of RSSs may be introduced into the coding sequence as a "cassette" that includes a heterologous intervening sequence spacing the two RSSs apart, such that upon recombination at the RSSs, the RSSs and the heterologous sequence are deleted and sequence diversity is introduced into the coding sequence at the site of recombination.

In certain embodiments, a complementary pair of RSSs may be introduced into the coding sequence as a "cassette" that includes a heterologous intervening sequence spacing the two RSSs apart as well as flanking sequences on the other side of one or both of the RSSs, such that upon recombination at the RSSs, the RSSs and the heterologous sequence are deleted and new sequences (from the flanking sequences) are added, in addition to sequence diversity being introduced into the coding sequence at the site of recombination.

The RSSs can be introduced into the polynucleotide by standard genetic engineering techniques such as those described in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.).

Additional Coding Sequences

In accordance with certain embodiments of the invention, the polynucleotide may comprise additional coding sequences and thus may encode a fusion protein that comprises the target protein fused to another peptide or polypeptide that provides additional functionality to the protein. Examples of peptides and polypeptides that provide additional functionality include, but are not limited to, secretory signal sequences, leader sequences, plasma membrane anchor domain polypeptides such as hydrophobic transmembrane domains (see, for example, Heuck et al., 2002, *Cell Biochem. Biophys.* 36:89; Sadlish et al., 2002, *Biochem J.* 364:777; Phoenix et al., 2002, *Mol. Membr. Biol.* 19:1; Minke et al., 2002, *Physiol. Rev.* 82:429) or glycosylphosphatidylinositol attachment sites ("glypiation" sites) (see, for example, Chatterjee et al., 2001, *Cell Mol. Life Sci.* 58:1969; Hooper, 2001, *Proteomics* 1:748, and Spiro, 2002, *Glycobiol.* 12:43R), and other structural features that assist in localizing the fusion protein to the cell surface such as protein-protein association domains, lipid association domains, glycolipid association domains and proteoglycan association domains, for example, cell surface receptor binding domains, extracellular matrix binding domains, and lipid raft-associating domains (see, for example, Browman et al., 2007, *Trends Cell Biol* 17:394-402; Harder, T., 2004, *Curr Opin Immunol* 16:353-9; Hayashi, T. and Su, T. P., 2005, *Life Sci* 77:1612-24; Holowka, D. and Baird, B., 2001, *Semin Immunol* 13:99-105, and Wollscheid et al., 2004, *Subcell Biochem* 37:121-52).

In some embodiments, the additional coding sequences may encode a "tag" to facilitate downstream screening and/or purification of the target protein. Examples of such heterologous nucleic acid sequences include, but are not limited to, affinity tags such as metal-affinity tags, histidine tags, protein A, glutathione S transferase, Glu-Glu affinity tag, substance P, FLAG peptide (Hopp et al., 1988, *Biotechnology* 6:1204), streptavidin binding peptide, or other antigenic epitope or binding domain (see, in general, Ford et al., 1991, *Protein Expression and Purification* 2:95). Nucleic acid sequences encoding affinity tags are available from commercial suppliers (for example, Pharmacia Biotech, Piscataway, N.J.).

In some embodiments, the polynucleotide comprises additional coding sequences that encode a plasma membrane anchor domain. For example, a transmembrane polypeptide domain typically comprising a membrane spanning domain (such as an [α]-helical domain) which includes a hydrophobic region capable of energetically favorable interaction with the phospholipid fatty acyl tails that form the interior of the plasma membrane bilayer, or a membrane-inserting domain polypeptide typically comprising a membrane-inserting domain which includes a hydrophobic region capable of energetically favorable interaction with the phospholipid fatty acyl tails that form the interior of the plasma membrane bilayer but that may not span the entire membrane. Well known examples of transmembrane proteins having one or more transmembrane polypeptide domains include members of the integrin family, CD44, glycophorin, MHC Class I and II glycoproteins, EGF receptor, G protein coupled receptor (GPCR) family, receptor tyrosine kinases (such as insulin-like growth factor 1 receptor (IGFR) and platelet-derived growth factor receptor (PDGFR)), porin family and other transmembrane proteins. Certain embodiments of the invention contemplate using a portion of a transmembrane polypeptide domain such as a truncated polypeptide having membrane-inserting characteristics as may be determined according to standard and well known methodologies.

In some embodiments of the invention, the polynucleotide comprises additional coding sequences that encode a specific protein-protein association domain, for example a protein-protein association domain that is capable of specifically associating with an extracellularly disposed region of a cell surface protein or glycoprotein. In certain embodiments, the protein-protein association domain may result in an association that is initiated intracellularly, for instance, concomitant with the synthesis, processing, folding, assembly, transport and/or export to the cell surface of a cell surface protein. In some embodiments, the protein-protein association domain is known to associate with another cell surface protein that is membrane anchored and exteriorly disposed on a cell surface. Non-limiting examples of such domains include, RGD-containing polypeptides including those that are capable of integrin binding (see, for example, Heckmann, D. and Kessler, H., 2007, *Methods Enzymol* 426:463-503 and Takada et al., 2007, *Genome Biol* 8:215).

In some embodiments, the polynucleotide comprises a secretory signal sequence that encodes a secretory peptide. A secretory peptide is an amino acid sequence that acts to direct the secretion of a mature polypeptide or protein from a cell and is generally characterized by a core of hydrophobic amino acids. Secretory peptides are typically, but not exclusively, positioned at the amino termini of newly synthesized proteins. The secretory peptide may be cleaved from the mature protein during secretion and may, therefore, contain processing sites that allow cleavage of the signal peptide from the mature protein as it passes through the secretory pathway. Examples of secretory peptides are known in the art and include, but are not limited to, alpha mating factor leader sequence, the secretory pre-peptide of IL-15, the tissue Plasminogen Activator (tPA) secretory leader peptide, transferrin (Tf) signal sequence, IgE secretory peptides, IgHV and IgKV signal peptides and GM-CSF secretory peptides.

In certain embodiments, sequences encoding a transmembrane domain are included in the polynucleotide to provide surface expression of the variant protein. In some embodiments, the variant protein is cloned in-frame with a selectable marker to allow for the selection of productive in-frame products. In some embodiments, the polynucleotide comprises sequences encoding a transmembrane domain, a selectable marker and an enzyme cleavage site prior to the selectable marker to allow for cleavage of the variant protein from the transmembrane domain.

Additional sequences, when used, can be included in the polynucleotide by standard genetic engineering techniques such as those described in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.).

Vectors

Certain embodiments of the invention relate to vectors comprising the polynucleotide encoding the target protein, and also vectors comprising nucleic acid sequences encoding RAG-1, RAG-2 or TdT (or functional fragments or variants thereof), and vectors comprising regulatory constructs such as siRNA regulators of RAG-1, RAG-2 and/or TdT expression. A wide variety of suitable vectors are known in the art and may be employed as described or according to conventional procedures, including modifications, as described for example in Sambrook et al., ibid.; Ausubel et al., ibid, and elsewhere.

One skilled in the art will appreciate that the precise vector used is not critical to the instant invention and suitable vectors can be readily selected by the skilled person. Examples of expression vectors and cloning vehicles include, but are not limited to, viral particles, baculovirus, phage, plasmids, phagemids, cosmids, fosmids, bacterial artificial chromosomes, retrovirus vectors, viral DNA (for example, vaccinia, adenovirus, foul pox virus, pseudorabies and derivatives of SV40), P1-based artificial chromosomes, yeast plasmids, yeast artificial chromosomes, and other known vectors specific for specific host cells of interest.

Large numbers of suitable vectors are known to those of skill in the art, and many are commercially available. Exemplary commercially available vectors include the bacterial vectors: pcDNA (Invitrogen), pQE vectors (Qiagen), pBLUESCRIPT™ plasmids, pNH vectors, lambda-ZAP vectors (Stratagene); ptrc99a, pKK223-3, pDR540, and pRIT2T (Pharmacia); and the eukaryotic vectors: pXT1, pSGS (Stratagene), pSVK3, pBPV, pMSG and pSVLSV40 (Pharmacia). Other vectors include, for example, adenovirus (Ad) vectors (such as, vectors based on non-replicating Ad5, or replication-competent Ad4 and Ad7 vectors), adeno-associated virus (AAV) vectors (such as, AAV type 5), alphavirus vectors (such as, Venezuelan equine encephalitis virus (VEE), sindbis virus (SIN), semliki forest virus (SFV), and VEE-SIN chimeras), herpes virus vectors, measles virus vectors, pox virus vectors (such as, vaccinia virus, modified vaccinia virus Ankara (MVA), NYVAC (derived from the Copenhagen strain of vaccinia), and avipox vectors: canarypox (ALVAC) and fowlpox (FPV) vectors), and vesicular stomatitis virus vectors. Other suitable plasmids and vectors are known in the art and can readily be selected by the skilled worker. In accordance with various embodiments of the invention, either low copy number or high copy number vectors may be employed.

One skilled in the art will understand that the vector may further include regulatory elements, such as transcriptional elements, required for efficient transcription of the DNA sequence encoding the target protein. Examples of regulatory elements that can be incorporated into the vector include, but are not limited to, promoters, enhancers, terminators, alpha-factors, ribosome binding sites and polyadenylation signals. In various embodiments, the present invention, therefore, contemplates vectors comprising one or more regulatory elements operatively linked to a polynucleotide encoding the target protein.

One skilled in the art will appreciate that selection of suitable regulatory elements is dependent on the host cell chosen for expression of the encoded protein and that such regulatory elements may be derived from a variety of sources, including bacterial, fungal, viral, mammalian or insect genes.

Mammalian expression vectors, for example, may comprise one or more of an origin of replication, any necessary ribosome binding sites, a polyadenylation site, splice donor and acceptor sites, transcriptional termination sequences, and 5' flanking non-transcribed sequences. DNA sequences derived from the SV40 splice and polyadenylation sites, for example, may be used to provide the required non-transcribed genetic elements. Eukaryotic expression vectors may also contain one or more enhancers to increase expression levels of the protein. Enhancers are cis-acting elements of DNA, usually from about 10 to about 300 bp in length that act on a promoter to increase its transcription. Examples include, but are not limited to, the SV40 enhancer on the late side of the replication origin by 100 to 270, the cytomegalovirus early promoter enhancer, the polyoma enhancer on the late side of the replication origin and the adenovirus enhancers.

Examples of typical promoters include, but are not limited to, the bacterial promoters: lad, lacZ, T3, T7, gpt, lambda $P_R$, $P_L$ and trp; and the eukaryotic promoters: CMV immediate early, HSV thymidine kinase, early SV40, late SV40, LTRs from retrovirus and mouse metallothionein-I. Promoter regions can also be selected from a desired gene using chloramphenicol transferase (CAT) vectors or other vectors with selectable markers.

In certain embodiments the vector comprises an expression control sequence which is a "regulated promoter," which may be a promoter as provided herein or may be a repressor binding site, an activator binding site or other regulatory sequence that controls expression of a nucleic acid sequence. In some embodiments, the vector comprises a tightly regulated promoter that is specifically inducible and that permits little or no transcription of nucleic acid sequences under its control in the absence of an induction signal. Examples of such tightly regulated promoters are known to those familiar with the art and described, for example, in Guzman et al. (1995, *J. Bacteriol.* 177:4121), Carra et al. (1993, *EMBO J.* 12:35), Mayer (1995, *Gene* 163:41), Haldimann et al. (1998, *J. Bacteriol.* 180:1277), Lutz et al. (1997, *Nuc. Ac. Res.* 25:1203), Allgood et al. (1997, *Curr. Opin. Biotechnol.* 8:474) and Makrides (1996, *Microbiol. Rev.* 60:512). In other embodiments of the invention, the vector comprises a regulated promoter that is inducible but that may not be tightly regulated. Inducible systems that include regulated promoters include, for example, the Tet system or other similar expression-regulating components, such as the Tet/on and Tet/off system (Clontech Inc., Palo Alto, Calif.), the Regulated Mammalian Expression system (Promega, Madison, Wis.), and the Gene-Switch System (Invitrogen Life Technologies, Carlsbad, Calif.).

In certain embodiments, the vector comprises a promoter that is not a regulated promoter; such a promoter may include, for example, a constitutive promoter such as an insect polyhedrin promoter.

In addition, vectors may contain one or more selectable marker genes to provide a phenotypic trait for selection of transformed host cells. Such selectable markers include for example genes encoding dihydrofolate reductase or genes conferring neomycin resistance, puromycin resistance, or hygromycin resistance, or the use of xanthine-guanine phosphoribosyltransferase in eukaryotic host cells, genes conferring ampicillin, chloramphenicol, erythromycin, kanamycin, neomycin or tetracycline resistance in bacterial host cells, and the *S. cerevisiae* TRP1 gene. Promoter regions can be selected from any desired gene using chloramphenicol transferase (CAT) vectors or other vectors with selectable markers. Selectable markers can also include biosynthetic genes, such as those in the histidine, tryptophan and leucine biosynthetic pathways.

In certain embodiments, the vector can have two replication systems to allow it to be maintained in two organisms, for example in mammalian or insect cells for expression and in a prokaryotic host for cloning and amplification.

Also contemplated are replicating and non-replicating episomal vectors for transient expression. Replicating vectors contain origin sequences that promote plasmid replication in the presence of the appropriate trans factors. The SV40 and polyoma origins and respective T-antigens are non-limiting examples. Also contemplated are stably maintained episomal expression vectors. Episomal plasmids are usually based on sequences from DNA viruses, such as BK virus, bovine papilloma virus 1 and Epstein-Barr virus (see, for example, Van Craenenbroeck, K., et al., 2000, *Eur. J. Biochem.* 267:5665-5678). These vectors contain a viral origin of DNA replication and a viral early gene(s), the product of which activates the viral origin and thus allows the episome to reside in the transfected host cell line in a well-controlled manner. Episomal vectors are plasmid constructions that replicate in both eukaryotic and prokaryotic cells and can therefore also be "shuttled" from one host cell system to another.

In some embodiments the plasmid selected is a plasmid that can be integrated into the host chromosome. Integration can occur by random methods or can be targeted. In some embodiments in which integrating expression vectors are used, the expression vector can contain at least one sequence homologous to the host cell genome, for example, two homologous sequences which flank the expression construct. The integrating vector can thus be directed to a specific locus in the host cell by selecting the appropriate homologous sequence for inclusion in the vector. Constructs for integrating vectors are well known in the art. Alternatively, the use of recombination systems like Cre/Lox and Flp/Frt can be used to target integration. Other methods utilizing zinc-finger proteins as developed by Sangamo Inc. (Richmond, Calif.) provide another approach to targeting vector integration.

In certain embodiments, the methods described herein employ a vector or recombination system that allows for stable integration of the polynucleotide into the host cell genome. In some embodiments, the methods described herein employ a vector or recombination system that allows for stable integration of the polynucleotide into the host cell genome as a single copy.

In certain embodiments of the invention, the vector employed is a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumour virus. Suitable promoters for inclusion in viral vectors include, but are not limited to, the retroviral LTR; the SV40 promoter; and the human cytomegalovirus (CMV) promoter described in Miller, et al. (1989, *Biotechniques* 7:980-990), or other suitable promoter (for example, cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art, and may be from among either regulated promoters or promoters as described above.

In those embodiments that employ a retroviral plasmid vector, the vector is used to transduce packaging cell lines to form producer cell lines. Examples of packaging cells which may be transfected include, but are not limited to, the PE501, PA317, [psi]-2, [psi]-AM, PA12, T19-14X, VT-19-17-H2, [psi]CRE, [psi]CRIP, GP+E-86, GP+envAm12, and DAN cell lines as described in Miller (1990, *Human Gene Therapy*, 7:5-14). The packaging cells may be transduced with the vector using various means known in the art such as, for example, electroporation, the use of liposomes, and CaPO$_4$ precipitation. The producer cell line generates infectious retroviral vector particles which include the polynucleotide encoding the protein. Such retroviral vector particles then may be employed to transduce eukaryotic cells, either in vitro or in vivo, and the transduced eukaryotic cells will express the polynucleotide encoding the protein. Eukaryotic cells which may be transduced include, but are not limited to, embryonic stem cells, embryonic carcinoma cells, hematopoietic stem cells, hepatocytes, fibroblasts, myoblasts, keratinocytes, endothelial cells, and bronchial epithelial cells.

The appropriate DNA or polynucleotide sequences can be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Sambrook et al., ibid.; Ausubel et al., ibid., and elsewhere.

The vector can be introduced into a suitable host cell by one of a variety of methods known in the art. Such methods can be found generally described in Ausubel et al. (ibid.) and include, for example, stable or transient transfection, lipofection, electroporation, the use of polyethylenimine (PEI) and infection with recombinant viral vectors. One skilled in the art will understand that selection of the appropriate host cell for expression of the target protein will be dependent upon the vector chosen. The polynucleotide may stably integrate into the genome of the host cell (for example, with retroviral introduction) or may exist either transiently or stably in the cytoplasm (for example, through the use of traditional plasmids or vectors, utilizing standard regulatory sequences, selection markers, and the like, as described above).

Host Cells

In accordance with the present invention, the host cell employed in the methods described herein is a host cell capable of utilizing recombination signals and undergoing RAG-1/RAG-2 mediated recombination. Accordingly, host cells suitable for use in the methods described herein express or can be engineered to express at least RAG-1 and RAG-2 or functional fragments thereof that allow the host cell to utilize recombination signals and undergo RAG-1/RAG-2 mediated recombination.

In certain embodiments, cell lines to be used as host cells may additionally contain a functional TdT gene. TdT is encoded by a single gene and expresses a nuclear enzyme whose expression in vivo is restricted to lymphoid progenitor cells. TdT has, however, been expressed in non-lymphoid cells and shown to participate in V(D)J recombination using retroviral and transient recombination substrates. TdT has been shown to be expressed as a number of different splice variants, including long form and short form. Certain embodiments of the invention contemplate the use of different isoforms of TdT.

TdT has also been shown to have a 3' to 5' exonuclease activity and the different isoforms of TdT have been shown to have different amounts of exonuclease activity. TdT exonuclease activity can be modulated by substitutions at the conserved aspartic acid residue in the exonuclease motif. In addition, expression of both isoforms was shown to modulate nuclease activity. TdT is highly conserved among species. While mice have two isoforms both human and bovine have three isoforms. In certain embodiments, TdT activity in the host cell can be modulated by altering the levels of TdT in the cell. In some embodiments, mutant forms of TdT or different combinations of isoforms may be used in the host cell to generate coding joints with different extents of deletion and addition.

Cell lines may in certain embodiments be pre-B cells or pre-T cells that express RAG-1 and RAG-2, and optionally TdT, proteins. Such pre-B and pre-T cells may be capable of being induced to express RAG-1 and/or RAG-2, and optionally TdT, or alternatively, may constitutively express RAG-1 and/or RAG-2, and optionally TdT, but can be modified to substantially impair the expression of one, two or all three of these enzymes.

In some embodiments, the cell lines are non-immune cells that have been transformed with genes encoding each of RAG-1 and RAG-2, and optionally TdT (see for example, for RAG-1/2: Schatz, D G et al., 1989, *Cell* 59:1035-48; Oettinger, M. A. et al., 1990, *Science* 248:1517-23; for TdT: Thai, T. H. & Kearney, J. F., 2004, *J Immunol* 173:4009-19; Koiwai, O. et al., 1987, *Biochem Biophys Res Commun* 144:185-90; Peterson, R. C. et al., 1984, *Proc Natl Acad Sci USA* 81:4363-7; for transfection of a host cell with all three of RAG-1, RAG-2 and TdT: U.S. Pat. No. 5,756,323). One skilled in the art can readily select an appropriate non-immune host cell. Examples of host cells include, but are not limited to, yeast and mammalian cells. Specific non-limiting examples include *Saccharomyces cerevisiae, Pichia pastoris*, green African monkey kidney (COS) cells, NIH 3T3 cells, Chinese hamster ovary (CHO) cells, BHK cells, human embryonic kidney (HEK 293) cells, Huh7.5 human hepatoma cells, Hep G2 human hepatoma cells, Hep 3B human hepatoma cells, HeLa cells and the like.

These and other host cells may be used according to contemplated embodiments of the present invention. For example, expression of RAG-1 and/or RAG-2 has been observed in mature B-cells in vivo and in vitro (Maes et al., 2000, *J Immunol.* 165:703; Hikida et al., 1998, *J Exp Med.* 187:795; Casillas et al., 1995, *Mol Immunol.* 32:167; Rathbun et al., 1993, *Int Immunol.* 5:997, Hikida et al., 1996, *Science* 274:2092).

RAG-1 and RAG-2 have also been shown to be expressed in mature T-cell lines including Jurkat T-cells. CEM cells have been shown to have V(D)J recombination activity using extrachromosomal substrates (Gauss et al. 1998, *Eur J Immunol.* 28:351). Treatment of wild-type Jurkat T cells with chemical inhibitors of signaling components revealed that inhibition of Src family kinases using PP2, FK506 etc. overcame the repression of RAG-1 and resulted in increased RAG-1 expression. Mature T-cells have also been shown to reactivate recombination with treatment of anti-CD3/IL7 (Lantelme et al., 2008, *Mol Immunol.* 45:328).

Tumor cells of non-lymphoid origin have also been shown to express RAG-1 and RAG-2 (Zheng et al., 2007, *Mol Immunol.* 44: 2221, Chen et al., 2007, *Faseb J.* 21:2931). Accordingly, in certain embodiments, these cells may also be suitable for use as host cells in the presently described methods. According to other embodiments that are contemplated herein, reactivation of V(D)J recombination would provide another approach to generating a suitable host cell with inducible recombinase expression.

Use of other host cells is contemplated according to certain embodiments, which may vary depending on the particular mammalian genes that are employed or for other reasons, including a human cell, a non-human primate cell, a camelid cell, a hamster cell, a mouse cell, a rat cell, a rabbit cell, a canine cell, a feline cell, an equine cell, a bovine cell and an ovine cell.

In certain embodiments, the host cell lines can also include added genetic elements that provide useful functionality. For example, Invitrogen provides a flp-in system in which the Frt recombination signal is integrated into different host cell lines (3T3, BHK, CHO, CV-1, 293). Equivalent cell lines incorporating LoxP sites or other sites for targeting integration can be used. Invitrogen also provides tet inducible systems (T-Rex) for 293 or HeLa cell lines. Other inducible systems are also available.

Alternatively, only one of the RAG-1 or RAG-2 genes may be stably integrated into a host cell, and the other gene can be introduced by transformation to regulate recombination. For example, a cell line that is stably transformed with TdT and RAG-2 would be recombinationally silent. Upon transient transformation with RAG-1, or viral infection with RAG-1, the cell lines would become recombinationally active. The skilled person will appreciate from these illustrative examples that other similar approaches may be used to control the onset of recombination in a host cell.

Another approach may be to use specific small interfering RNA (siRNA) to repress the expression in a host cell of RAG-1 and/or RAG-2 bp RNA interference (RNAi) (including specific siRNAs the biosynthesis of which within a cell may be directed by introduced encoding DNA vectors having regulatory elements for controlling siRNA production), and then to relieve such repression when it is desired to induce recombination. For instance, in certain such embodiments a cell line in which active RAG-1 and/or RAG-2 specific siRNA expression is present will be recombinationally silent. Activation of recombination occurs when RAG-1 and/or RAG-2 specific siRNA expression is shut off or repressed. Regulation of such siRNA expression may be achieved using inducible systems like the Tet system or other similar expression-regulating components. These include the Tet/on and Tet/off system (Clontech Inc., Palo Alto, Calif.), the Regulated Mammalian Expression system (Promega, Madison, Wis.), and the GeneSwitch System (Invitrogen Life Technologies, Carlsbad, Calif.). Alternatively, host cells may be transformed with an expression vector that encodes a repressing protein that prevents transcription of the inhibiting RNA.

In yet another alternative embodiment according to which RAG-1 and/or RAG-2 specific siRNA expression may regulate the recombination competence of the host cell, deletion of the introduced siRNA encoding sequences by use of the Cre/Lox recombinase system (see, for example, Sauer, 1998, *Methods* 14:381; Kaczmarczyk et al., 2001, *Nucleic Acids Res* 29:E56; Sauer, 2002, *Endocrine* 19:221; Kondo et al., 2003, *Nucleic Acids Res* 31:e76) may also permit activation of recombination mechanisms. Activation of recombination capability in a host cell may also be achieved by transforming or infecting the cell with an expression construct containing the repressed gene including modified codons so that the gene is not inhibited by the siRNA molecules.

Substantial impairment of the expression of one or more recombination control elements (for example, one or more of a RAG-1 gene, RAG-2 gene or TdT gene) may be achieved by a variety of methods that are well known in the art for blocking specific gene expression, including antisense inhibition of gene expression, ribozyme mediated inhibition of gene expression, siRNA mediated inhibition of gene expression, and Cre recombinase regulation of expression control elements using the Cre/Lox system. As used herein, expression of a gene encoding a recombination control element is substantially impaired by such methods for inhibiting when host cells are substantially but not necessarily completely depleted of functional DNA or functional mRNA encoding the recombination control element, or of the relevant polypeptide. In certain embodiments, recombination control element expression is substantially impaired when cells are at least about 50% depleted of DNA or mRNA encoding the endogenous polypeptide (as detected using high stringency hybridization, for example) or at least about 50% depleted of detectable polypeptide (as measured by Western immunoblot, for example); for example, at least 75% depleted or at least 90% depleted.

Screening Assays

The methods according to the present invention may optionally include one or more screening steps, for example, to screen for expression of variant proteins by the host cells and/or to screen for variants having the desired functionality and/or improvements in functionality.

Expression Assays

In certain embodiments, the methods of the invention further comprise screening the transformed host cells for expression of variants of the target protein. Various protein expression assays are known in the art and include the use of UV/VS spectrophotometry, fluorescence-based readouts including spectrophotometry and FACS, mass spectrometry and the like. As noted above, in some embodiments, the protein variants may be expressed as fusion proteins comprising additional amino acid sequences to facilitate detection, for example, by localizing the protein to the cell surface or by incorporating a detectable label.

In certain embodiments in which the protein variants are not localized to the cell surface or secreted, the expression assay may further comprise a cell lysis step, or the protein variant may be assayed intracellularly.

In some embodiments of the invention, the methods generate high numbers of variants and in such embodiments high throughput screening or selection approaches are generally preferred. Many high throughput screening approaches are well known in the art and can be readily applied to identify and select variant proteins with modified functionality. FACS based and magnetic panning is also well known in the art.

Functional Assays

In certain embodiments, the methods of the invention further comprise submitting the variant protein(s) to a functional assay to identify those variants having the desired functionality and/or improvements in functionality. The specific assay used will be dependent on the functionality being assessed. Exemplary functionalities that can be detected using a functional assay include, but are not limited to, ligand binding, enzymatic activities, and signalling activities. Various functional assays are known in the art and appropriate assays can be readily selected by one skilled in the art. Commonly used assays include, for example, binding assays, growth assays, reporter gene assays and FACS-based assays.

The functionality of the variant proteins may be assessed by assaying the cells expressing the variants or the variants may be isolated from the host cells and assayed as isolated proteins.

Polynucleotide Compositions

In certain embodiments, the invention provides for polynucleotides capable of undergoing RSS-mediated recombination when introduced into a recombination-competent host cell, and compositions comprising same. The polynucleotide preferably comprises a coding sequence that encodes a target protein as defined herein, such as a ligand-binding protein, into which two or more RSSs have been introduced. The polynucleotide compositions may be provided as isolated polynucleotides or they may be provided as part of a vector, in which case they may be operatively linked to one or more regulatory elements, such as, promoters, enhancers, terminators, alpha-factors, ribosome binding sites, polyadenylation signals and the like, as described above. The present invention also contemplates that the compositions may be provided as host cells that have been transformed with the polynucleotide or a vector comprising the polynucleotide. Examples of suitable host cells include those described above.

In certain embodiments, the polynucleotide of the composition comprises a nucleic acid sequence that encodes a target protein, such as a ligand-binding protein, and at least one complementary pair of RSSs, in which the two RSSs of the pair are (i) capable of functional recombination with each other; (ii) positioned in a portion of the nucleic acid sequence that encodes a non-conformational region of the protein, and (iii) spaced preferably 100 base pairs or more apart.

In some embodiments, the polynucleotide is a "tripartite substrate" in which the polynucleotide comprises two complementary pairs of RSSs, each pair positioned at a different location and each pair positioned in a portion of the nucleic acid sequence that encodes a non-conformational region of the protein.

In some embodiments, the polynucleotide comprises RSSs that are accompanied by flanking sequences adjacent to one or both of the heptamers of the RSS. In some embodiments, the polynucleotide comprises RSSs that are accompanied by flanking sequences that encode a specific amino acid, or amino acids, or peptide sequence.

In certain embodiments, the polynucleotide comprises a nucleic acid that encodes a ligand-binding protein and comprises at least one complementary pair of RSSs positioned in a portion of the nucleic acid sequence that encodes a loop region of the protein involved in ligand-binding.

In certain embodiments, the polynucleotide of the composition comprises a nucleic acid sequence that encodes an antibody or antibody fragment and at least one complementary pair of RSSs, in which the two RSSs of the pair are (i) capable of functional recombination with each other; (ii) positioned within a portion of the nucleic acid sequence that encodes CDR1 or CDR2, and (iii) spaced preferably 100 base pairs or more apart.

Applications

In accordance with one aspect of the present invention, the methods can be used to generate variants of a target protein with a desired functionality or an improvement or modification in an existing functionality. In certain embodiments, the methods are employed to generate a large number of variants of the target protein for subsequent screening for a desired, improved or modified functionality. In certain embodiments of the invention, the functionality may be a binding affinity or specificity for a selected ligand.

In certain embodiments, the methods are used to generate variants of a ligand-binding protein with modulated binding properties, for example, modulated affinity. Modulated affinity may comprise a decrease in affinity or an increase in affinity over the native protein. In some embodiments, therefore, the methods are used to generate variants of a ligand-binding protein with decreased affinity for a ligand. In some embodiments, the methods are used to generate variants of a ligand-binding protein with increased affinity for a ligand. Modulated binding properties also encompass in some embodiments a modified specificity, for example, an increase in specificity, a decrease in specificity or an altered specificity, for example, such that the protein binds a ligand other than the native ligand(s).

In certain embodiments, the invention provides for the use of the methods to generate ligand-binding proteins with modified binding properties (for example, modified antibodies, avimers, adnectins, or other antibody mimetics) for therapeutic purposes, for diagnostic purposes, for drug targeting (for example, through the use of a modified ligand-binding protein that targets a protein on a particular cell or tissue type as a targeting moiety for attachment to a therapeutic or diagnostic compound), or for research applications (such as screening assays, chromatography and the like).

Kits

In one aspect, the invention provides for kits comprising a polynucleotide capable of undergoing RSS-mediated recombination when introduced into a recombination-competent host cell, or a composition comprising a polynucleotide capable of undergoing RSS-mediated recombination when introduced into such a host cell, as described above.

When the kit comprises a composition, the composition may comprise an isolated polynucleotide, a polynucleotide comprised by a vector (in which case the polynucleotide may be operatively linked to one or more regulatory elements, such as, promoters, enhancers, terminators, alpha-factors, ribosome binding sites, polyadenylation signals and the like), or a host cell that has been transformed with the polynucleotide or a vector comprising the polynucleotide.

When the kit comprises an isolated polynucleotide, the kit may further comprise a vector suitable for expression of the polynucleotide and/or a recombination-competent host cell.

The kit may further comprise vectors encoding one or more of RAG-1, RAG-2 and TdT that are suitable for transforming a host cell such that the host cell expresses, or is capable of expressing, RAG-1 and/or RAG-2 and/or TdT.

The kit may further comprise one or more additional components to assist with cloning the polynucleotide and/or transformation of host cells, such as buffers, enzymes, selection reagents, growth media and the like.

One or more of the components of the kit may optionally be lyophilised and the kit may further comprise reagents suitable for the reconstitution of the lyophilised components. Individual components of the kit would be packaged in separate containers and, associated with such containers, can be instructions for use. The instructions for use may be provided in paper form or in computer-readable form, such as a disc, CD, DVD or the like.

To gain a better understanding of the invention described herein, the following examples are set forth. It will be understood that these examples are intended to describe illustrative embodiments of the invention and are not intended to limit the scope of the invention in any way.

EXAMPLES

Example 1

Preparation of Constructs for Introducing Sequence Diversity into an Avimer

A domain or avimer-encoding DNA sequences were generated by gene synthesis by GeneArt® (Invitrogen, Carlsbad, Calif.). The sequences were codon-optimized and included RSSs in the appropriate positions, an IgG1 hinge region, CH2, CH3, a 5' hemaglutin (HA) tag, a PDGFR transmembrane domain sequence and a selectable marker, as detailed in Tables 2 and 3 below.

E188 is a single A domain avimer construct and includes a pair of RSSs introduced into loop 1 of the construct and a pair of RSSs introduced into loop 2 of the construct together with flanking sequences encoding GY amino acid residues, which were selected to be a duplication of the naturally occurring residues, but could also have been non-endogenous sequences (see FIG. 3A-C).

Figure 4:
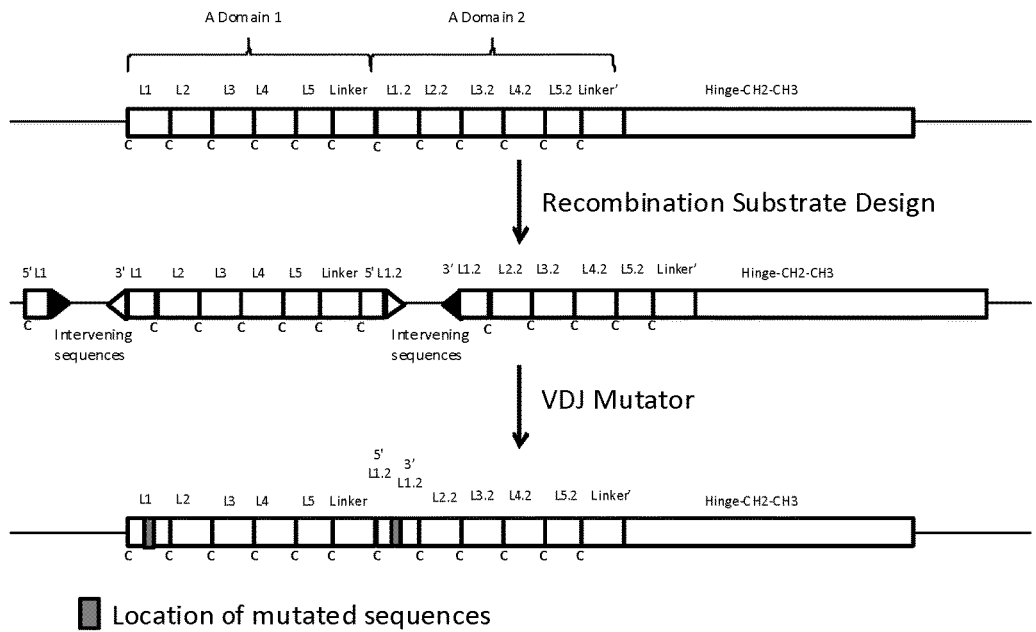
FIG. 4 presents a schematic overview of the steps for mutagenesis of a double domain A avimer construct including RSS sequences in each loop 1.

E189 is a double A domain avimer construct and includes a pair of RSSs in each loop 1 of the construct (see FIG. 4). E189 also includes stop codons in other reading frames in the 3' loop 1 to 5' loop 1.2 region, but does not include flanking sequences.

Portions of the E188 and E189 sequences are shown in FIG. 1 [SEQ ID NO:28] and FIG. 2 [SEQ ID NO:29], respectively. The complete vector sequences are provided in FIG. 17 [SEQ ID NO:1] and FIG. 18 [SEQ ID NO:40], respectively.

Figure 5:
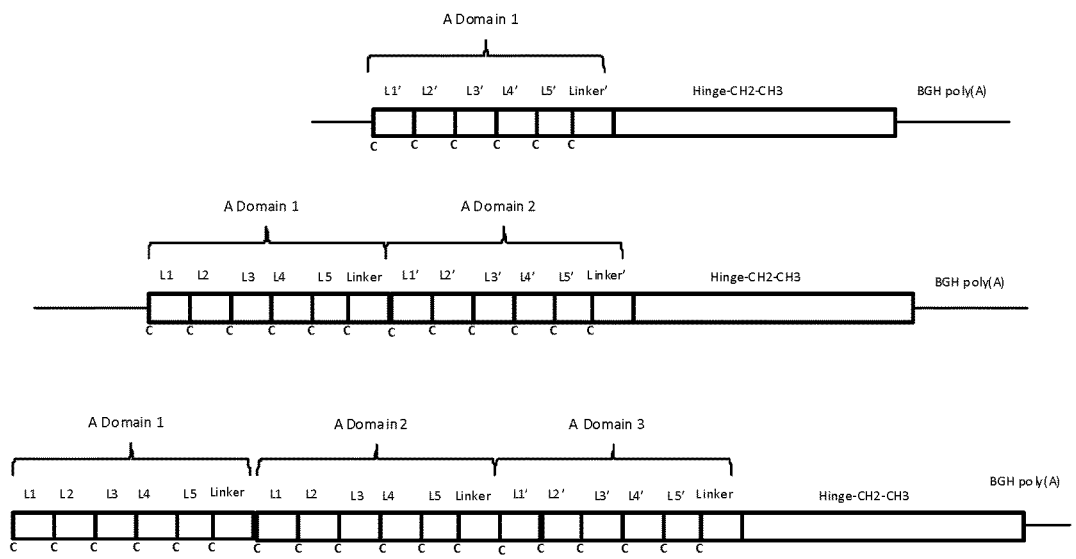
FIG. 5 presents a schematic representation of single, double and triple A domain avimer constructs.

Multiple A domain avimers can also be constructed (see FIG. 5).

TABLE 2

Sequence Annotation for [SEQ ID NO: 28]

| | |
|---|---|
| Leader | 10-66 |
| HA-tag | 67-93 |
| Coding sequences 5' loop 1 | 94-102 |
| Inserted flanking sequence | NA |
| 23 bp RSS (>) | 103-141 |
| Intervening sequence | 142-722 |
| 12 bp RSS (<) | 723-750 |
| Inserted flanking sequence | NA |
| Coding inteverning sequence 3' Loop 1/5' Loop 2 | 751-771 |
| inserted flanking sequence (GGCTAC) | 772-777 |
| 12 bp RSS (>) | 778-805 |

TABLE 2-continued

Sequence Annotation for [SEQ ID NO: 28]

| | |
|---|---|
| Intervening sequence | 806-1429 |
| 23 bp RSS (<) | 1430-1468 |
| Inserted flanking sequence | NA |
| 3' Loop 2-Loop 5 | 1469-1501 |
| Avimer linker | 1502-1561 |
| IgGI hinge CH2—CH3 | 1562-2257 |
| Transmembrane sequence | 2258-2425 |

TABLE 3

Sequence Annotation for [SEQ ID NO: 29]

| | |
|---|---|
| Leader | 10-66 |
| HA-tag | 67-93 |
| Coding sequences 5' loop 1 | 94-102 |
| Inserted flanking sequence | NA |
| 23 bp RSS | 103-141 |
| Intervening sequence | 142-722 |
| 12 bp RSS | 723-750 |
| Inserted flanking sequence | NA |
| Coding sequences 3' Loop 1-Loop 5 linker 5' Loop 1.2 | 751-870 |
| Inserted flanking sequence | NA |
| 12 bp RSS | 871-898 |
| Intervening sequence | 899-1522 |
| 23 bp RSS | 1523-1561 |
| Inserted flanking sequence | NA |
| Coding sequences 3' Loop 1.2-loop 5.2 | 1562-1609 |
| Avimer linker | 1610-1669 |
| IgGI hinge CH2—CH3 | 1670-2365 |
| Transmembrane sequence | 2366-2533 |
| Leader | 10-66 |
| HA-tag | 67-93 |
| Coding sequences 5' loop 1 | 94-102 |
| Inserted flanking sequence | NA |
| 23 bp RSS | 103-141 |
| Intervening sequence | 142-722 |
| 12 bp RSS | 723-750 |
| Inserted flanking sequence | NA |
| Coding sequences 3' Loop 1-Loop 5 linker 5' Loop 1.2 | 751-870 |
| Inserted flanking sequence | NA |
| 12 bp RSS | 871-898 |
| Intervening sequence | 899-1522 |
| 23 bp RSS | 1523-1561 |
| Inserted flanking sequence | NA |
| Coding sequences 3' Loop 1.2-loop 5.2 | 1562-1609 |
| Avimer linker | 1610-1669 |
| IgGI hinge CH2—CH3 | 1670-2365 |
| Transmembrane sequence | 2366-2533 |

The synthesized DNA was cloned into a modified pcDNA (Invitrogen, Carlsbad, Calif.) that contains a consensus Kozak sequence and a mammalian leader signal sequence ([SEQ ID NO:36]; see Example 7) for efficient secretion or surface expression of the recombined avimers. The modified pcDNA acceptor vector allows for cloning of the avimer construct so that the 3' end is fused to the Fc portion of human IgG1 followed by a PDGFR transmembrane domain and selectable marker such that the recombined molecules are surface expressed and can be selected for in-frame products. The nucleotide sequences for the IgG hinge through CH3 sequences and a transmembrane domain are shown in FIG. 7D [SEQ ID NO:35]. The avimer scaffold was cloned at the KpnI site (bolded in FIG. 7D), which translates as a Gly-Thr prior to the hinge sequences of IgG1.

Example 2

Generation of Surface Expressed Avimer Mutants

Avimer vectors containing E188 prepared as described in Example 1 were transfected into a recombination competent cell line (see Example 10) and stable neomycin integrants were generated. The sequences of the expressed avimer mutants were obtained as described in Example 4 below.

Example 3

Generation of Libraries of Surface Expressed Avimer Mutants

Avimer vectors containing E188 prepared as described in Example 1 were stably integrated into a recombination competent cell line. Stable integrants were expanded and then transfected with plasmids expressing RAG1/RAG2/TdT. The transfection was carried out using $1 \times 10^7$ stable integrants transfected with 8ug each of RAG1, RAG2 and TdT expression vectors using a 3:1 ratio of linear PEI (1 mg/ml) to DNA. (See Example 10 for details).

RAG1/RAG2/TdT treated cells were then stained using anti-IgG Fc to confirm surface expression of the recombined avimer molecules. Approximately $1 \times 10^6$ cells were stained with 1 ug/ml Biotin conjugated anti-human IgG Fc (Jackson Laboratories) for 30 min. The cells were then washed twice and stained with streptavidin-conjugated Alexa-647 for 30 min. Samples were subsequently washed twice, resuspended in 300 ul of PBS and analyzed using flow cytometry. The recombined population was shown to have high uniform expression. The sequences of the expressed avimer mutants were obtained as described in Example 4 below.

Example 4

Sequence Analysis of Avimer Mutants (Single A Domain)

RNA samples obtained from FACS sorted cells (Example 3) were used for sequence analysis of the expressed avimer variants. mRNA from approximately $10^6$ recombined cells was purified using Qiagen RNeasy RNA purification kit as per the manufacturer's recommendations. cDNA synthesis was carried out using Superscript enzyme (Invitrogen, Carlsbad, Calif.) as per the manufacturer's recommended protocol and primer MG59 (sequence 5'-TCTTGGCATTAT-GCACCTCCACGCCGTCC-3' [SEQ ID NO:30]).

The cDNA was then used as a template and amplified using primer MG301 (sequence 5'-GAGAGAGATTG-GTCTCGAGAACCCACTGCTTACTGCTCGACGATCT-GAT-3' [SEQ ID NO:31]), which anneals in the 5' UTR region, and primer MG58 (sequence 5'-GTCTTCGTGGCT-CACGTCCACCACCACGCA-3' [SEQ ID NO:32]), which anneals internal to the MG59 primer used in the RT reaction.

The amplified product was purified using a Qiagen PCR clean up kit as per the manufacturer's recommended protocol and eluted into 35 ul of water. The purified PCR product was then digested with BsaI (NEB) and cloned into the modified pcDNA acceptor vector (Invitrogen, Carlsbad, Calif.) with corresponding compatible ends. Plasmid DNA from *E. coli* cultures was purified using Qiagen Miniprep kit and avimer sequences were analyzed using primer MG60 (sequence 5'-CTGACCTGGTTCTTGGTCAGCTCATC-CCG-3' [SEQ ID NO:33]).

The results are presented in Tables 4A,B and 5 below.

TABLE 4A

Nucleotide Sequence Analysis Of Single A Domain Avimer Variants (Loop 1)

| Mutant # | 5' Deletions | Additions | 3' Deletions |
|---|---|---|---|
| 1 | -1 | | -2 |
| 2 | 0 | AGGGCCAAGA [SEQ ID NO: 16] | -15 |
| 3 | -1 | GAG | -2 |
| 4 | 0 | C | -1 |
| 5 | -2 | TAGGGGGTTCCAGT [SEQ ID NO: 17] | -13 |
| 6 | 0 | AGAA | -3 |
| 7 | 0 | AGTGGGGAT | 0 |
| 8 | -1 | CCC | -6 |
| 9 | -1 | CCT | -2 |
| 10 | -2 | T | 0 |
| 11 | -8 | TCC | -4 |
| 12 | 0 | AC | -3 |
| 13 | 0 | AGAAGG | -3 |
| 14 | -3 | TTATTA | -1 |
| 15 | -2 | AAGAC | -12 |
| 16 | 0 | CC | -5 |
| 17 | -1 | CTC | -3 |
| 18 | 0 | AGG | 0 |
| 19 | 0 | | -1 |
| 20 | 0 | CG | -5 |
| 21 | 0 | AGAC | -1 |

TABLE 4B

Nucleotide Sequence Analysis Of Single A Domain Avimer Variants (Loop 2)

| Mutant # | 5' Deletions | Additions | 3' Deletions |
|---|---|---|---|
| 1 | 0 | GA | -2 |
| 2 | -7 | TGGGGTTAAGCCTC [SEQ ID NO: 18] | -2 |
| 3 | 0 | | 0 |
| 4 | 0 | GGG | -6 |
| 5 | -2 | GAG | 0 |
| 6 | -12 | CCCTCCGTCCTACCTC [SEQ ID NO: 19] | -2 |
| 7 | -12 | C | -4 |
| 8 | -14 | TCCAGTGCGGCTCCGGGA [SEQ ID NO: 20] | -24 |

TABLE 4B-continued

Nucleotide Sequence Analysis Of Single A Domain Avimer Variants (Loop 2)

| Mutant # | 5' Deletions | Additions | 3' Deletions |
|---|---|---|---|
| 9 | -2 | TC | 0 |
| 10 | -2 | | -3 |
| 11 | -4 | CTACA | -4 |
| 12 | -4 | CG | -3 |
| 13 | 0 | | -3 |
| 14 | 0 | | -2 |
| 15 | 0 | GTC | -2 |
| 16 | 0 | | -6 |
| 17 | -13 | | -4 |
| 18 | -23 | GGAGCCGCACTGGAACT [SEQ ID NO: 21] | 0 |
| 19 | -2 | | -6 |
| 20 | -2 | CT | -6 |
| 21 | -2 | TCCC | -2 |

TABLE 5

Amino Acid Sequence Analysis Of Single A Domain Avimer Variants

| Mutant # | Loop 1 (5') | Loop 1 (3')/ Loop2 (5') | Loop 2 (3') and loop 3 | Total aa Length (from CAP to GYC) | SEQ ID NO |
|---|---|---|---|---|---|
| Parent | DYACAP | SQFQCGSGY | GYCISQRWVCD | 15 | 22 |
| 1 | DYA | FQFQCGSGYN | CISQRWVCD | 10 | 23 |
| 2 | DYACAP | TSSSAAPAY | CISQRWVCD | 13 | 24 |
| 3 | DYACAP | RRQFQCGSGY | YCISQRWVCD | 14 | 25 |
| 4 | DYACA | LLASSSAAPAT | YCISQRWVCD | 13 | 26 |
| 5 | DYACA | QDAAPATS | YCISQRWVCD | 13 | 27 |
| 6 | DYACAP | PQFQCGSGY | CISQRWVCD | 13 | 42 |
| 7 | DYACAP | SSSSD | CISQRWVCD | 13 | 43 |
| 8 | DYACAP | RSRSRTGT | GYCISQRWVCD | 15 | 44 |
| 9 | DYACAP | ASSSAAPA | CISQRWVCD | 13 | 45 |
| 10 | DYACAP | RFQCGSGS | CISQRWVCD | 13 | 46 |
| 11 | DYACAP | RRQFQCGSGFP | YCISQRWVCD | 14 | 47 |
| 12 | DYACAP | QFQCGSGYD | YCISQRWVCD | 14 | 48 |
| 13 | DYACAP | RAKRLWGAS | YCISQRWVCD | 14 | 49 |
| 14 | DYACAP | SQFQCGSGY | GYCISQRWVCD | 15 | 50 |
| 15 | DYACAP | RQFQCGSGYG | CISQRWVCD | 13 | 51 |
| 16 | DYACA | LGGSSAAPAE | GYCISQRWVCD | 14 | 52 |
| 17 | DYACAP | RTVPVPLRPTS | YCISQRWVCD | 14 | 53 |
| 18 | DYACAP | SGDSQFQCH | CISQRWVCD | 13 | 54 |
| 19 | DYACAP | PSSSSAAPG | VCD | 7 | 55 |
| 20 | DYACAP | LQFQCGSGF | GYCISQRWVCD | 15 | 56 |
| 21 | DYACA | LASSSAAPA | YCISQRWVCD | 13 | 57 |

This data indicates that net size of the product is still smaller than the original product indicating that this is a situation in which additional flanking sequences may be beneficial. The data also demonstrated that a large fraction of products used the other reading frames for the RSS flanked cassette and as a result eliminated the cysteine residue. To counter this, an alternative cassette was designed as described in Example 6 below.

Example 5

Large Libraries of Avimer Mutants from an Inducible Cell Line

Avimer vectors prepared as described in Example 1 will be stably integrated into a cell line which constitutively expresses RAG2, Tdt and the Tet repressor (TetR, Life Technologies). The cell line will also have stably integrated RAG1 whose expression can be regulated via the addition of tetracycline (T-Rex System, Life Technologies). Stable avimer mutator integrants will be expanded to 100 million cells and RAG1 expression induced via the addition of 1 ug/ml tetracycline (Life Technologies). Tetracycline will be maintained for a period of 2-14 days, or longer, to allow the V(D)J reaction to proceed.

Example 6

Alternative Construct for Introducing Sequence Diversity into an Avimer

The cassette used in Example 1 (see FIG. 6A) was redesigned as shown in FIG. 6B. The alternate cassette includes as additional flanking sequences, a TAC at both the 5' end and the 3' end (adding potential tyrosine if not deleted). The modified cassette also includes nucleotide changes that add cysteines in the other frames to help ensure retention of a cysteine in the final product.

Example 7

Preparation of Constructs for Introducing Sequence Diversity into a Fibronectin Domain Two constructs based on the 10Fn3 scaffold will be prepared as follows. The nucleotide sequences containing the 10Fn3 exon (FIG. 7A [SEQ ID NO:34]) will be cloned behind the CMV promoter and a heterologous leader sequence and include a downstream BGH poly (A). The nucleotide sequence of the leader is:

[SEQ ID NO: 36]
5'-atggagtttgggctgagctggcttttcttgtggctattttaaaagg tgtccagtgt-3'

The 10Fn3 scaffold will be cloned in frame with the IgG1 hinge through CH3 sequences and a transmembrane domain for cell surface expression, as well as a selectable marker cassette that allows for in-frame selection of recombination products. The nucleotide sequences for the IgG hinge through CH3 sequences and a transmembrane domain are shown in FIG. 7D [SEQ ID NO:35]. The 10FN3 scaffold will be cloned at the KpnI site (bolded in FIG. 7D), which translates as a Gly-Thr prior to the hinge sequences of IgG1.

Figure 8:
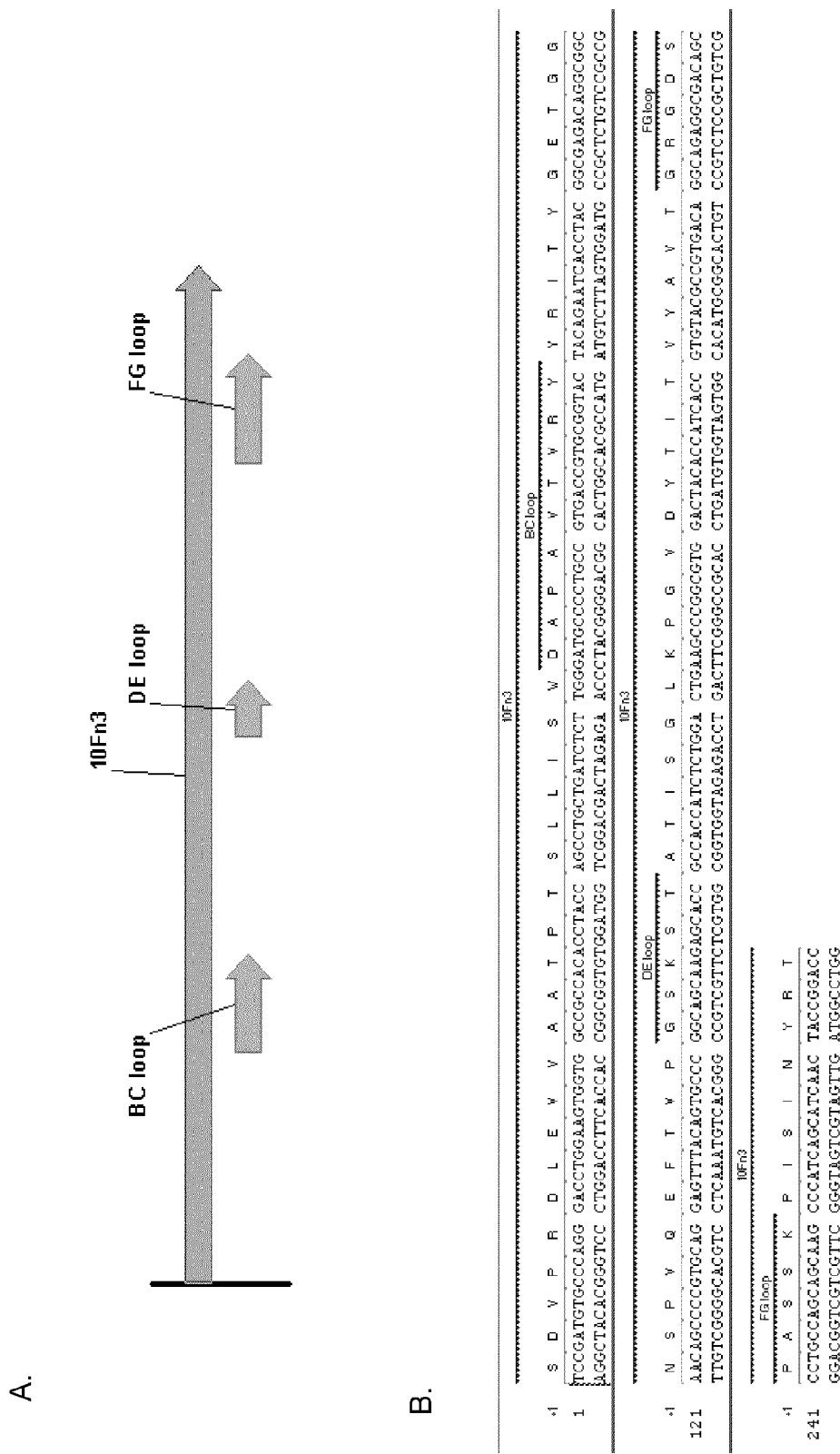
FIG. 8 presents (A) a schematic representation of the location of the loop regions (BC, DE and FG) of 10Fn3, and (B) the nucleotide and amino acid sequences of 10Fn3 with the loop regions indicated [SEQ ID NOs: 92 & 93].
Figure 9D:
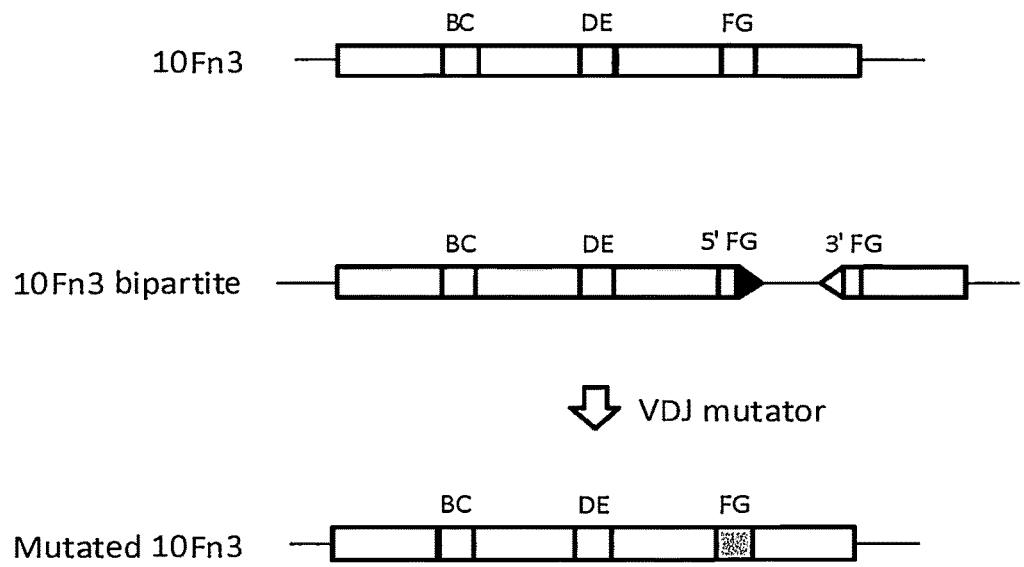
FIG. 9 presents a schematic representation of (A) a bipartite 10Fn3 construct comprising a single pair of RSSs in the FG loop, (B) sequence details of the 23 bp RSS shown in (A) [topmost sequence: SEQ ID NO:94; bottom sequence: SEQ ID NO: 110], (C) sequence details of the 12 bp RSS shown in (A) [topmost sequence: SEQ ID NO:95; bottom sequence: SEQ ID NO: 111], and (D) an overview of the steps for mutagenesis of the 10Fn3 construct shown in (A).

RSSs will be introduced into the region of the 10Fn3 nucleotide sequence that encodes the FG loop (see FIG. 8, which depicts the location of the loop regions of 10Fn3). In the first construct, a 289 bp (heptamer to heptamer) sequence cassette containing one pair of RSSs will be introduced (see FIG. 9). The sequence of this construct is shown in FIG. 10A [SEQ ID NO:37], in which the 23 bp RSS and the 12 bp RSS are shown in bold.

In the second construct, two pairs of RSSs will be introduced into the FG loop (see FIG. 11) using a 289 bp (heptamer to heptamer) sequence cassette for the 5' RSSs and a 427 bp (heptamer to heptamer) sequence cassette for the 3' RSSs. The sequence of this construct is shown in FIG. 10B [SEQ ID NO:38], in which the 23 bp RSSs and the 12 bp RSSs are shown in bold.

Figure 11E:
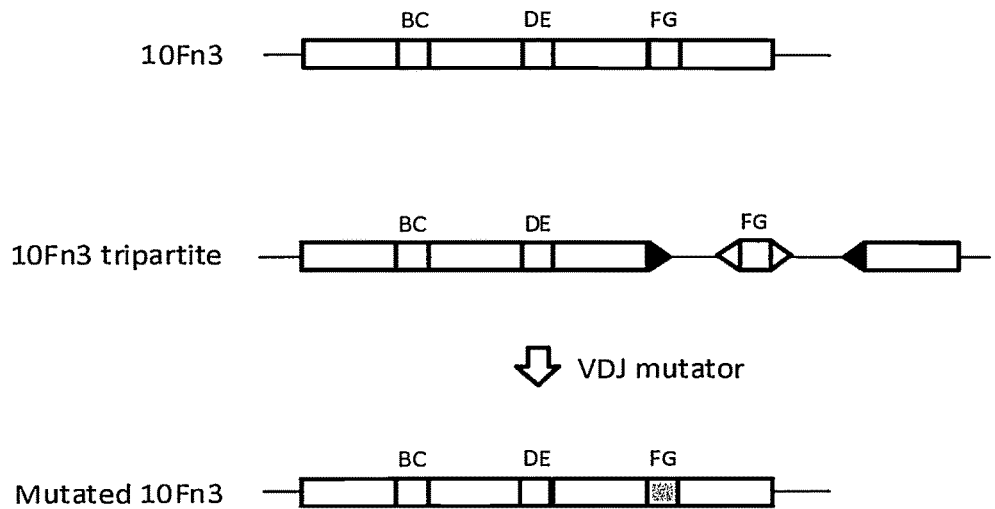
FIG. 11 presents a schematic representation of (A) a tripartite 10Fn3 construct comprising two pairs of RSSs in the FG loop, (B) sequence details of the 5' 23 bp RSS shown in (A) [topmost sequence: SEQ ID NO:96; bottom sequence: SEQ ID NO: 112], (C) sequence details of the 5' 12 bp RSS and the 3' 12 bp RSS shown in (A) [topmost sequence: SEQ ID NO:97; bottom sequence: SEQ ID NO: 113] and the encoded FG loop sequences [from top to bottom: SEQ ID NOs:98-100], (D) sequence details of the 3' 23 bp RSS shown in (A) [topmost sequence: SEQ ID NO:101; bottom sequence: SEQ ID NO: 114], and (E) an overview of the steps for mutagenesis of the 10Fn3 construct shown in (A).

In the second construct, repeat sequences will be included with the RSSs as shown in FIG. 11. As an alternative to repeat sequences, heterologous sequences could be included, for example, sequences encoding the amino acid histidine that could potentially allow for binders to be isolated that had pH dependent binding. Also in the second construct, stop codons will be eliminated from the sequence being flanked by the RSSs so that all three frames have the potential to generate a functional protein.

Figure 12:
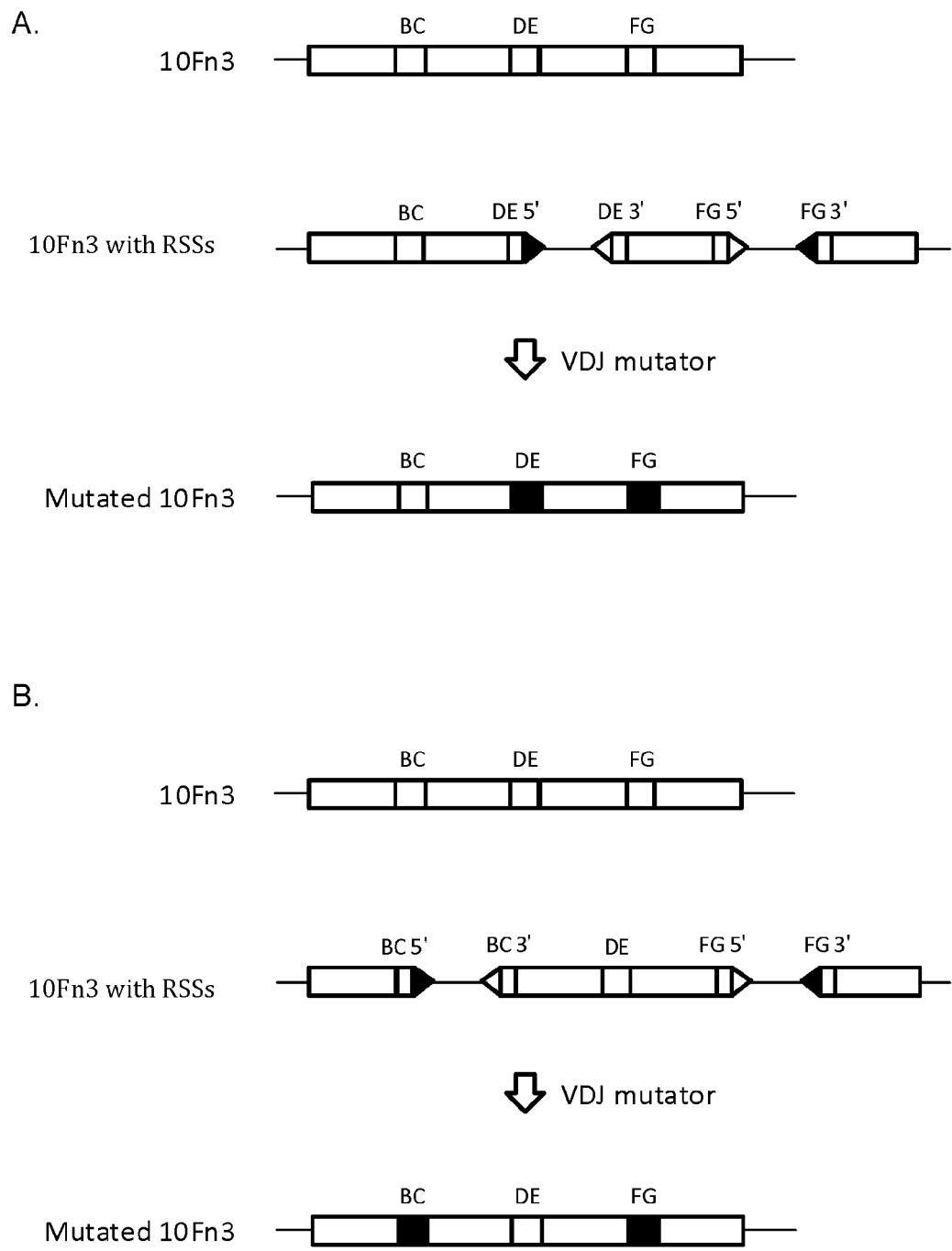
FIG. 12 presents (A) a schematic overview of the steps for mutagenesis of a tripartite 10Fn3 construct that allow for simultaneous diversification of the DE and FG loops, and (B) a schematic overview of the steps for mutagenesis of a tripartite 10Fn3 construct that allow for simultaneous diversification of the BC and FG loops.

Additional examples of potential positioning of RSSs in the 10Fn3 sequence that allow for simultaneous diversification of two loops are shown in FIG. 12A (diversification of the DE and FG loops) and 12B (diversification of the BC and FG loops). Diversification of the BC and DE loops is also contemplated.

Example 8

Introduction of Sequence Diversity into CDR2 of an Immunoglobulin Heavy Chain

The sequence of the heavy chain VDJ regions is shown in FIG. 16A, with CDR1 and CDR2 indicated in bold. The following strategy (depicted in FIG. 14) will be employed in order to introduce sequence diversity into CDR2 of this heavy chain.

A 289 bp (from heptamer to heptamer) sequence cassette including a 5' 23 bp RSS and a 3' 12 bp RSS (shown below [SEQ ID NO:6]) will be introduced into CDR2 and the resulting modified heavy chain coding sequence cloned behind the CMV promoter and a heterologous leader sequence and will include a downstream BGH poly (A), as described in Example 7 for the modified 10Fn3. The sequence of the modified heavy chain coding sequence is shown in FIG. 16B.

[SEQ ID NO: 6]
5'-cacagtggtagtactccactgtctgggtgtacaaaaacctccctgca cgcctctctaacctcacaattctgtggcggccgctttgtagccagaccct cggtcaactggatgtcacaactggcacctgagattggaaacataaaaaca aatattcttactattaatcatgttatcagagaacttccctgaagttccag tcagtactgtgactagctaattagtcagttacttaagcgtctatccaagt gcaaagggacaggaggttttttgttaagggctgtatcactgtg-3'

Example 9

Introduction of Sequence Diversity into Both CDR1 and CDR2 of an Immunoglobulin Heavy Chain The heavy chain described in Example 3 will be used and the following strategy (depicted in FIG. 15) will be employed in order to introduce sequence diversity into CDR1 and CDR2. The following cassettes will be used.

CDR1 cassette, including a 5' 23 bp RSS and a 3' 12 bp RSS with a 222 bp intervening sequence and a trinucleotide repeat sequence (AGC) located 5' of the 23 bp RSS heptamer:

[SEQ ID NO: 7]
5'-agccacagtggtagtactccactgtctgggtgtacaaaaacctccct gcacgcctctctaacctcacaattctgtggcggccgctttgtagccagac cctcggtcaactggatgtcacaactggcacctgagattggaaacataaaa acaaatattcttactattaatcatgttatcagagaacttccctgaagttc cagtcagtactgtgactagctaattagtcagttacttaagcgtctatcca agtgcaaagggacaggaggttttttgttaagggctgtatcactgtg-3'

CDR2 cassette, including a 5' 12 bp RSS and a 3' 23 bp RSS with a 360 bp intervening sequence and a trinucleotide repeat sequence (ACC) located 5' of the 12 bp RSS heptamer:

[SEQ ID NO: 8]
5'-acccacagtgatacagcccttaacaaaaacccctactgcaacctggc ggtaatagacgtccggaagcacactggctgagtaaattcctagtgttctc catccttacctcggagccagagtagcaggagccactagccagcttgggtc ttcctatcgcgagtcgtattaatttcgataagccagcaagcagtgggttc tctagttagccagctgcctcattctctgggcccagcgtcctctgtcctgg agctgggagataatgtccggggggctccttggtctgcgctgggcaaagggt gggcagagtcatgcttgtgctggggacaaaatgaccttgggacacggtcg acgggctggctgccacggccggcccgggacagtcggagagtcaggttttt gtacacccagacagtggagtactaccactgtg-3'

A modified heavy chain coding sequence including the CDR1 and CDR2 cassettes shown above will be gene synthesized and cloned behind the CMV promoter and a heterologous leader sequence. The construct will also include a downstream BGH poly(A), as described in Example 7 for the modified 10Fn3. The sequence of the modified heavy chain coding sequence is shown in FIG. 16C [SEQ ID NO:5].

Example 10

Recombination and Expression of Recombination Substrates

In brief, HEK293 cells, containing an integrated LoxP sequence (Fukushige et al., 1992, *PNAS USA*, 89:7905-7909; Baubonis et al., 1993, *NAR*, 21(9):2025-2029; Thomson et al., 2003, *Genesis*, 36:162-167) were maintained in DMEM media with 10% FBS. Integration into the LoxP site was shown to support high protein expression and also support V(D)J recombination of inserted substrates and provides an easy method to generate integrants with the required properties. Vectors comprising the recombination substrate were designed to include a LoxP site for targeted integration which is in-frame with a codon-optimized hygromycin open reading frame. Bipartite vectors were also designed so that productive rearrangements will be in-frame with the selectable marker neomycin. The neomycin gene is cloned in-frame with a transmembrane domain both of which are positioned downstream of a furin cleavage site that allows for secretion of the encoded protein (see FIG. 19 and SEQ ID NO:41, as an example).

For example, for bipartite substrates, HEK293 cells containing the LoxP site were co-transfected with the bipartite substrate containing the hygromycin gene for selection of stable integrants and a vector expressing the CRE protein at a ratio of 10:1 substrate to CRE expressing vector. Specifically, a 10 cm dish of cells was transfected using a polyethylenimine (PEI; 1 mg/ml) to DNA ratio of 3:1. 21.6 ug of substrate DNA was mixed with 2.4 ug of CRE expression vector and placed in 1.5 ml OptiMEM™ media and mixed with an equal volume of OptiMEM™ containing the 72 ul of PEI. The transfection was carried out for 24 hours and the following day the transfection media was removed and replaced with fresh DMEM media. The following day the transfected cells were split into ten 10 cm² dishes and selection was carried out for approximately 2 weeks. A pool of stable hygromycin resistant cells were selected. The cell line was subsequently expanded in the un-recombined state to approximately 10 million cells and transfected with RAG-1, RAG-2 and TdT. 72 hours post-transfection the cells were placed in neomycin selection (1 mg/ml).

Tripartite recombination substrates used vectors designed such that puromycin could be used for in-frame selection. Tripartite vectors also included a modified neomycin cassette that allows maintenance of the unrecombined substrate during expansion.

Example 11

Sequence Analysis of Avimer Mutants (Double A Domain)

Avimer vectors containing E189 prepared as described in Example 1 were stably integrated into a recombination competent cell line as described in Example 3 and sequence analysis was conducted as described in Example 4. The results are shown in Tables 6-8, below.

TABLE 6

Nucleotide Sequence Analysis Of Double A Domain Avimer Variants

| Mutant # | A1-L1 5' Deletions | A1-L1 Additions | A1-L1 3' Deletions | A2-L1 5' Deletions | A2-L1 Additions | A2-L1 3' Deletions |
|---|---|---|---|---|---|---|
| 1 | −4 | T | 0 | −2 | TCC | −1 |
| 2 | 0 |  | 0 | −4 | GAG | −5 |
| 3 | 0 | GG | −2 | −2 | AC | 0 |
| 4 | −1 | T | 0 | 0 | CTCCTT | 0 |
| 5 | −2 |  | −4 | −6 | GG | −5 |
| 6 | −3 |  | 0 | −13 | CGAGGGT | 0 |
| 7 | 0 | GGAACAGG | −2 | −10 | GGCC | 0 |

TABLE 7

Amino Acid Sequence Analysis Of Double A Domain Avimer Variants (A Domain 1)

| Mutant # | A1 Loop 1 (5') | A1-Loop 1 (3') - End A1 | Total aa Length from $CLP_U$ to $DQFRC_D$ | SEQ ID NO |
|---|---|---|---|---|
| Parent | DYACLP | DQFRCGNGQCIPLDWVCD GVNDCPDSDEEGC | 8 | 58 |
| 1 | DYACL | DQFRCGNGQCIPLDWVCD GVNDCPDSDEEGC | 7 | 59 |
| 2 | DYACLP | DQFRCGNGQCIPLDWVCD GVNDCPDSDEEGC | 8 | 60 |
| 3 | DYACLP | GQFRCGNGQCIPLDWVCD GVNDCPDSDEEGC | 8 | 61 |
| 4 | DYACLP | DQFRCGNGQCIPLDWVCD GVNDCPDSDEEGC | 8 | 62 |
| 5 | DYACL | QFRCGNGQCIPLDWVCD GVNDCPDSDEEGC | 6 | 63 |
| 6 | DYACL | DQFRCGNGQCIPLDWVCD GVNDCPDSDEEGC | 7 | 64 |
| 7 | DYACLP | GTGQFRCGNGQCIPLDWV CDGVNDCPDSDEEGC | 10 | 65 |

TABLE 8

Amino Acid Sequence Analysis Of Double A Domain Avimer Variants (A Domain 2)

| Mutant # | A1-A2 linker | A2 Loop 1 (5') | A2 Loop 1 (3')- Loop 2 | Total aa Length from CAPSQ$_D$ to FQC$_J$ | SEQ ID NO |
|---|---|---|---|---|---|
| Parent | PPRT | CAPSQ | FQCGSGYCI | 8 | 66 |
| 1 | PPRT | CAPSLL | QCGSGYCI | 8 | 67 |
| 2 | PPRT | CAPRR | CGSGYCI | 6 | 68 |
| 3 | PPRT | CAPSH | FQCGSGYCI | 8 | 69 |
| 4 | PPRT | CAPSQLL | FQCGSGYCI | 10 | 70 |
| 5 | PPRT | CAPG | CGSGYCI | 4 | 71 |
| 6 | PPRT | CE | FQCGSGYCI | 4 | 72 |
| 7 | PPRT | CAA | FQCGSGYCI | 5 | 73 |

Example 12

Introduction of Sequence Diversity into CDR2 of an Immunoglobulin Light Chain

A plasmid, ITS001-V655 (SEQ ID NO:74; FIG. 20), was constructed that encodes sequences that permit light chain CDR2 optimization of a HER2-specific antibody. The plasmid consists of a light chain CDR2 optimization cassette, a membrane-anchored heavy chain expression cassette and elements required for propagation in E. coli and targeted mammalian cell integration.

Details of the CDR2 optimization cassette are shown in FIG. 21A. The light chain variable region is interrupted at CDR2 bp three nucleotides of flanking sequence ('CTG', position 5870 to 5872), a 23-bp RSS (position 5873 to 5911), a spacer region, a 12-bp RSS in the inverted orientation (position 6197 to 6224) and three nucleotides of flanking sequence ('TCC', position 6225 to 6227). The light chain variable region is followed by an intron, the kappa constant region, a furin cleavage site, a transmembrane domain and a G418 resistance marker that provides selection for in-frame kappa genes following RAG-mediated recombination.

A stable cell line was generated by using Cre recombinase to target ITS001-V655 to a locus suitable for RAG-mediated recombination. The line was expanded, recombination induced and cells expressing recombined in-frame light chain genes were selected using G418. This population was enriched for binding to HER2 bp staining the recombined cells using 1 ug/ml Biotin-HER2 ECD and then isolated using MACS MicroBeads as per manufacturer's suggested protocol. The enriched population, assigned the name ITS001-L145, was analyzed by flow cytometry for expression of cell surface antibody and for binding to HER2. The cells were stained with anti-human kappa-PE (1:5000, VENDOR), 1 ug/ml Biotin HER2 ECD and 1 ug/ml Streptavidin Alexa 647 (Jackson Laboratories) and then analyzed on a C6 Accuri. As shown in FIG. 21B, cells within the population had different ratios of HER2 binding to antibody expression, which suggested that antibodies with different affinities for HER2 had been generated. When the ITS001-L145 line was compared to cells expressing the original HER2 antibody, the majority of IT001-L145 events had a higher ratio of HER2 binding to antibody expression.

Flow cytometry was used to isolate cells from ITS001-L145 with the highest HER2 to antibody expression ratio. Total RNA was extracted followed by RT-PCR of the light chain variable gene. The PCR product was then cloned into an expression vector with the original heavy chain expression cassette. Isolated clones were transiently transfected into HEK-293 cells via PEI mediated transfection and compared to the original antibody in a FACS-based assay as described above for HER2 binding and antibody expression 48 hrs post transfection. As shown in FIGS. 22A & B, clones with substantially higher ratios than the original antibody were found. These results demonstrate that V(D)J recombination can be used to precisely target mutations to a selected region of a protein and that sufficient diversity can be generated to create antibody variants with improved function (affinity).

CDR2 sequences from isolated clones are shown in Table 9.

TABLE 9

Light Chain CDR2 Sequences from Isolated Clones

| Clone ID | Amino Acid Sequence at Light Chain CDR2 | SEQ ID NO |
|---|---|---|
| Original | YAASS-----LQS | 75 |
| 2 | FVAST-----LQS | 76 |
| 4 | YAASSLQ---GLS | 77 |
| 5 | YAASSLPPS-LQS | 78 |
| 7 | FVASR-----LQS | 79 |
| 9 | YAASSQAGLSLQS | 80 |

Example 13

Introduction of Sequence Diversity into CDR1 of an Immunoglobulin Light Chain

ITS001-P126 consists of a library of plasmids that permit light chain CDR1 optimization of a HER2-specific antibody. Each plasmid consists of a light chain CDR1 optimization cassette, a membrane-anchored heavy chain expression cassette and elements required for propagation in E. coli and targeted mammalian cell integration.

In each plasmid, the light chain variable region is interrupted within CDR1 bp the addition of flanking 23-bp RSS and 12-bp RSS. The light chain variable region is followed by an intron, the kappa constant region, a furin cleavage site, a transmembrane domain and a G418 resistance marker that provides selection for in-frame kappa genes following RAG-mediated recombination. Additional variations of the CDR1 optimization vector were generated including different flanking sequences as well as additional mutations upstream or downstream of the break targeted by the RSSs. These changes introduce sequence diversity in addition to that resulting from RAG-mediated recombination.

A pool of stable cell lines incorporating different CDR1 optimization vectors was generated. The cell lines were generated by using Cre recombinase to target each CDR1 recombination substrate to a locus suitable for RAG-mediated recombination. The line was expanded, recombination induced and cells expressing recombined in-frame light chain genes selected using G418. This population was enriched for binding to HER2 in two rounds using MACS MicroBeads. The enriched population, assigned the name ITS001-L167, was analyzed by flow cytometry for expression of cell surface antibody and for binding to HER2. As shown in FIG. 23A, cells within the population had different ratios of HER2 binding to antibody expression, which suggested that antibodies with different affinities for HER2 had been generated. When the ITS001-L167 line was compared to cells expressing the original HER2 antibody, the majority of IT001-L167 events had a higher ratio of HER2 binding to antibody expression.

Flow cytometry was used to isolate cells from ITS001-L167 with the highest HER2 to antibody expression ratio. Total RNA was extracted followed by the generation of light chain gene cDNA and cloning into an expression vector with the original heavy chain expression cassette. Clones were isolated and compared to the original antibody in a FACS-based assay for HER2 binding and antibody expression. As shown in FIGS. 23B & C, clones with substantially higher ratios than the original antibody were found.

CDR1 sequences from isolated clones are shown in Table 10.

TABLE 10

Light Chain CDR1 Sequences from Isolated Clones

| Clone ID | Amino Acid Sequence at Light Chain CDR1 | SEQ ID NO |
|---|---|---|
| Original | RASQSI---SSYLN | 81 |
| 1 | RHSQRKSDVSGYAN | 82 |

TABLE 10-continued

Light Chain CDR1 Sequences from Isolated Clones

| Clone ID | Amino Acid Sequence at Light Chain CDR1 | SEQ ID NO |
|---|---|---|
| 8 | RHSQRKWDVSGYAN | 83 |
| 10 | RAPQPY--IRGYLN | 84 |
| 15 | RHSQRKFDVSGYAN | 85 |

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. A method of generating a variant of an antibody, an antigen-binding domain of the antibody or a T-cell receptor (TCR), wherein the variant binds to an antigen with increased antigen-binding affinity, the method comprising the steps of:
   (i) providing a polynucleotide comprising:
      (a) a nucleic acid sequence comprising the coding region of the antibody, the antigen-binding domain, or the TCR and
      (b) a sequence cassette that comprises a first recombination signal sequence (RSS) linked by an intervening nucleotide sequence of 100 base pairs or more in length to a second RSS, the first RSS being capable of functional recombination with the second RSS, wherein the sequence cassette is located within and interrupts a nucleotide sequence encoding a complementarity determining region 1 (CDR1) or complementarity determining region 2 (CDR2) of the coding region encoding the antibody, the antigen-binding domain, or the TCR;
   (ii) introducing the polynucleotide into a recombination-competent host cell,
   (iii) culturing the host cell in vitro under conditions allowing recombination and expression of the nucleic acid sequence, and
   (iv) identifying variants of the antibody, antigen-binding domain, or TCR with increased antigen-binding affinity relative to affinity of the antibody, the antigen-binding domain of the antibody, or the TCR to the antigen.

2. The method according to claim 1, wherein the recombination-competent host cell is capable of expressing RAG-1 and RAG-2, wherein expression of at least one of RAG-1 and RAG-2 is under inducible control, and wherein step (iii) comprises inducing expression of the at least one of RAG-1 and RAG-2.

3. The method according to claim 2 further comprising expansion of the host cell prior to step (iii).

4. The method according to claim 1, wherein the nucleic acid sequence comprises the coding region of the antibody or of the antigen-binding domain and wherein CDR1 is a light chain CDR1 or the CDR2 is a light chain CDR2.

5. The method according to claim 1, wherein the nucleic acid sequence comprises the coding region of the antibody or of the antigen-binding domain and wherein the CDR1 is a heavy chain CDR1 or the CDR2 is a heavy chain CDR2.

6. The method according to claim 1, wherein the variant is a T-cell receptor variant.

7. The method according to claim 1, wherein the sequence cassette further comprises flanking sequences adjacent to one or both of the first and second RSSs.

8. The method according to claim 1, wherein the nucleic acid sequence further comprises a second sequence cassette that comprises a third RSS linked by a second intervening nucleotide sequence to a fourth RSS, the third RSS capable of functional recombination with the fourth RSS.

9. The method according to claim 8, wherein the second sequence cassette further includes flanking sequences adjacent to one or both of the third and fourth RSSs.

10. The method according to claim 7, wherein the flanking sequences encode one or more histidine residues.

11. The method according to claim 1, wherein the polynucleotide further comprises additional coding sequences that encode a membrane anchor domain peptide.

12. The method according to claim 2, wherein the recombination-competent host cell is capable of expressing terminal deoxynucleotidyl transferase (TdT).

13. The method according to claim 1, wherein the polynucleotide is stably integrated into the genome of the host cell.

14. The method according to claim 13, wherein the polynucleotide is stably integrated into the genome of the host cell as a single copy.

15. The method according to claim 1, wherein the variant is an antibody.

16. The method according to claim 1, wherein the variant is an antigen-binding domain of an antibody.

* * * * *